(12) United States Patent
Drucker et al.

(10) Patent No.: US 9,168,288 B2
(45) Date of Patent: Oct. 27, 2015

(54) METHODS FOR TREATING DISORDERS OF THE GASTROINTESTINAL TRACT USING A GLP-1 AGONIST

(75) Inventors: Daniel J. Drucker, Toronto (CA); Laurie Lynn Baggio, Toronto (CA)

(73) Assignee: Mount Sinai Hospital, Toronto, Ontario (CA)

(*) Notice: Subject to any disclaimer, the term of this patent is extended or adjusted under 35 U.S.C. 154(b) by 65 days.

(21) Appl. No.: 13/640,111

(22) PCT Filed: Apr. 8, 2011

(86) PCT No.: PCT/CA2011/000378
§ 371 (c)(1),
(2), (4) Date: Nov. 9, 2012

(87) PCT Pub. No.: WO2011/123943
PCT Pub. Date: Oct. 13, 2011

(65) Prior Publication Data
US 2013/0053316 A1 Feb. 28, 2013

Related U.S. Application Data

(60) Provisional application No. 61/322,520, filed on Apr. 9, 2010.

(51) Int. Cl.
*A61K 38/00* (2006.01)
*A61K 38/26* (2006.01)

(52) U.S. Cl.
CPC ...................................... *A61K 38/26* (2013.01)

(58) Field of Classification Search
None
See application file for complete search history.

(56) References Cited

U.S. PATENT DOCUMENTS

| | | |
|---|---|---|
| 5,120,721 A | 6/1992 | Morimoto et al. |
| 5,188,666 A | 2/1993 | Boccardo |
| 5,424,286 A | 6/1995 | Eng |
| 5,545,618 A | 8/1996 | Buckley et al. |
| 5,614,492 A | 3/1997 | Habener |
| 5,631,224 A | 5/1997 | Efendic et al. |
| 5,670,360 A | 9/1997 | Thorens |
| 5,846,747 A | 12/1998 | Thorens et al. |
| 5,846,937 A | 12/1998 | Drucker |
| 5,863,555 A | 1/1999 | Heiber et al. |
| 5,977,071 A | 11/1999 | Galloway et al. |
| 5,981,488 A | 11/1999 | Hoffmann |
| 6,006,753 A | 12/1999 | Efendic |
| 6,051,689 A | 4/2000 | Thorens |
| 6,110,703 A | 8/2000 | Egel-Mitani et al. |
| 6,133,235 A | 10/2000 | Galloway et al. |
| 6,162,907 A | 12/2000 | Habener |
| 6,191,102 B1 | 2/2001 | DiMarchi et al. |
| 6,268,343 B1 | 7/2001 | Knudsen et al. |
| 6,271,241 B1 | 8/2001 | DeSimone et al. |
| 6,277,819 B1 | 8/2001 | Efendic |
| 6,284,725 B1 | 9/2001 | Coolidge et al. |
| 6,329,336 B1 | 12/2001 | Bridon et al. |
| 6,344,180 B1 | 2/2002 | Host et al. |
| 6,348,447 B1 * | 2/2002 | Hellstrom et al. ........... 514/11.7 |
| 6,358,924 B1 | 3/2002 | Hoffmann |
| 6,384,016 B1 | 5/2002 | Kaarsholm |
| 6,388,053 B1 | 5/2002 | Galloway et al. |
| 6,410,508 B1 | 6/2002 | Isales et al. |
| 6,506,724 B1 | 1/2003 | Hiles et al. |
| 6,528,486 B1 | 3/2003 | Larsen et al. |
| 6,541,500 B1 | 4/2003 | Schelberger et al. |
| 6,593,295 B2 | 7/2003 | Bridon et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,989,366 B2 | 1/2006 | Beeley et al. |
| 2003/0119734 A1 | 6/2003 | Flink et al. |
| 2004/0018975 A1 | 1/2004 | DiMarchi et al. |
| 2005/0267034 A1 | 12/2005 | Prickett et al. |
| 2006/0035836 A1 | 2/2006 | Coolidge et al. |
| 2009/0202494 A1 * | 8/2009 | Cruz et al. ................... 424/93.7 |

FOREIGN PATENT DOCUMENTS

| | | |
|---|---|---|
| CA | 2262647 | 2/1998 |
| CA | 2236519 | 11/1998 |
| CA | 2321700 | 12/1999 |
| EP | 0699686 A2 | 3/1996 |
| EP | 0708179 A2 | 4/1996 |
| WO | WO 87/06941 | 11/1987 |
| WO | WO 90/11296 | 10/1990 |
| WO | WO 91/11457 | 8/1991 |
| WO | WO 97/46584 | 12/1997 |
| WO | WO 98/05351 | 2/1998 |

(Continued)

OTHER PUBLICATIONS

Orholm et al, Familial occurrence of inflammatory bowel disease, The new England Journal of Medicine, 1991, vol. 324, pp. 84-88.*

(Continued)

*Primary Examiner* — Karlheinz R Skowronek
*Assistant Examiner* — Sergio Coffa
(74) *Attorney, Agent, or Firm* — Howson & Howson LLP

(57) ABSTRACT

The invention provides a method of treating a subject having, or at risk of developing, a condition in which functioning of the small or large intestine is impaired, enhancing functioning or preventing damage to the small or large intestine in a subject, or ameliorating inflammation of the small or large intestine in a subject, comprising administering to the subject a GLP-1 receptor agonist. A GLP-1 receptor agonist may also be provided in a pharmaceutically acceptable form in an amount effective to treat or prevent conditions of the small or large intestine. Further, pharmaceutical compositions are provided for the treatment or prevention of conditions of the small or large intestine comprising a GLP-1 receptor agonist, together with a pharmaceutically acceptable carrier, excipient or vehicle.

6 Claims, 32 Drawing Sheets

(56) References Cited

FOREIGN PATENT DOCUMENTS

| WO | WO 98/08871 | | 3/1998 |
|---|---|---|---|
| WO | WO 98/30231 | | 7/1998 |
| WO | WO 98/43658 | | 10/1998 |
| WO | WO 99/43341 | | 9/1999 |
| WO | WO 99/43705 | | 9/1999 |
| WO | WO 99/43706 | | 9/1999 |
| WO | WO 99/43707 | | 9/1999 |
| WO | WO 99/43708 | | 9/1999 |
| WO | WO 00/42026 | | 7/2000 |
| WO | WO 01/04156 | | 1/2001 |
| WO | WO 01/98331 | | 12/2001 |
| WO | WO 02/46227 | | 6/2002 |
| WO | WO 2008/019147 | * | 2/2008 |
| WO | WO 2008/019147 A2 | | 2/2008 |
| WO | WO 2011/047172 | | 4/2011 |

OTHER PUBLICATIONS

Baik et al, A Comprehensive Review of Inflammatory Bowel Disease Focusing on Surgical Management, J Korean Soc Coloproctol 2012;28(3):121-131.*

Inflammatory bowel disease document, U.S. Department of Health and Human Services, Office on Women's Health, http://womenshealth.gov/publications/our-publications/fact-sheet/inflammatory-bowel-disease.cfm.*

Elbrond et al, Pharmacokinetics, Pharmacodynamics, Safety, and Tolerability of a Single-Dose of NN2211, a Long-Acting Glucagon-Like Peptide 1 Derivative, in Healthy Male Subjects, Diabetes Care 25:1398-1404, 2002.*

Lin et al, Is the Role of the Small Intestine in First-Pass Metabolism Overemphasized?, Pharmacological Reviews, vol. 51, No. 2, 1999.*

Simonsen et al, Exendin-4, but not dipeptidyl peptidase IV inhibition, increases small intestinal mass in GK rats, American Journal of Physiology Gastrointestinal Liver Physiology, Jul. 2007;293(1):G288-95. Epub Apr. 12, 2007.

Chen and Drucker, Tissue-specific expression of unique mRNAs that encode proglucagon-derived peptides or exendin 4 in the lizard, Journal of Biological Chemistry, Feb. 14, 1997;272(7):4108-15.

International Search Report dated Aug. 11, 2011 issued in corresponding International Patent Application No. PCT/CA2011/000378.

Written Opinion of the International Searching Authority dated Aug. 11, 2011 issued in corresponding International Patent Application No. PCT/CA2011/000378.

Eng, J., et al., Isolation and characterization of exendin-4, an exendin-3 analogue, from Heloderma suspectum venom. Further evidence for an exendin receptor on dispersed acini from guinea pig pancreas, Journal of Biological Chemistry, 267(11):7402-05, Apr. 1992.

Drucker et al., Induction of intestinal epithelial proliferation by glucagon-like peptide 2, PNAS:USA, 93:7911-7916, Jul. 1996.

Gault VA et al, Administration of an acylated GLP-1 and GIP preparation provides added beneficial glucose-lowering and insulinotropic actions over single incretins in mice with type 2 diabetes and obesity. Clinical Science (Lond). Epub Feb. 2011.

Irwin N et al, Insulin-releasing and metabolic effects of small molecule GLP-1 receptor agonist 6,7-dichloro-2-methylsulfonyl-3-N-tert-butylaminoquinoxaline. European Journal Pharmacology, 628(1-3):268-73, Feb. 2010.

Noyan-Ashraf MH et al, GLP-1R agonist liraglutide activates cytoprotective pathways and improves outcomes after experimental myocardial infarction in mice. Diabetes, 8(4):975-83, Apr. 2009.

Porter DW et al, Four weeks administration of Liraglutide improves memory and learning as well as glycaemic control in mice with high fat dietary-induced obesity and insulin resistance. Diabetes, Obesity and Metabolism, 12(10):891-9, Oct. 2010.

Rolin B et al, The long-acting GLP-1 derivative NN2211 ameliorates glycemia and increases beta-cell mass in diabetic mice. American Journal of Physiology, Endocrinology and Metabolism. 283(4):E745-52, Oct. 2002.

Scrocchi LA, et al, Glucose intolerance but normal satiety in mice with a null mutation in the glucagon-like peptide 1 receptor gene, Nature Medicine, 2:1254-1258, Nov. 1996.

Ambrosio et al, GLP-1 receptor agonist-induced polyarthritis: a case report; Acta Diabetologica, Published online ahead of print Oct. 25, 2013.

Barbara et al, A Role for Inflammation in Irritable Bowel Syndrome?, Gut, vol. 51(supp. 1) pp. i41-i44, Jul. 2002.

Drucker, Glucagon-like Peptides: Regulators of Cell Proliferation, Differentiation, and Apoptosis, Molecular Endocrinology, vol. 17(2) pp. 161-171, Feb. 1, 2003.

Estall et al, Glucagon and Glucagon-like Peptide Receptors as Drug Targets, Current Pharma Design, Bentham Sci Pub, NL, vol. 12(14) pp. 1731-1750, Jan. 1, 2006.

Guo et al, Liraglutide prevents diabetes progression in prediabetic, OLETF rats, Endocrine Journal, Jan. 31, 2013, 60 (1), 15-28.

Hellstrom et al, Clinical Trial: the Glucagon-like Peptide-1 Analogue ROSE-010 for Management of Acute Pain in Patients with Irritable Bowel Syndrome: a Randomized, Placebo-controlled, Double-blind Study, Alimentary Pharmacology & Therapeutics, vol. 29(2) pp. 198-206, Jan. 1, 2009.

Hellstrom et al, GLP-1: Broadening the Incretin Concept to Involve Gut Motility, Regulatory Peptides, Elsevier Since BV, NL, vol. 156(1-3) pp. 9-12, Aug. 7, 2009.

Hellstrom et al, GLP-1 Suppresses Gastrointestinal Motility and Inhibits the Migrating Motor Complex in Healthy Subjects and Patients With Irritable Bowel Syndrome, Neurogastro & Motility, vol. 20(6) pp. 649-659, Jun. 1, 2008.

Pimentel et al, The Efficacy of the GLP-1 Agonist Exenatide in the Treatment of Short Bowel Syndrome, Am J of Gastro, vol. 102(suppl. 2) pp. s201-s202, Sep. 2007.

European Search Report dated Jan. 2, 2014 issued in corresponding European Patent Application No. 11764985.5.

Agerso, H. et al, The pharmacokinetics, pharmacodynamics, safety and tolerability of NN2211, a new long-acting GLP-1 derivative, in healthy men. Diabetologia, Feb. 2002; 45(2):195-202.

Degn, K.B et al, One week's treatment with the long-acting Glucagon-like Peptide 1 derivative Liraglutide (NN2211) markedly inproves 24-h Glycemia and a- and b- cell function and reduces Endogenous Glucose release in patients with type 2 Diabetes. Diabetes, May 2004; 53(5): 1187-1194.

Feinglos, M.N et al, Effects of Liraglutide (NN2211), a long-acting GLP-1 analogue, on glycemic control and bodyweight in subjects with type 2 Diabetes. Diabetic Medicine, Aug. 2005; 22(8): 1016-1023.

Horowitz, M. et al, Patient-reported rating of gastrointestinal adverse effects during treatment of type 2 diabetes with the once-daily human GLP-1 analogue, liraglutide. Diabetes, Obesity and Metabolism, Jul. 2008; 10(7): 593-596.

Madsbad, S. et al, Improved Glycemic control with no weight increase in patients with type 2 Diabetes after once-daily treatment with the long-acting Glucagon-like Peptide 1 analog Liraglutide (NN2211), Diabetes Care, Jun. 2004; 27(6): 1335-1342.

Nauck, M.A et al, Five weeks of treatment with the GLP-1 analogue Liraglutide improves Glycemic control and lowers body weight in subjects with type 2 Diabetes. Exp Clin Endocrinol Diabetes, Sep. 2006; 114(8): 417-423.

Sun, F. et al, Impact of GLP-1 receptor agonists on major gastrointestinal disorders for type 2 diabetes mellitus: a mixed treatment comparison meta-analysis. Experimental Diabetes Research, Epub, Dec. 26, 2012; Article ID 230624.

Vilsboll, T. et al, Liraglutide, a long-acting human Glucagon-like Peptide-1 analog, gives as Monotherapy significantly improves Glycemic control and lowers body weight without risk of Hypoglycemia in patients with type 2 Diabetes. Diabetes Care, Jun. 2007; 30(6):1608-1610.

Abu-Hamdah, R., et al. Clinical review: The extrapancreatic effects of glucagon-like peptide-1 and related peptides. The Journal of Clinical Endocrinology and Metabolism. vol. 94(6):1843-1852. Jun. 2009.

(56) References Cited

OTHER PUBLICATIONS

Ban, K., et al. Cardioprotective and vasodilatory actions of glucagon-like peptide 1 receptor are mediated through both glucagon-like peptide 1 receptor-dependent and- independent pathways. Circulation. vol. 117(18):2340-2350. May 6, 2008.

Ban, K., et al. GLP-1(9-36) protects cardiomyocytes and endothelial cells from ischemia-reperfusion injury via cytoprotective pathways independent of the GLP-1 receptor. Endocrinology. vol. 151(4):1520-1531. Apr. 2010.

Burgmaier, M., et al. Glucagon-like peptide-1 (GLP-1) and its split products GLP-1(9-37) and GLP-1(28-37) stabilize atherosclerotic lesions in apoe(−)/(−) mice. Atherosclerosis. vol. 231(2):427-435. Sep. 5, 2013.

Campbell, J.E., and Drucker, D.J. Pharmacology physiology and mechanisms of incretin hormone action. Cell Metabolism. vol. 17:819-837. Jun. 4, 2013.

Elahi, D., et al. GLP-1 (9-36) Amide, Cleavage Product of GLP-1 (7-36) Amide, is a Glucoregulatory Peptide. Obesity (Silver Spring). vol. 16:1501-1509. Jul. 2008.

Hopkins, N.D., et al. Effects of 6 months glucagon-like peptide-1 receptor agonist treatment on endothelial function in type 2 diabetes mellitus patients. Diabetes Obesity Metabolism. vol. 15(8):770-773. Aug. 15, 2013.

Liberman, A., Esser, M., Marx, N., and Burgmaier, M. Glucagon-like peptide-1(9-36) inhibits chemokine-induced migration of human CD4-positive lymphocytes. PLoS One. vol. 8(3):e58445. Mar. 2013.

Marx, N., et al. Glucagon-like peptide-1(1-37) inhibits chemokine-induced migration of human CD4-positive lymphocytes. Cell Molecular Life Science. vol. 67(20):3549-3555. Oct. 2010.

Nystrom, T., et al. Effects of glucagon-like peptide-1 on endothelial function in type 2 diabetes patients with stable coronary artery disease. American Journal Physiology Endocrinology Metabolism vol. 287:E1209-1215. Sep. 7, 2004.

Taing MW., et al. GLP-1(28-36)amide, the Glucagon-like peptide-1 metabolite: friend, foe, or pharmacological folly? Drug Design, Development and Therapy. vol. 8:677-688. Jun. 3, 2014.

Tomas, E., Stanojevic, V., and Habener, J.F. GLP-1 (9-36) amide metabolite suppression of glucose production in isolated mouse hepatocytes. Hormone and metabolic research. vol. 42(9):657-662. Aug. 2010.

Tomas, E., Stanojevic, V., and Habener, J.F. GLP-1-derived nonapeptide GLP-1(28-36) amide targets to mitochondria and suppresses glucose production and oxidative stress in isolated mouse hepatocytes. Regulatory Peptides. vol. 167(2-3):177-184. Apr. 11, 2011.

Tomas, E., Wood, J.A., Stanojevic, V., and Habener, J.F. 2011. Glucagon-like peptide-1(9-36)amide metabolite inhibits weight gain and attenuates diabetes and hepatic steatosis in diet-induced obese mice. Diabetes, Obesity & Metabolism. vol. 13(1):26-33. Jan. 2011.

Ussher, J., and Drucker D.J., Cardiovascular actions of incretin-based therapies. Circulatory Research. vol. 114(11):1788-1803. May 23, 2014.

Response to the European Search Report of Jan. 2, 2014 issued in corresponding European Patent Application No. 11764985.5, dated Jul. 22, 2014.

* cited by examiner

A

B

A

B

A

B

*, p<0.05 vs PBS qd

A

B (C)

(D)

(A)

(B)

(C)

(D)

N=9-12 mice/group

N=4 mice/group

A

Colon Length

B

Colon Weight

C

Colon Weight/BW

N=4 mice/group

A

B

N=4 mice/group

C

D

N=4 mice/group

N=4 mice/group

A

B

C

D

A

B

A

B

C

D

Final Body Wt

A

B

C

D

E

F

G

H

A

B

C

D

E

A

B

SEQUENCE LISTING

<160> NUMBER OF SEQ ID NOS: 6

<210> SEQ ID NO 1
<211> LENGTH: 36
<212> TYPE: PRT
<213> ORGANISM: Homo sapiens

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg
            35

<210> SEQ ID NO 2
<211> LENGTH: 37
<212> TYPE: PRT
<213> ORGANISM: Homo sapiens

<400> SEQUENCE: 2

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
            35

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 39
<212> TYPE: PRT
<213> ORGANISM: Heloderma horridum

```
<400> SEQUENCE: 5

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 6
<211> LENGTH: 39
<212> TYPE: PRT
<213> ORGANISM: Heloderma suspectum

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```

METHODS FOR TREATING DISORDERS OF THE GASTROINTESTINAL TRACT USING A GLP-1 AGONIST

CROSS-REFERENCE TO RELATED APPLICATIONS

This application is a national stage of International Patent Application No. PCT/CA2011/000378, filed Apr. 8, 2011, which claims the benefit of the priority of U.S. Provisional Patent Application No. 61/322,520, filed Apr. 9, 2010 (expired), which applications are incorporated herein by reference.

FIELD OF THE INVENTION

This invention relates to glucagon-like peptide-1 receptor agonists and their use for the prevention or treatment of disorders involving the gastrointestinal tract.

BACKGROUND OF THE INVENTION

Inflammation of the intestinal tract is one of the most common types of inflammatory processes affecting humans. Inflammatory bowel disease (IBD) is a group of serious chronic gastrointestinal inflammatory disorders of generally unknown etiology. The two most common forms of IBD are ulcerative colitis (UC) and Crohn's disease (CD). Ulcerative colitis affects the small or large intestine and involves the inner lining (e.g., the mucosal and sub-mucosal layer) of the intestinal wall. Crohn's disease may affect any section of the gastrointestinal tract and may involve all layers of the intestinal wall. Symptoms of IBD include rectal and/or intestinal bleeding, abdominal pain and cramping, diarrhea, and weight loss.

IBD remains relatively resistant to current treatments. Current therapies are primarily directed at reducing the inflammatory process and its detrimental effects, and include administration of anti-inflammatory drugs (e.g., mesalamine, suifasalazine, infliximab, adalimumab, prednisone, budesonide) and immunosuppressive drugs (e.g., 6-mercaptopurine, azathioprine, cyclosporine). These therapies may be associated with severe adverse side effects including anorexia, dyspepsia, malaise, headaches, abdominal pain, fever, rash, pancreatitis, bone marrow suppression, and infections. Invasive surgical procedures, including colectomy, proctocolectomy, and ileostomy, are also used when drug therapies fail.

U.S. Pat. No. 6,297,214 discloses the use of glucagon-like peptide 2 (GLP-2) to treat or prevent inflammatory conditions of the small or large intestine. U.S. Pat. No. 6,348,447 discloses the use of a gastrointestinal peptide hormone selected from the class consisting of glucagon-like peptide-1 (GLP-1) and derivatives thereof having anti-secretory effects and smooth muscle relaxatory properties in the gastrointestinal tract for the treatment of functional dyspepsia and/or irritable bowel syndrome.

SUMMARY OF THE INVENTION

The invention is based, in part, on the finding that GLP-1 receptor agonists act to enhance functioning of the small or large intestine. In particular, it has been demonstrated that peptidic hormones that activate the GLP-1 receptor, including without limitation GLP-1 and analogs thereof, can increase the mass and/or length of the small or large intestine. Thus, the GLP-1 receptor agonists may be suitable for the regeneration and/or repair of colonic tissue. In particular, they may be used to promote healing of the lining of the large bowel epithelium.

It has also been demonstrated that lower doses of GLP-1 receptor agonists which are generally used to reduce blood glucose or body weight, or less frequent once daily administration regimens of GLP-1 receptor agonists that do not significantly lower blood glucose or body weight, continue to produce significant effects on the gastrointestinal tract. The gastrointestinal tract was found to be more sensitive to the effects of GLP-1 receptor agonists at the lower doses used compared to the doses required to produces changes in the brain or pancreas. Lower doses of GLP-1 receptor agonists can still exert therapeutic effects on the gut, yet reduce or eliminate some of the unwanted side effects experienced with higher doses, including without limitation, nausea, vomiting, glucose reduction, hypoglycemia, and/or weight loss.

The invention provides a method of i) treating a subject having, or at risk of developing, a condition in which functioning of the small or large intestine is impaired, ii) enhancing functioning or preventing damage to the small or large intestine in a subject, or iii) ameliorating inflammation of the small or large intestine in a subject, comprising administering to the subject a GLP-1 receptor agonist.

The invention also provides a method for treating a subject having, or at risk of developing, a condition in which functioning of the small or large intestine is impaired or to enhance functioning of the small or large intestine, comprising the step of delivering to the small or large intestine of the subject a GLP-1 receptor agonist in an amount effective to ameliorate said condition or the onset thereof.

The invention also provides a method of treating a subject having, or at risk of developing, a condition ameliorated by enhanced growth of the small or large intestine to proliferate the tissue of the small or large intestine, comprising the step of delivering to the small or large intestine of the subject a GLP-1 receptor agonist, in an amount effective to proliferate the tissue of the small or large intestine.

In one aspect, the invention provides a method of proliferating the small or large intestine in a subject in need thereof comprising delivering to the small or large intestine of the subject a small or large intestine proliferating amount of a GLP-1 receptor agonist.

In one aspect, the invention provides a method of delivering to the small intestine of a patient in need thereof, a pharmaceutically effective amount of a GLP-1 receptor agonist, wherein the length or weight of the small intestine is increased.

More particularly, and according to one aspect of the invention, there is provided a method of treating a subject having an inflammatory condition involving the small or large intestine, wherein a GLP-1 receptor agonist is delivered to the small or large intestine in an amount capable of ameliorating inflammation of the small or large intestine. In a related aspect of the invention, there is provided a method of treating a subject having an inflamed small or large intestine comprising the step of delivering to the subject a small or large intestine inflammation ameliorating amount of a GLP-1 receptor agonist in a pharmaceutically acceptable carrier, excipient or vehicle. In a further aspect, a GLP-1 receptor agonist is provided in a pharmaceutically acceptable form in an amount effective to cause proliferation of the small or large intestine. In a further aspect, a GLP-1 receptor agonist is provided in a pharmaceutically acceptable form in an amount effective to cause proliferation of, i.e., increase the weight or length of, the small intestine.

According to an aspect of the invention, there is provided a method of treating a subject having an inflammatory condition involving the small or large intestine, wherein a GLP-1 receptor agonist is delivered to the small or large intestine in an amount capable of ameliorating inflammation of the small or large intestine and reducing or eliminating any side effects associated with the GLP-1 receptor agonist. In an aspect of the invention, there is provided a method of treating a subject having an inflamed small or large intestine comprising the step of delivering to the subject a small or large intestine inflammation ameliorating amount of a GLP-1 receptor agonist in a pharmaceutically acceptable carrier, excipient or vehicle, wherein any side effects associated with the GLP-1 receptor agonist are reduced or eliminated.

In an aspect, the invention provides a method of regenerating and/or repairing colonic tissue in a subject comprising administering to the subject an effective amount of a GLP-1 receptor agonist.

In an aspect of the invention, a GLP-1 receptor agonist is administered to prevent further damage to the small or large intestine to individuals at risk of developing intestinal inflammation, or to individuals exhibiting early or active signs of intestinal inflammation.

In an aspect, the invention provides a method for the treatment of IBD in a human patient suffering therefrom comprising administering to the patient an effective amount of at least one GLP-1 receptor agonist having proliferative and/or anti-inflammatory effects in the small or large intestine and/or regenerative effects in the colonic tissue.

In another aspect, the invention provides a method of prophylactically treating a subject at risk of developing an inflammatory condition involving the small or large intestine comprising the steps of:
  a) identifying a subject at risk of developing an inflammatory condition involving the small or large intestine; and
  b) administering to the subject an amount of a GLP-1 receptor agonist effective to inhibit or delay or prevent the onset of the inflammatory condition.

In embodiments of the invention, the amount delivered or administered to the subject is effective to treat or ameliorate a condition disclosed herein or the onset thereof, proliferate, repair, or prevent damage to the tissue of the small or small or large intestine, and/or ameliorate inflammation of the small or large intestine, without significantly lowering blood glucose and/or body weight of the subject. In embodiments of the invention, the amount delivered or administered to the subject is effective to reduce or eliminate side effects associated with a GLP-1 receptor agonist. The side effects of a GLP-1 receptor agonist include but are not limited to nausea, vomiting, glucose reduction, hypoglycemia, and/or weight loss.

In an aspect, the invention provides a pharmaceutical composition for use in treating an inflammatory condition involving the small or large intestine comprising a GLP-1 receptor agonist and a pharmaceutically acceptable carrier, excipient or vehicle.

In an aspect, the invention provides a pharmaceutical composition for use in treating an inflammatory condition involving the small or large intestine comprising an amount of GLP-1 receptor agonist effective to ameliorate inflammation of the small or large intestine or cause proliferation of the small or large intestine, and a pharmaceutically acceptable carrier, excipient or vehicle.

In an aspect, the invention provides a pharmaceutical composition for use in treating an inflammatory condition involving the small or large intestine comprising an amount of GLP-1 receptor agonist effective to ameliorate inflammation of the small or large intestine or cause proliferation of the small or large intestine without significantly lowering blood glucose and/or body weight of the subject, and a pharmaceutically acceptable carrier, excipient or vehicle.

In an aspect, the invention provides a pharmaceutical composition for use in treating an inflammatory condition involving the small or large intestine comprising an amount of GLP-1 receptor agonist effective to ameliorate inflammation of the small or large intestine or cause proliferation of the small or large intestine without significantly lowering blood glucose and/or body weight of the subject, and a pharmaceutically acceptable carrier, excipient or vehicle.

In an aspect, the invention provides a pharmaceutical composition for use in treating an inflammatory condition involving the small or large intestine comprising an amount of GLP-1 receptor agonist effective to ameliorate inflammation of the small or large intestine or cause proliferation of the small or large intestine and reduce or eliminate any side effects of the GLP-1 receptor agonist, and a pharmaceutically acceptable carrier, excipient or vehicle.

In an aspect, the invention provides a pharmaceutical composition for the treatment of IBD comprising a GLP-1 receptor agonist, in particular an exendin-4, having proliferative and/or anti-inflammatory effects in the small or large intestine, together with a pharmaceutically acceptable carrier, excipient or vehicle.

In an aspect, the invention provides a pharmaceutical composition for the treatment of IBD comprising a GLP-1 receptor agonist, in particular an exendin-4, having regenerative effects in the colonic tissue, together with a pharmaceutically acceptable carrier, excipient or vehicle.

In another aspect of the invention, there is provided a method to identify peptides useful to treat inflammatory conditions involving the small or large intestine comprising the steps of:
  a) obtaining a GLP-1 receptor agonist, in particular an analog of a vertebrate GLP-1 peptide or an exendin, the analog having at least one amino acid substitution, deletion, addition, or inversion or an amino acid with a blocking group;
  b) inducing an inflammatory condition of the intestine involving the small or large intestine in a test animal;
  c) treating the test animal having an induced inflammatory condition of the small or large intestine with the agonist using a regimen capable of eliciting an amelioration of the inflammatory condition of the small or large intestine when utilized for a human GLP-1; and
  d) determining the effect of the agonist on the health status or mortality of the test animal compared with control animals not receiving the analog or determining the mass or length or histological appearance of the small or large intestine of test animals compared to control animals not receiving an agonist.

In a related aspect of the invention, there is provided a method useful to identify GLP-1 receptor agonists capable of proliferating or healing the tissue of the small or large intestine comprising the steps of:
  a) obtaining a GLP-1 receptor agonist, in particular an analog of a vertebrate GLP-1 peptide or an exendin, the analog having at least one amino acid substitution, deletion, addition, or an amino acid with a blocking group;
  b) delivering the agonist to the small or large intestine of the test animal using a regimen capable of proliferating the small or large intestine when utilized for human GLP-1; and
  c) assessing the increase in the mass or length of the small or large intestine after completion of the treatment regime.

In another aspect of the invention, there is provided a method to identify GLP-1 receptor agonists, in particular analogs or derivatives of a GLP-1 peptide or an exendin, useful to treat inflammatory conditions involving the small or large intestine comprising the steps of:
   a) obtaining a GLP-1 receptor agonist, in particular an analog or derivative of a GLP-1 peptide or an exendin;
   b) inducing an inflammatory condition of the intestine involving the small or large intestine in a test animal;
   c) treating the test animal having an induced inflammatory condition of the small or large intestine with the agonist using a regimen capable of eliciting an amelioration of the inflammatory condition of the small or large intestine when utilized for a human GLP-1; and
   d) determining the effect of the agonist on the health status or mortality of the test animal compared with control animals not receiving the agonist or determining the mass or length or histological appearance of the small or large intestine of test animals compared to control animals not receiving the agonist.

In a related aspect of the invention, there is provided a method useful to identify GLP-1 receptor agonists, in particular analogs or derivatives of a GLP-1 peptide or an exendin, capable of proliferating the tissue of the small or large intestine comprising the steps of:
   a) obtaining a GLP-1 receptor agonist, in particular an analog or derivative of a GLP-1 peptide;
   b) delivering the agonist to the small or large intestine of the test animal using a regimen capable of proliferating the small or large intestine when utilized for human GLP-1; and
   c) assessing the increase in the mass or length of the small or large intestine after completion of the treatment regime.

In another aspect, the invention provides a method for growing small or large intestine tissue or cells there from, which comprises the step of culturing the tissue or cells in a culturing medium supplemented with a growth promoting amount of a GLP-1 receptor agonist. The tissues or cells may be used for testing putative therapeutics for enhancing function of the small or large intestine, or for transplantation into a subject. In another aspect, the invention provides a method to prevent cell death and injury in the small or large intestine.

In another aspect, the invention provides a GLP-1R agonist for use in treating any gastrointestinal disorder, particularly those described herein. In another aspect the invention provides a low dose of GLP-1R agonist for use in treating any gastrointestinal disorder, particularly those described herein.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this Detailed Description.

DESCRIPTION OF THE DRAWINGS

The invention will now be described in relation to the drawings in which.

Figure 1:
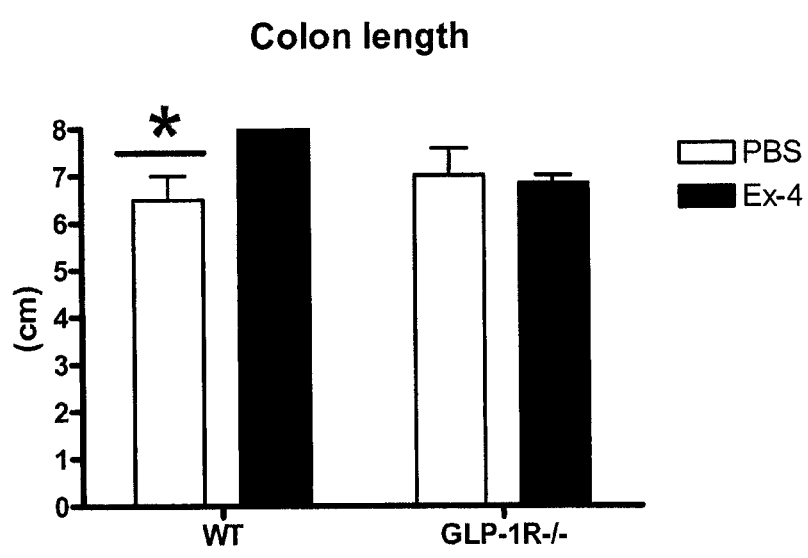
FIGS. 1A and 1B are graphs of colon length and colon weight, respectively, showing data from WT and GLP-1R knockout mice treated with the GLP-1 receptor agonist Exendin-4. Mice were given intraperitoneal (i.p.) injections of phosphate buffered saline (PBS) (white bars) or 1 μg of Exendin-4 (Ex-4) (dissolved in PBS) (black bars) for 10 days. See protocol in Example 1.
Figure 1:
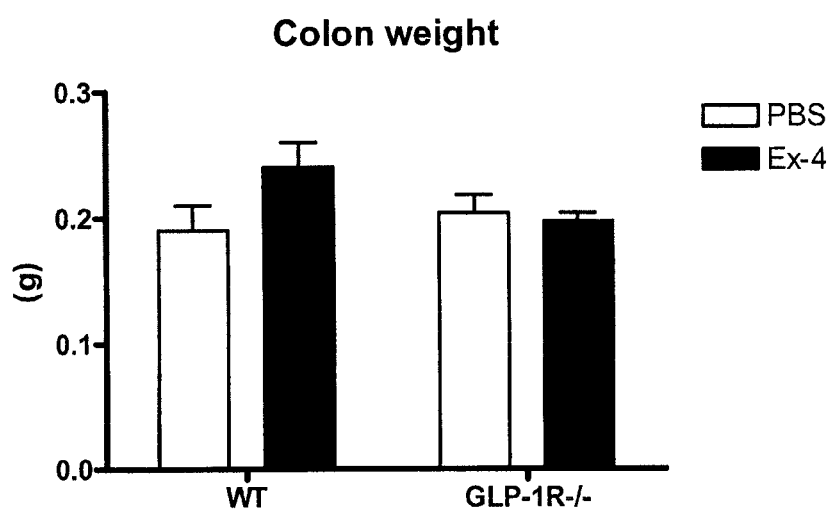

For FIGS. 3-7, the following four groups of 10-week old WT female mice on the C57B1/6 genetic background were included in the study:
   (i) PBS qd—this group was given ip injections of 100 μl of phosphate buffered saline (PBS) once per day for 14 days
   (ii) LG qd 1—this group was given ip injections of 100 μl of PBS once per day for 7 days and then 75 μg/kg of Liraglutide (LG) once per day for 7 days
   (iii) LG qd 2—this group was given ip injections of 75 μg/kg of Liraglutide (LG) once per day for 14 days
   (iv) Ex qd 2—this group was given ip injections of 10 nmol/kg of Exendin-4 (Ex) once per day for 14 days.
See Example 3 for protocol.

FIGS. 3A and 3B are graphs showing average daily body weight and average final body weight respectively per treatment groups receiving PBS, liraglutide or exendin-4. FIG. 3A depicts the average daily body weight per treatment group in grams (g). PBS qd mice are represented by a black line with open circles. LG qd 1 mice are represented by a grey line with closed grey circles. LG qd 2 mice are represented by a lighter grey line with closed grey circles. Ex qd 2 mice are represented by a black line with closed black circles.

FIG. 3B depicts the average body weight per treatment group on the day of sacrifice. (g=grams). PBS qd mice are represented by a white bar. LG qd 1 mice are represented by a medium grey bar. LG qd 2 mice are represented by the lightest grey bar. Ex qd 2 mice are represented by the darkest grey bar.

FIG. 4A depicts the average percent change in non-fasting blood glucose level from baseline level (day 1) per treatment group receiving PBS, liraglutide or exendin-4. PBS qd mice are represented by a black line with open circles. LG qd 1 mice are represented by a grey line with closed grey circles. LG qd 2 mice are represented by a lighter grey line with closed grey circles. Ex qd 2 mice are represented by a black line with closed black circles.

FIG. 4B depicts the average non-fasting blood glucose level per treatment group on the day of sacrifice (mM=millimolar). PBS qd mice are represented by a white bar. LG qd 1 mice are represented by a medium grey bar. LG qd 2 mice are represented by the lightest grey bar. Ex qd 2 mice are represented by the darkest grey bar.

FIGS. 5A and 5B are graphs showing the average weight of the total pancreas per treatment group receiving PBS, liraglutide or exendin-4 and average per treatment group of the weight of the total pancreas per gram of total body weight, respectively. FIG. 5A depicts the average weight of the total pancreas per treatment group. FIG. 5B depicts the average, per treatment group, of the weight of the total pancreas per gram of total body weight (g=grams). For FIGS. 5A and 5B, PBS qd mice are represented by a white bar. LG qd 1 mice are represented by a medium grey bar. LG qd 2 mice are represented by the lightest grey bar. Ex qd 2 mice are represented by the darkest grey bar. FIGS. 6A-6D are graphs showing the average weight of the entire small bowel per treatment group receiving PBS, liraglutide or exendin-4 (A); average per treatment group of the weight of the entire small bowel per gram of the total body weight (B); average length of the entire small bowel per treatment group (C); and, average per treatment group of the weight of the small bowel per unit of small bowel length (D).

For FIGS. 6A-6D, PBS qd mice are represented by a white bar. LG qd 1 mice are represented by a medium grey bar. LG qd 2 mice are represented by the lightest grey bar. Ex qd 2 mice are represented by the darkest grey bar.

FIGS. 7A-7D are graphs showing the average weight of the entire colon per treatment group receiving PBS, liraglutide or exendin-4 (A); average per treatment group of the weight of the entire colon per gram of total body weight (B); average length of the entire colon per treatment group (C); and average, per treatment group, of the weight of the colon per unit of colon length (D). g=grams, cm=centimeters. For FIGS. 7A-7D, PBS qd mice are represented by a white bar. LG qd 1 mice are represented by a medium grey bar. LG qd 2 mice are represented by the lightest grey bar. Ex qd 2 mice are represented by the darkest grey bar.

Figure 8:
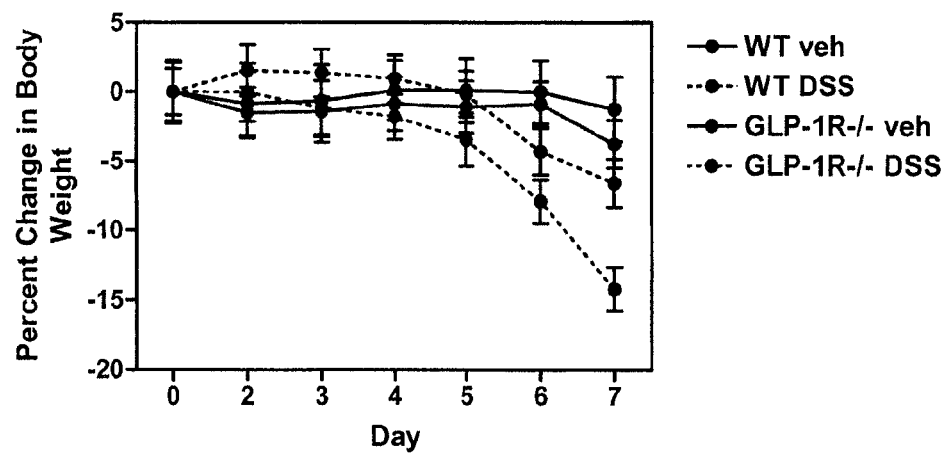
Figure 8:
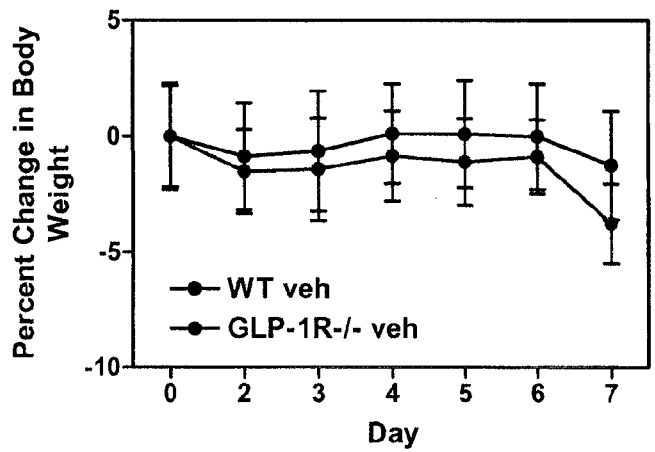
Figure 8:
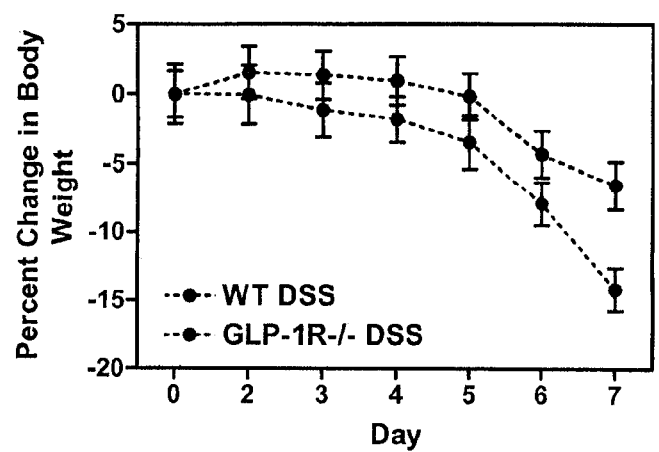

FIGS. 8A-8C are graphs showing that GLP-1R−/− mice lose more weight than wild type mice during dextran sodium sulfate (DSS) treatment. For FIGS. 8A-8C, wild type mice fed regular drinking water (WT veh) are represented by a solid black line, wild type mice fed water supplemented with 3% DSS (WT DSS) are represented by a dashed black line, GLP-1R−/− mice fed regular drinking water (GLP-1R−/− veh) are represented by a solid dark grey line, and GLP-1R−/− mice fed drinking water supplemented with 3% DSS (GLP-1R−/− DSS) are represented by a dashed dark grey line. See Example 4 for protocol.

Figure 9:
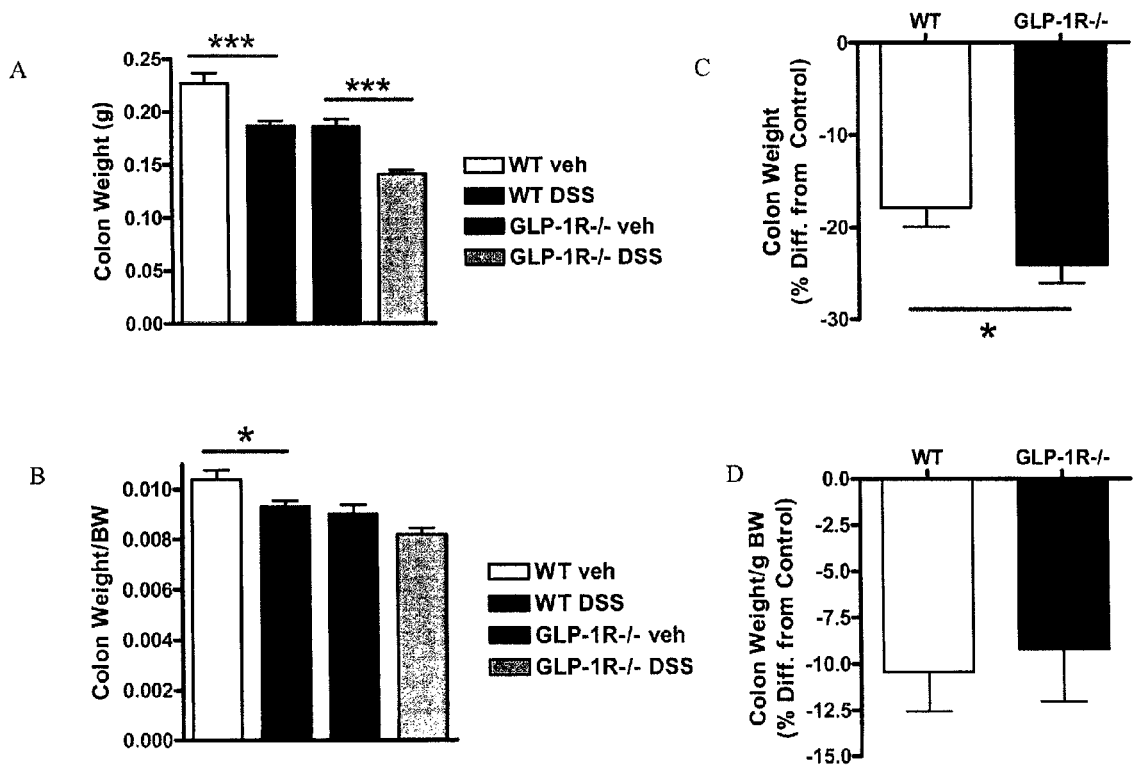

FIGS. 9A-9D are graphs showing colon weight is reduced to a greater degree in GLP-1R−/− mice during DSS treatment. See Example 4 for protocol. FIG. 9A shows the average colon weight for each group of mice. FIG. 9B shows the average colon weight per gram total body weight for each group of mice. For FIGS. 9A and 9B, wild type mice fed regular drinking water are represented by a white bar, wild type mice fed water supplemented with 3% DSS are represented by a black bar, GLP-1R−/− mice fed regular drinking water are represented by a dark grey bar, and GLP-1R−/− mice fed drinking water supplemented with 3% DSS are represented by a light grey bar. FIG. 9C shows the percent difference in colon weight between DSS fed mice and regular drinking water fed mice. Wild type mice are represented by a white bar. GLP-1R−/− mice are represented by a black bar. FIG. 9D shows the percent difference in colon weight per gram total body weight between DSS fed mice and regular drinking water fed mice. Wild type mice are represented by a white bar. GLP-1R−/− mice are represented by a black bar.

Figure 10:
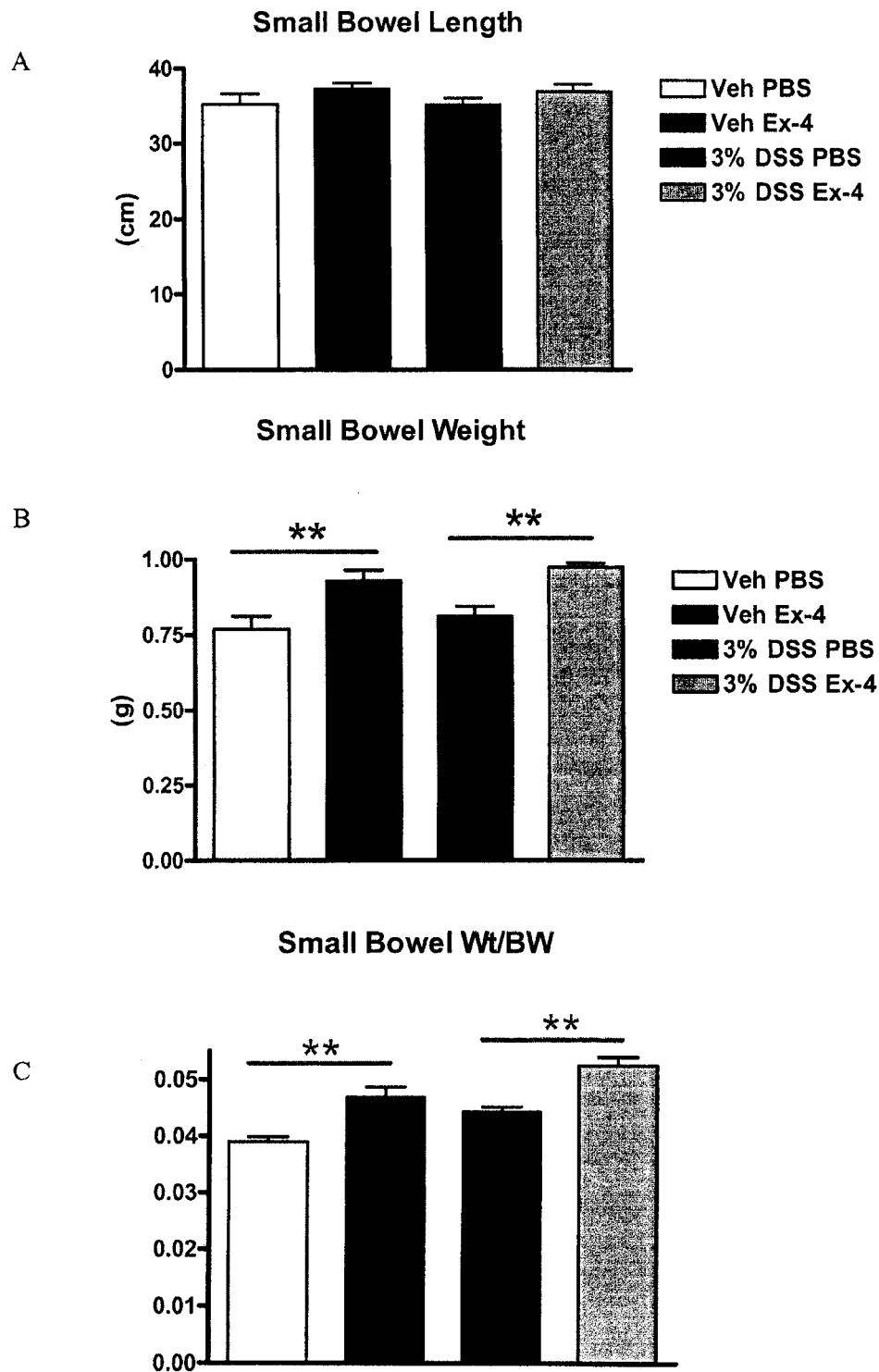

FIGS. 10A-10C are graphs showing the GLP-1R agonist exendin-4 increases small bowel size in mice maintained on water with or without DSS. See Example 4 for protocol. For FIGS. 10A-10C, the bars are identified as follows: mice fed regular drinking water and given injections of PBS are represented by white bars. Mice fed regular drinking water and given injections of Ex-4 are represented by dark grey bars. Mice fed water supplemented with 3% DSS and given injections of PBS are represented by black bars. Mice fed water supplemented with 3% DSS and given injections of Ex-4 are represented by light grey bars.

Figure 11:
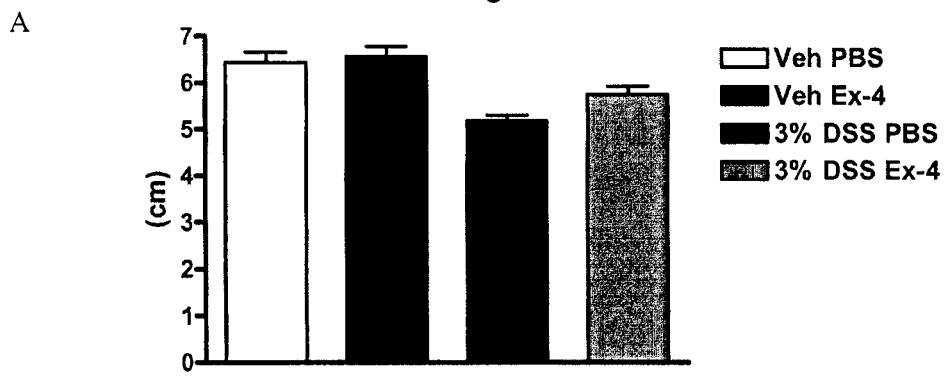
Figure 11:
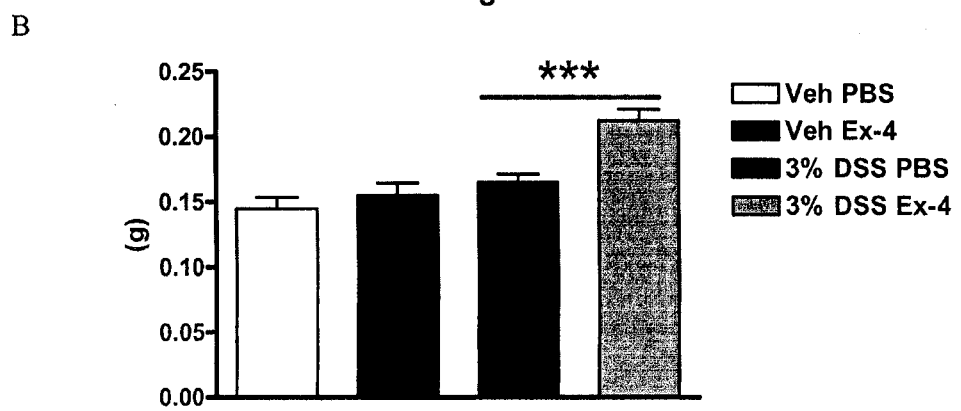
Figure 11:
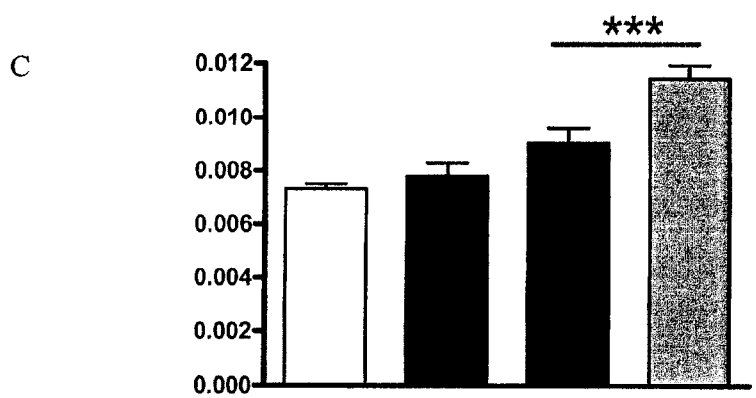

FIGS. 11A-11C are graphs showing the GLP-1R agonist exendin-4 increases colon weight in DSS-treated mice. See Example 4 for protocol. For FIGS. 11A-11C, mice fed regular drinking water and given injections of PBS are represented by white bars. Mice fed regular drinking water and given injections of Ex-4 are represented by dark grey bars. Mice fed water supplemented with 3% DSS and given injections of PBS are represented by black bars. Mice fed water supplemented with 3% DSS and given injections of Ex-4 are represented by light grey bars.

Figure 12:
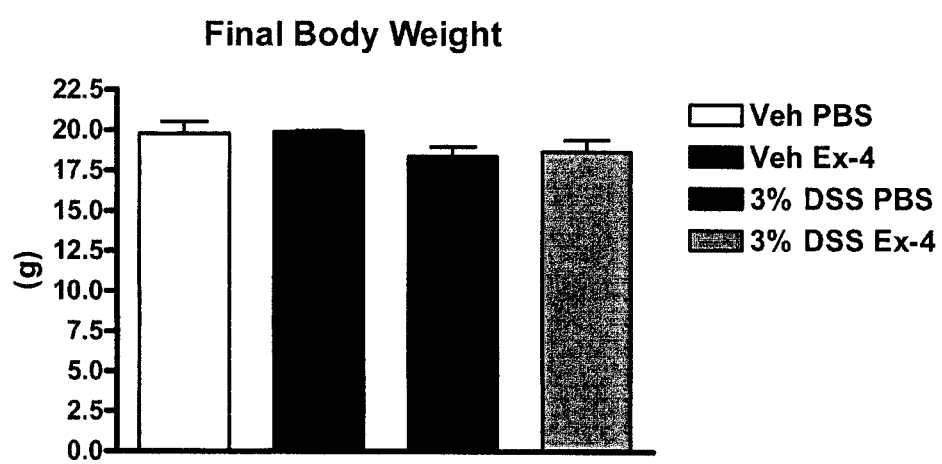
Figure 12:
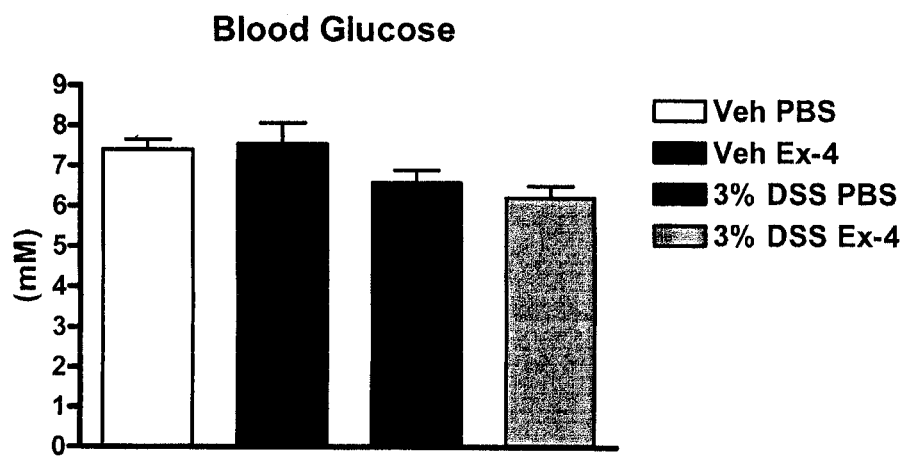

FIGS. 12A and 12B are graphs showing that there is no difference in final body weight or blood glucose levels in exendin-4 treated versus PBS treated mice. See Example 4 for protocol. For FIGS. 12A and 12B, mice fed regular drinking water and given injections of PBS are represented by white bars. Mice fed regular drinking water and given injections of Ex-4 are represented by dark grey bars. Mice fed water supplemented with 3% DSS and given injections of PBS are represented by black bars. Mice fed water supplemented with 3% DSS and given injections of Ex-4 are represented by light grey bars.

FIGS. 13A and 13B are graphs showing that there is no difference in final body weight or blood glucose levels in mice treated with the GLP-1R agonist liraglutide (LG) versus PBS-treated mice. See Example 4 for protocol. For FIGS. 13A and 13B: Mice fed regular drinking water and given injections of PBS are represented by white bars. Mice fed regular drinking water and given injections of LG are represented by dark grey bars. Mice fed water supplemented with 3% DSS and given injections of PBS are represented by black bars. Mice fed water supplemented with 3% DSS and given injections of LG are represented by light grey bars.

FIGS. 14A-14D are graphs showing that liraglutide increases small bowel size in mice maintained on water with or without DSS. See Example 4 for protocol. For FIGS. 14A-14D: Mice fed regular drinking water and given injections of PBS are represented by white bars. Mice fed regular drinking water and given injections of LG are represented by dark grey bars. Mice fed water supplemented with 3% DSS and given injections of PBS are represented by black bars. Mice fed water supplemented with 3% DSS and given injections of LG are represented by light grey bars.

FIGS. 15A-15D are graphs showing that liraglutide increases colon weight in mice maintained on water. See Example 4 for protocol. For FIGS. 15A-15D: Mice fed regular drinking water and given injections of PBS are represented by white bars. Mice fed regular drinking water and given injections of LG are represented by dark grey bars. Mice fed water supplemented with 3% DSS and given injections of PBS are represented by black bars. Mice fed water supplemented with 3% DSS and given injections of LG are represented by light grey bars.

FIGS. 16A-16D are graphs showing that doses of liraglutide lower than those that have shown glucose lowering or cardioprotective effects in rodents are able to increase small intestine size (small intestine weight and length) in wild type mice compared to PBS-treated mice. See Example 5 for protocol. For FIGS. 16A-16D: Mice fed regular drinking water and given injections of PBS are represented by white bars. Mice fed regular drinking water and given 25 µg/kg of Liraglutide (LG) BID are represented by dark grey bars. Mice fed regular drinking water and given 50 µg/kg of Liraglutide (LG) BID are represented by light grey bars. Mice fed water supplemented with 3% DSS and given injections of PBS are represented by white bars with hatch marks. Mice fed water supplemented with 3% DSS and given 25 µg/kg of Liraglutide (LG) BID are represented by dark grey bars with hatch marks. Mice fed water supplemented with 3% DSS and given 50 µg/kg of Liraglutide (LG) BID are represented by light grey bars with diagonal lines. *, , * represent $p<0.05$, 0.01 and 0.001, respectively, for Liraglutide-versus PBS-treated wild-type mice maintained on regular drinking water. #, ##, ### represent $p<0.05$, 0.01 and 0.001, respectively, for Liraglutide-versus PBS-treated wild-type mice maintained on drinking water supplemented with 3% DSS. n=5 mice/group.

Figure 17:
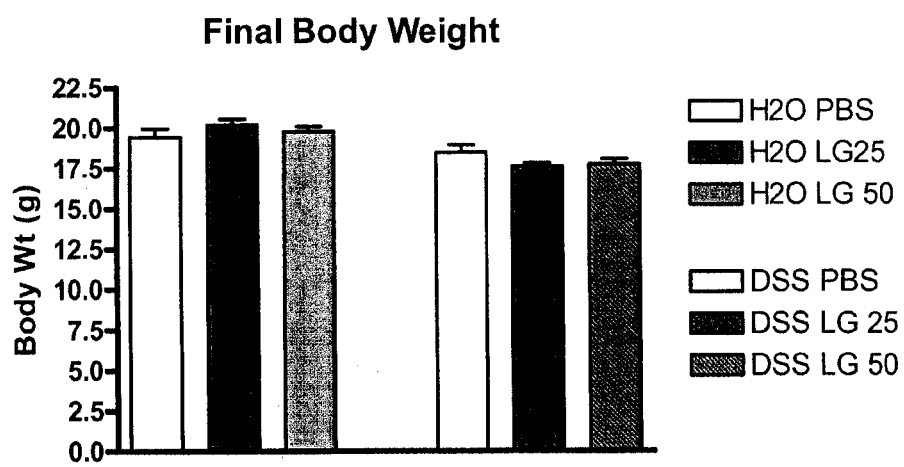
Figure 17:
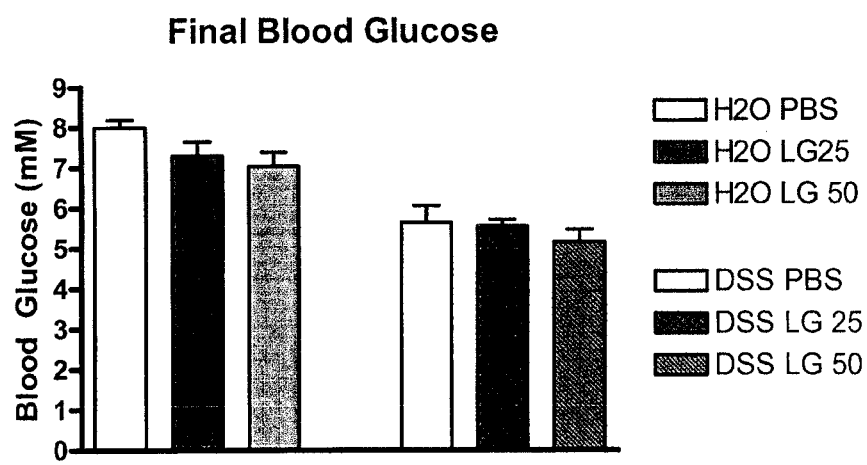
Figure 18:
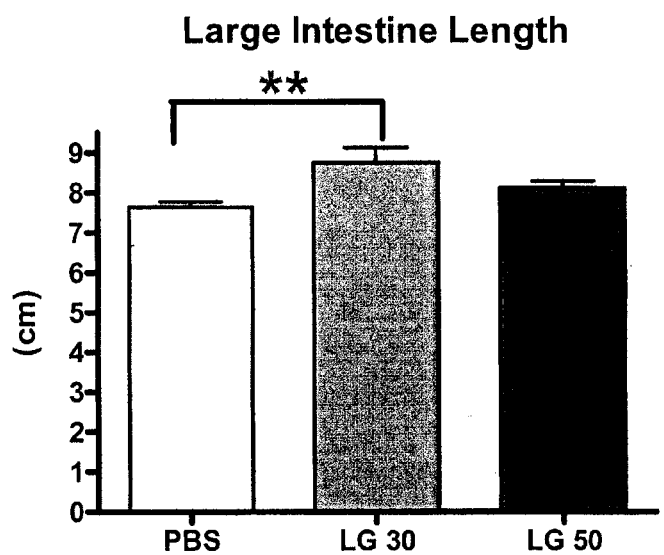
Figure 18:
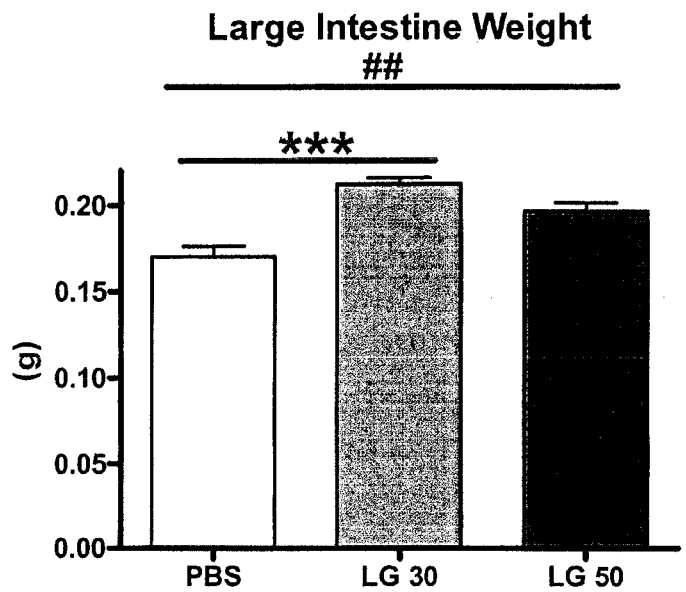
Figure 18:
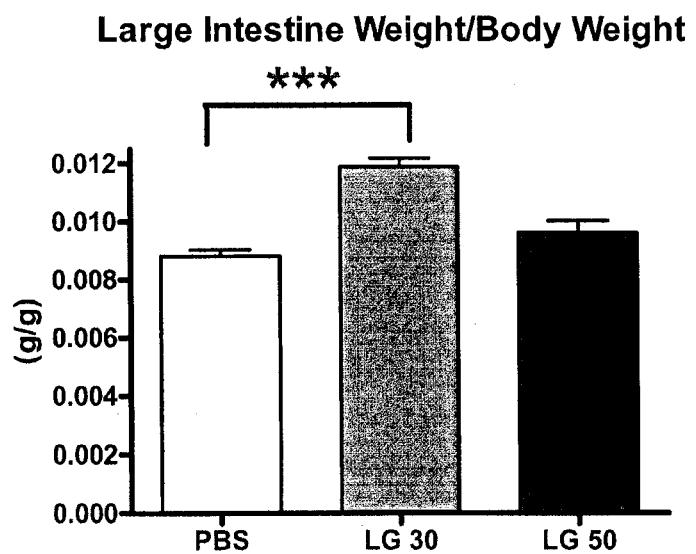
Figure 18:
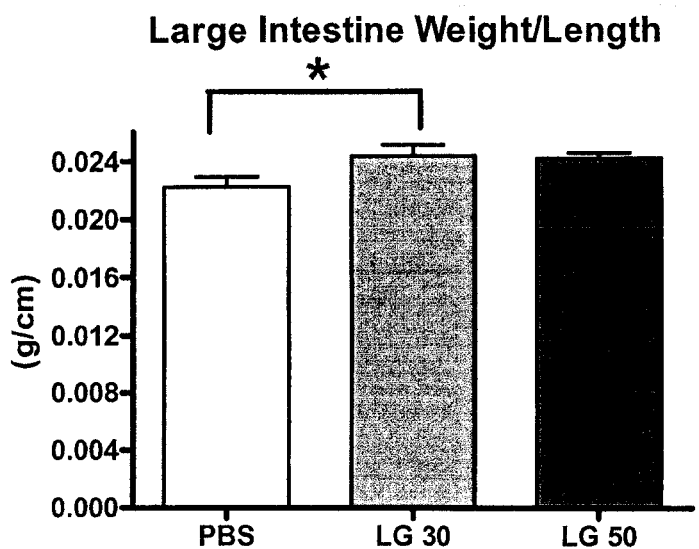

FIGS. 17A and 17B are graphs illustrating that there is no difference in final body weight or blood glucose level in wild-type mice treated with two different doses of liraglutide compared to PBS-treated mice. See Example 5 for protocol. For FIGS. 17A and 17B: Mice fed regular drinking water and given injections of PBS are represented by white bars. Mice fed regular drinking water and given 25 μg/kg of Liraglutide (LG) BID are represented by dark grey bars. Mice fed regular drinking water and given 50 μg/kg of Liraglutide (LG) BID are represented by light grey bars. Mice fed water supplemented with 3% DSS and given injections of PBS are represented by white bars with hatch marks. Mice fed water supplemented with 3% DSS and given 25 μg/kg of Liraglutide (LG) BID are represented by dark grey bars with hatch marks. Mice fed water supplemented with 3% DSS and given 50 μg/kg of Liraglutide (LG) BID are represented by light grey bars with diagonal lines.

FIGS. 18A-18D are graphs illustrating that doses of liraglutide lower than those that have shown glucose lowering or cardioprotective effects in rodents are able to increase large intestine size (large intestine weight and length) in wild type mice on the Balb/c genetic background, compared to PBS-treated mice. See Example 5 for protocol. For FIGS. 18A-18D: Mice given injections of PBS are represented by white bars. Mice given 30 μg/kg of Liraglutide (LG) BID are represented by light grey bars. Mice given 50 μg/kg of Liraglutide (LG) BID are represented by dark grey bars. *, , * represent $p<0.05$, 0.01 and 0.001, respectively, for Liraglutide (30 μg/kg BID)—versus PBS-treated mice. ## represents $p<0.01$ for Liraglutide (50 μg/kg BID) versus PBS-treated mice. n=5 mice/group.

Figure 19:
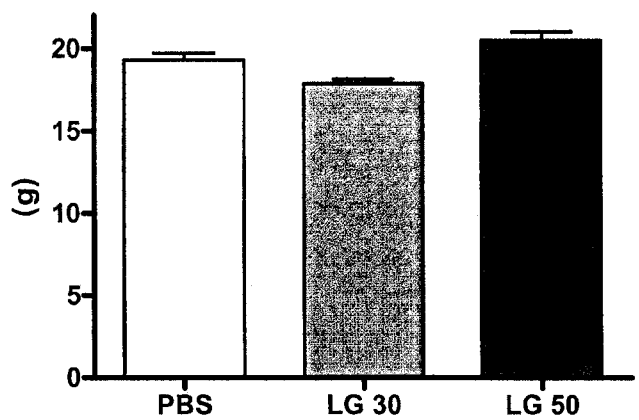

FIG. 19 is a graph illustrating that there is no difference in final body weight in wild-type mice on the Balb/c genetic background treated with two different doses of liraglutide compared to PBS-treated mice. See Example 5 for protocol. Mice given injections of PBS are represented by a white bar. Mice given 30 μg/kg of Liraglutide (LG) BID are represented by a light grey bar. Mice given 50 μg/kg of Liraglutide (LG) BID are represented by a dark grey bar.

Figure 20:
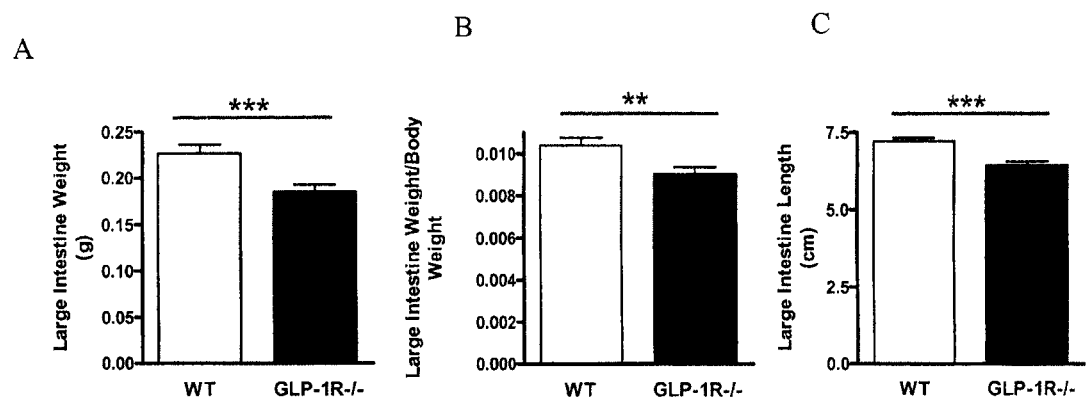
Figure 21:
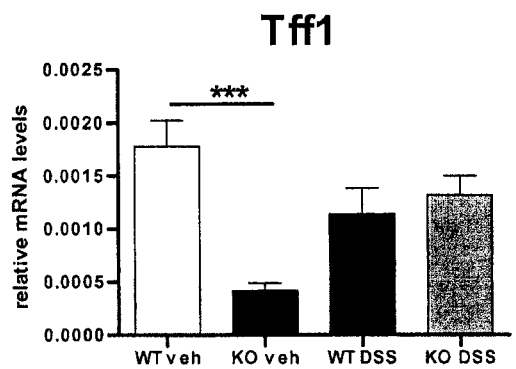
Figure 21:
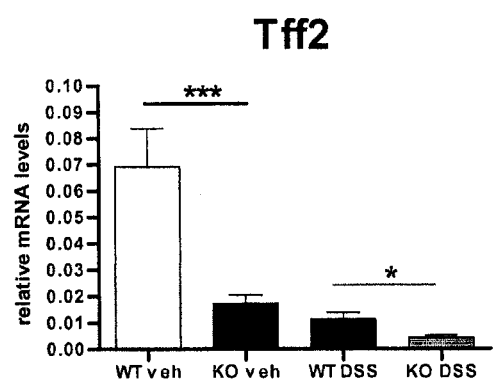
Figure 21:
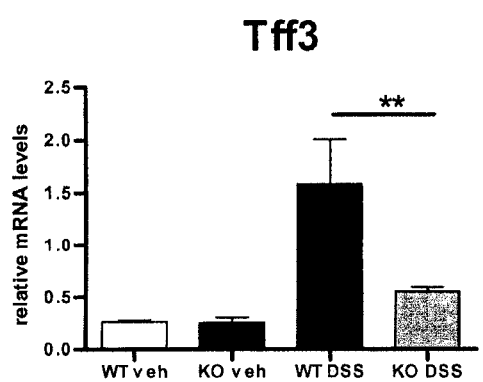
Figure 21:
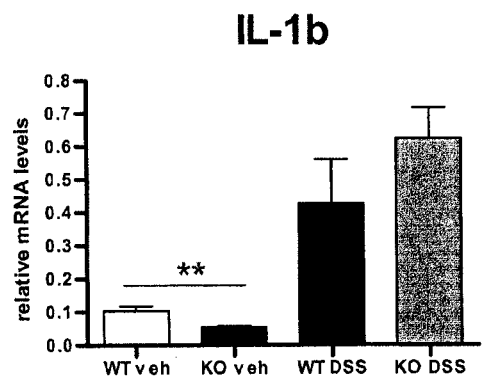
Figure 21:
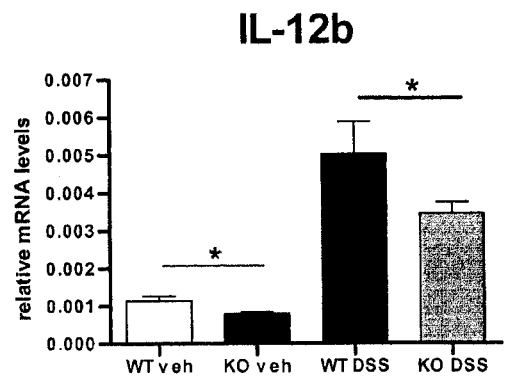
Figure 21:
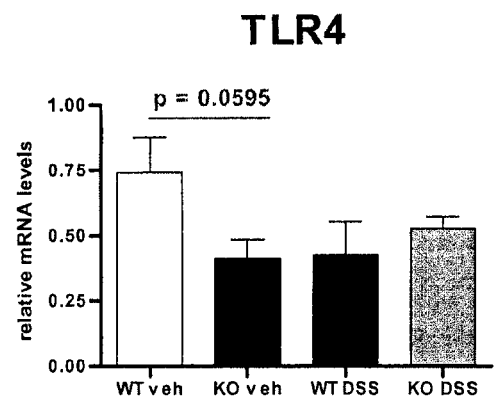
Figure 21:
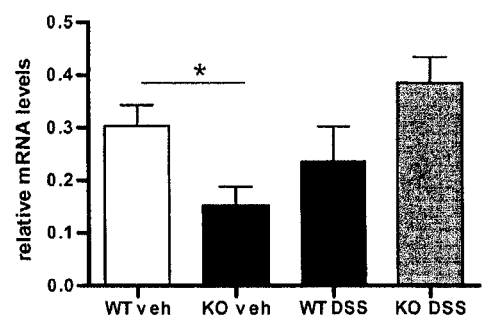
Figure 21:
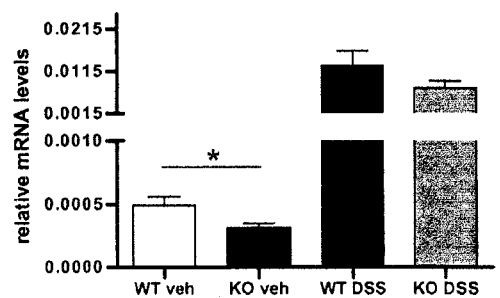
Figure 22:
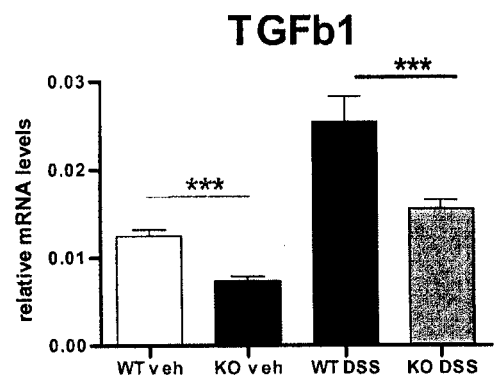
Figure 22:
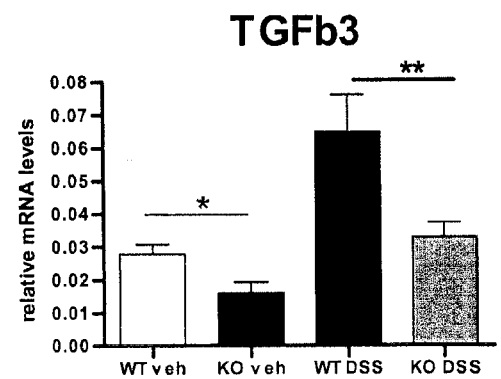
Figure 22:
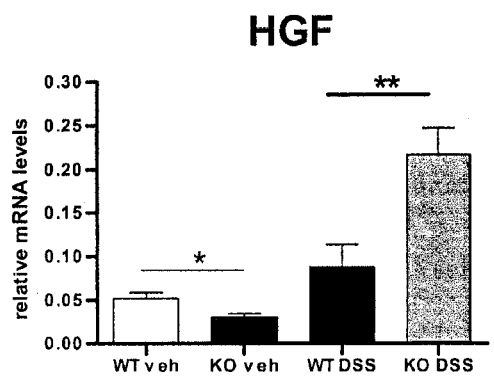
Figure 22:
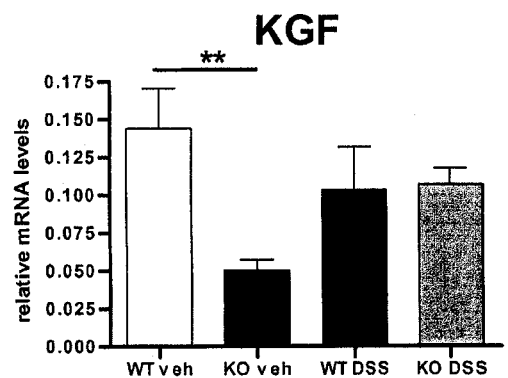
Figure 22:
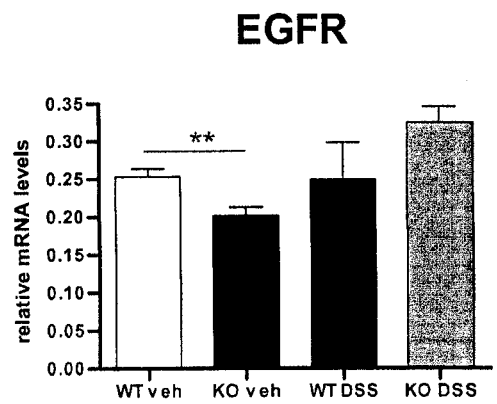

FIGS. 20A-20C are graphs illustrating that 11 week-old GLP-1R-/- mice have reduced large intestine size (large intestine weight and or large intestine length) compared to age- and sex-matched wild-type (WT) control mice. See Example 5 for protocol. For FIGS. 20A-20C: Wild type mice are represented by white bars. GLP-1R-/- mice are represented by black bars. , * represent $p<0.01$ and $p<0.001$, respectively, for GLP-1R-/- versus WT control mice. N=9-12 mice/group.

FIGS. 21A-21H are graphs illustrating that, relative to WT littermate control mice, GLP-1R-/- mice have inherently reduced levels of mRNA transcripts encoding proteins important for (i) preservation of intestinal barrier function, protection of mucosal integrity, gut repair and wound healing (Tff1, Tff2, Tff3, VIP and IL-6); (ii) increasing vascular permeability and mediating tissue repair (IL-1b); (iii) mediating long-term protection against intracellular pathogens (IL-12b); and (iv) pathogen recognition and activation of the innate immune system (TLR4). See Example 5 for protocol. For FIGS. 21A-21H, wild type mice fed regular drinking water are represented by white bars. KO mice fed regular drinking water are represented by dark grey bars. Wild type mice fed water supplemented with 3% DSS are represented by black bars. KO mice fed water supplemented with 3% DSS are represented by light grey bars. *, , * represent $p<0.05$, $p<0.01$ and $p<0.001$, respectively, for GLP-1R-/- versus WT control mice. N=9-12 mice/group. Tff=Trefoil factor; IL-1b=Interleukin 1 beta; IL-12b=Interleukin 12 beta; TLR4=Toll-like receptor 4; VIP=vasoactive intestinal peptide; IL-6=interleukin 6.

FIGS. 22A-22E are graphs illustrating that, relative to WT littermate control mice, GLP-1 R-/- mice have inherently reduced levels of mRNA transcripts that encode proteins that are important for: (i) immune system regulation, preservation of intestinal barrier function, protection of mucosal integrity, and regulation of repair (TGFb1, TGFb3, EGFR); and (ii) intestinal epithelial repair and restitution (HGF, KGF). See Example 5 for protocol. For FIGS. 22A-22E: Wild type mice fed regular drinking water are represented by white bars. KO mice fed regular drinking water are represented by dark grey bars. Wild type mice fed water supplemented with 3% DSS are represented by black bars. KO mice fed water supplemented with 3% DSS are represented by light grey bars. *, , * represent $p<0.05$, $p<0.01$ and $p<0.001$, respectively, for GLP-1R-/- versus WT control mice. N=9-12 mice/group. TGFb=Transforming growth factor beta; HGF=Hepatocyte growth factor; KGF=Keratinocyte growth factor; EGFR=Epidermal growth factor receptor.

Figure 23:
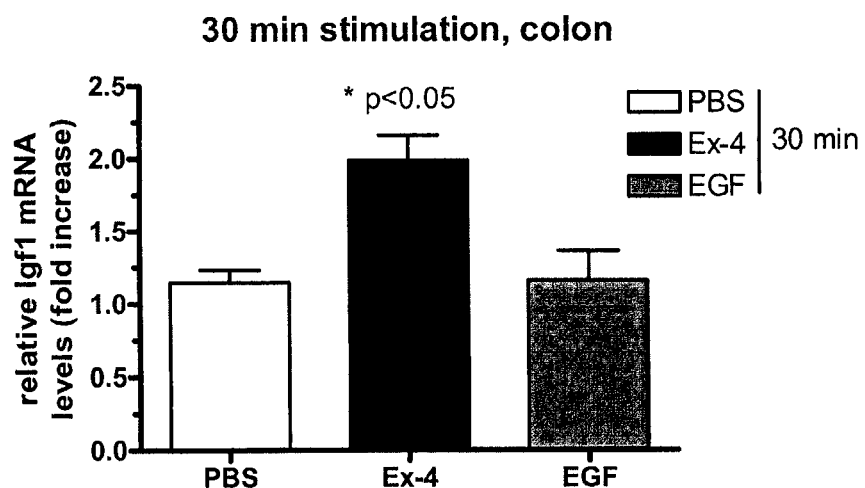
Figure 23:
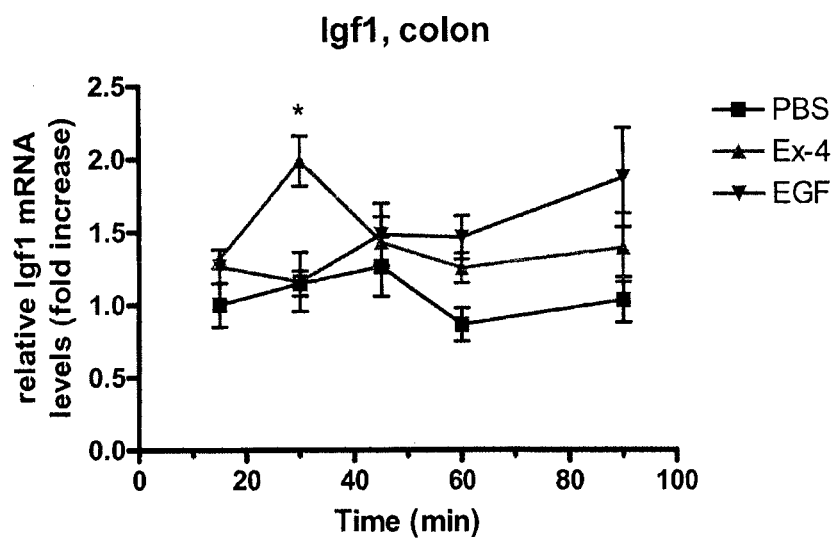

FIGS. 23A and 23B are graphs illustrating that acute administration of a GLP-1 receptor agonist increases mRNA levels of insulin-like growth factor 1 (IGF-1) in the murine large bowel. Mice were given a single subcutaneous injection of either phosphate buffered saline (PBS), epidermal growth factor (EGF, 0.5 μg/g body weight) or the GLP-1 receptor agonist exendin-4 (Exendin, 1 μg/22 g mouse, ~10 nmol/kg). See Example 5 for protocol. In FIG. 23A: Mice given injections of PBS are represented by a white bar. Mice given an injection of Ex-4 are represented by a black bar. Mice given injection of EGF are represented by a grey bar. In FIG. 23B: Mice given injections of PBS are represented by black line with a square. Mice given an injection of Ex-4 are represented by a light grey line with a triangle. Mice given injections of EGF are represented by a dark grey line with an upside down triangle. * represents $p<0.05$ for Exendin-4-treated versus PBS-treated mice. N=4 mice/group.

DETAILED DESCRIPTION OF THE INVENTION

Unless defined otherwise, all technical and scientific terms used herein have the same meaning as commonly understood by one of ordinary skill in the art to which this invention belongs.

As used herein, the terms "comprising," "including," and "such as" are used in their open and non-limiting sense.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. Thus, for example, reference to a composition containing "a GLP-1 receptor agonist" includes two or more agonists. The term "about" means plus or minus 0.1 to 50%, 5-50%, or 10-40%, preferably 10-20%, more preferably 10% or 15%, of the number to which reference is being made. The terms "administering" and "administration" refer to the process by which a therapeutically or prophylactically effective amount of a GLP-1 receptor agonist or composition contemplated herein is delivered to a subject for prevention and/or treatment purposes. Agonists and compositions are administered in accordance with good medical practices taking into account the subject's clinical condition, the site and method of administration, dosage, patient age, sex, body weight, and other factors known to physicians.

The term "pharmaceutically acceptable carrier, excipient, or vehicle" refers to an agent which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbants that may be needed in order to prepare a particular composition. The use of such agents for an active substance is well known in the art.

"Pharmaceutically acceptable salt(s)," means a salt that is pharmaceutically acceptable and has the desired pharmacological properties. By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in S. M. Berge, et al., J. Pharmaceutical Sciences, 1977, 66:1. Suitable salts include salts that may be formed where acidic protons in the compounds are capable of reacting with inorganic or organic bases. Suitable inorganic salts include those formed with alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Suitable salts also include acid addition salts formed with inorganic acids (e.g. hydrochloride and hydrobromic acids) and organic acids (e.g. acetic acid, citric acid, maleic acid, and the alkane- and arene-sulfonic acids such as methanesulfonic acid and benezenesulfonic acid). When there are two acidic groups present, a pharmaceutically acceptable salt may be a mono-acid-mono-salt or a di-salt; and similarly where there are more than two acidic groups present, some or all of such groups can be salified.

The term "substantial sequence similarity," when referring to a polypeptide indicates that, when optimally aligned with another polypeptide there is a percent sequence identity in at least about 50%, more preferably 60% of amino acid residues, usually at least about 70%, more usually at least about 80%, preferably at least about 90%, and more preferably at least about 95-98% of the amino acid residues.

"Percent sequence identity" or "sequence identity" refers to the percentage of amino acid residues or nucleotides in a candidate sequence that are identical with the amino acid residues in a polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various conventional ways, for instance, using publicly available computer software including the GCG program package (Devereux J. et al., Nucleic Acids Research 12(1): 387, 1984); BLASTP, BLASTN, and FASTA, Gap or Bestfit (Wisconsin Package Version 10.0, Genetics Computer Group (C4CG), Madison, Wis.; Pearson, Methods Enzymol. 183: 63-98, 1990; Pearson, Methods Mol. Bio. 276: 71-84, 1998). The BLAST programs are publicly available from NCBI and other sources (BLAST Manual, Altschul, S. et al. NCBI NLM NIH Bethesda, Md. 20894; Altschul, S. et al. J. Mol. Biol. 215: 403-410, 1990). Skilled artisans can determine appropriate parameters for measuring alignment, including any algorithms needed to achieve maximal alignment over the full length of the sequences being compared. Methods to determine identity and similarity are codified in publicly available computer programs.

An "analog" refers to a polypeptide wherein one or more amino acid residues of a parent or wild-type polypeptide have been substituted by another amino acid residue, one or more amino acid residues of a parent or wild-type polypeptide have been inverted, one or more amino acid residues of the parent or wild-type polypeptide have been deleted, and/or one or more amino acid residues have been added to the parent or wild-type polypeptide. Such an addition, substitution, deletion, and/or inversion may be at either of the N-terminal or C-terminal end or within the parent or wild-type polypeptide, or a combination thereof. Typically "an analog" is a peptide wherein 6 or less amino acids have been substituted and/or added and/or deleted from the parent or wild-type peptide, in particular a peptide wherein 3 or less amino acids have been substituted and/or added and/or deleted from the parent or wild-type polypeptide, and more particularly, a peptide wherein one amino acid has been substituted and/or added and/or deleted from the parent or wild-type polypeptide. Analogs include polypeptides with substantial sequence identity to a wild-type polypeptide.

An analog also includes a polypeptide with one or more blocking groups. "Blocking groups" are chemical groups that are routinely used in the art of peptide chemistry to confer biochemical stability and resistance to digestion by exopeptidase. Suitable N-terminal protecting groups include, for example, $C_{1-5}$ alkanoyl groups such as acetyl. Also suitable as N-terminal protecting groups are amino acid analogs lacking the amino function. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched $C_{1-5}$ alkyl groups, e.g., methyl, ethyl, and propyl groups, while amide-forming groups include amino functions such as primary amine, or alkylamino functions, e.g., mono-$C_{1-5}$ alkylamino and di-$C_{1-5}$ alkylamino groups such as methylamino, ethylamino, dimethylamino, diethylamino, methylethylamino and the like. Amino acid analogs are also suitable for protecting the C-terminal end of the present compounds, for example, decarboxylated amino acid analogs such as agmatine.

Mutations may be introduced into a polypeptide by standard methods, such as site-directed mutagenesis and PCR-mediated mutagenesis. Conservative substitutions can be made at one or more predicted non-essential amino acid residues. A "conservative amino acid substitution" is one in which an amino acid residue is replaced with an amino acid residue with a similar side chain. Amino acids with similar side chains are known in the art and include amino acids with basic side chains (e.g. Lys, Arg, H is), acidic side chains (e.g. Asp, Glu), uncharged polar side chains (e.g. Gly, Asp, Glu, Ser, Thr, Tyr and Cys), nonpolar side chains (e.g. Ala, Val, Leu, Iso, Pro, Trp), beta-branched side chains (e.g. Thr, Val, Iso), and aromatic side chains (e.g. Tyr, Phe, Trp, His). Mutations can also be introduced randomly along part or all of the native sequence, for example, by saturation mutagenesis. Following mutagenesis the variant polypeptide can be recombinantly expressed.

A "derivative" refers to a polypeptide in which one or more of the amino acid residues of a parent polypeptide have been chemically modified. Modifications include adding chemical moieties, creating new bonds, and removing chemical moieties. Derivatives may be obtained by chemically modifying one or more amino acid side groups, alpha-carbon atoms, terminal amino groups, terminal carboxylic acid groups of the parent polypeptide or analog thereof, for instance by alkylation, acylation, glycosylation, pegylation, ester formation, deamidation, amide formation, or by introducing a lipophilic functionality. For example, modifications at amino acid side groups may include acylation of lysine epsilon-amino groups, N-alkylation of arginine, histidine, or lysine, alkylation of glutamic or aspartic carboxylic acid groups, or deamidation of glutamine or asparagine. Terminal amino group modifications may include des-amino, N-lower alkyl, N-di-lower alkyl, and N-acyl modifications. Terminal carboxy group modifications may include the amide, lower alkyl amide, dialkyl amide, and lower alkyl ester modifications. One or more side groups, or terminal groups, may be protected by protective groups known to the ordinary skilled protein chemist. Amino acid α-carbons may be mono- or di-methylated. In aspects of the invention, "a derivative" designates a peptide or analog thereof which is chemically modified by introducing an ester, alkyl or lipophilic functionality on one or more amino acid residues of the peptide or analog thereof.

A "GLP-1 receptor agonist" is understood to refer to any compound, including peptides and non-peptide compounds, which fully or partially activates a GLP-1 receptor (e.g., human GLP-1 receptor), or fully or partially mimics or increases a reaction, activity, or function of glucagon-like peptide 1 receptor ligands or initiates such reaction, activity, or function, or reduces or prevents inhibition of any reaction, activity or function of glucagon-like peptide 1 receptor ligands. A GLP-1 receptor agonist includes indirect GLP-1 agonists such as agents that cause increased GLP-1 secretion from gut L cells. In aspects, the "GLP-1 agonist" is any peptide or non-peptide small molecule that binds to a GLP-1 receptor, preferably with an affinity constant ($K_D$) or a potency ($EC_{50}$) of below 1 μM, e.g., below 100 nM as measured by methods known in the art (see, e.g., WO 98/08871). In aspects of the invention the term GLP-1 receptor agonist includes analogs, derivatives, isomers, fragments, modifications and pharmaceutically acceptable salts.

In aspects of the invention, the GLP-1 receptor agonist is an analog of a vertebrate GLP-1 peptide. Such GLP-1 analogs can be generated using standard techniques of peptide chemistry and can be assessed for trophic activity at the large or small intestine, all according to the guidance provided herein. Particular analogs for use in the invention are those based upon the sequence of human GLP-1 (SEQ ID NO. 1), wherein one or more amino acid residues are conservatively substituted for another amino acid residue, as long as the analog still maintains its trophic activity at the small or large intestine as measured by an increase in at least one of the following parameters: small or small or large intestine length, small or small or large intestine weight, histological evidence of mucosal integrity, protein content or mass. Conservative substitutions in any naturally occurring GLP-1, preferably the human GLP-1 sequence, are defined as exchanges within any of the following five groups:

I. Ala, Ser, Thr, Pro, Gly
II. Asn, Asp, Glu, Gln
III. His, Arg, Lys
IV. Met, Leu, Ile, Val, Cys
V. Phe, Tyr, Trp.

The invention also encompasses non-conservative substitutions of amino acids in any GLP-1 peptide sequence, provided that the non-conservative substitutions occur at amino acid positions known to vary in GLP-1 isolated from different species. Non-conservative residue positions are readily determined by aligning all known GLP-1 sequences, in particular vertebrate GLP-1 sequences. Alternatively, non-conservative substitutions may be made at any position in which alanine-scanning mutagenesis reveals some tolerance for mutation in that substitution of an amino acid residue with alanine does not destroy all intestinotrophic activity at the large or small intestine. The technique of alanine scanning mutagenesis is described by Cunningham and Wells, Science, 1989, 244: 1081. Since most GLP-1 sequences consist of only approximately 31-37 amino acids (and in human GLP-1 alanine already occurs at four positions), one of skill in the art could easily test an alanine analog at each remaining position for intestinotrophic effect, as taught herein.

Any substitution, addition or deletion of a GLP-1 peptide that does not destroy the activity of the GLP-1 peptide may be usefully employed in this invention. In embodiments a GLP-1 analog is at least as active as native human GLP-1. In particular embodiments, the GLP-1 analog has enhanced activity compared with native human GLP-1. For example, such analogs may exhibit enhanced serum stability, enhanced receptor binding and enhanced signal transducing activity. Other modifications to GLP-1 and GLP-1 analogs that may usefully be employed in this invention are those which render the molecule resistant to oxidation. In an aspect of the invention, the GLP-1 analog is produced by the alteration of native GLP-1 to confer DPP-IV resistance. In an aspect, the GLP-1 analogs are members of a class of GLP-1 analogs which incorporate at positions 8 or 9 a replacement amino acid which confers on the GLP-1 analog relative resistance to DPP-IV mediated cleavage, as determined by any convenient in vitro or in vivo assessment technique that is able to detect the presence of GLP-1 digestion products. A DPP-IV resistant GLP-1 analog is defined as that GLP-1 analog which is processed or degraded at a rate that is measurably slower than the rate at which human GLP-1 is processed or degraded, under the same conditions. DPP-IV-resistant analogs that also retain intestinotrophic activity may be screened in an assay of intestinotrophic activity (see, for example U.S. Pat. No. 5,789,379).

The present invention is compatible with use of a wide spectrum of GLP-1 receptor agonists. In an aspect, a GLP-1 receptor agonist comprises or is selected from the group of glucagon-like peptide 1 receptor peptides consisting of GLP-1(1-36) [SEQ ID NO.: 1], GLP-1(1-37) [SEQ ID NO.: 2], GLP-1 (1-38), GLP-1 (1-39), GLP-1 (1-40), GLP-1 (1-41), active GLP-1 peptides 7-34, 7-35, 7-36, 7-37, 7-38, 7-39, 7-40, and 7-41, amide analogs GLP-1(7-34)-amide, GLP-1 (7-35)-amide, GLP-1 (7-36)-amide, GLP-1 (7-37)-amide, GLP-1(7-38)-amide GLP-1(7-39)-amide GLP-1(7-40)-amide, and GLP-1(7-41)-amide, and derivatives or analogs thereof.

In aspects of the invention, the GLP-1 receptor agonist is an analog of GLP-1 peptide GLP-1(7-37) [SEQ ID NO.: 3] or GLP-1(7-36) [SEQ ID NO.: 4] which has less than 10 amino acid residues that are different from those in GLP-1 peptide GLP-1(7-37) or GLP-1(7-36), less than 5 amino acid residues that are different from those in GLP-1(7-37) or GLP-1(7-36), less than 3 amino acid residues that are different from those in GLP-1 peptide GLP-1(7-37) or GLP-1(7-36), preferably only one amino acid residue that is different from a sequence of GLP-1 peptide GLP-1(7-37) or GLP-1(7-36).

In aspects of the invention, the GLP-1 receptor agonists include GLP-1 peptides where one or more amino acids have been added to the N-terminus and/or C-terminus of GLP-1 (1-37), GLP-1(7-37) or GLP-1(7-36). In an embodiment, about one to six amino acids may be added to the N-terminus and/or from about one to eight amino acids may be added to the C-terminus. Amino acids at positions 38-45 of an extended GLP-1 agonist may be selected so that they are the same or conservative substitutions of the amino acids at the corresponding positions of exendin-3 or exendin-4.

A group of GLP-1 receptor analogs or derivatives for use in the present invention may comprise the GLP-1 receptor agonists described in U.S. Pat. No. 5,545,618 and US Patent Application Serial No. 20040018975. The analogs include active GLP-1 peptides, 7-34, 7-35, 7-36 and 7-37 having amino acid substitutions at positions 7-10 and/or are truncations at the C-terminus and/or contain various other amino acid substitutions in the basic peptide. Particular analogs include those with D-amino acid substitutions in the 7 and 8 positions and/or N-alkylated or N-acylated amino acids in the 7 position since they are particularly resistant to degradation in vivo. In aspects of the invention, the GLP-1 receptor agonist is Val$^8$-GLP-1(7-37), Gln$^9$-GLP-1(7-37), D-Gln$^9$-GLP-1(7-37), Gly$^8$-GLP-1(7-36)NH$_2$, acetyl-Lys$^9$-GLP-1 (7-37), Thr$^9$-GLP-1(7-37), D-Thr$^9$-GLP-1(7-37), Asn$^9$-GLP-1(7-37), and D-Asn$^9$-GLP-1(7-37).

In another aspect of the invention at least one amino acid of a GLP-1 receptor agonist has at least one substituent attached directly or indirectly (e.g. via a spacer such as γ-Glu or β-Ala). A substituent is generally selected to make the profile of action of the parent GLP-1 receptor agonist more protracted, make the GLP-1 receptor agonists more metabolically and physically stable, and/or increase solubility of the GLP-1 receptor agonist. Examples of a substituent include an amide, a carbohydrate, and a lipophilic substituent. A lipophilic substituent includes but is not limited to an alkyl group, a group which has an co-carboxylic acid group, an acyl group of a straight-chain or branched fatty acid or alkane such as tetradecanoyl and hexadecanoyl. Particular compositions and treatments of the invention may use GLP-1 receptor agonists with lipophilic substitutents such as those described in WO 99/43341 (Novo Nordisk) and US 2003/0119734A1 (Novo Nordisk). In aspects of the invention, a GLP-1 receptor agonist is a derivative of GLP-1(7-36)-amide, GLP-1(7-37), a GLP-1(7-36)-amide analog or a GLP-1(7-37) analog, which comprises at least one lipophilic substituent.

A GLP-1 receptor agonist may be a stable GLP-1 peptide analog/derivative which includes a GLP-1 analog or a derivative of a GLP-1 analog which exhibits an in vivo plasma elimination half-life of at least 10 hours in man, as determined by the method described below. Examples of stable GLP-1 analogs/derivatives can be found in WO 98/08871, WO 99/43706 and WO 02/46227. The method for determination of plasma elimination half-life of a compound in man is summarized as follows. The compound is dissolved in an isotonic buffer, pH 7.4, PBS or any other suitable buffer. The dose is injected peripherally, preferably in the abdomen or upper thigh. Blood samples for determination of active compound are taken at frequent intervals, and for a sufficient duration to cover the terminal elimination part (e.g., Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51): A143, 2000. Derived pharmacokinetic parameters are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

In aspects of the invention, the GLP-1 receptor agonist is an exendin including an exendin agonist. An "exendin agonist" is a compound that fully or partially mimics or increases the effects, activity or reactions of an exendin, or reduces or prevents inhibition of any effect, activity or reaction of an exendin. Exendins also include analogs and derivatives of a naturally occurring exendin peptide, in particular a stable analog or derivative of a naturally occurring exendin peptide.

Exendins include without limitation exendin-4, exendin-3, or analogs or derivatives thereof. Exendin-3 is present in the salivary secretions of *Heloderma horridum* (Mexican Beaded Lizard) (Eng, J., et al., *J. Biol. Chem.*, 267:7402-05, 1992). A sequence for an exendin-3 peptide is in SEQ ID NO: 5. Exendin-4 is a novel peptide from *Heloderma suspectum* (Gila monster) venom, having 53% amino acid identity with GLP-1 (7-36)amide (*J. Biol. Chem.*, 267:7402-05, 1992). A sequence for an exendin-4 peptide is in SEQ ID NO: 6.

Examples of exendins as well as analogs, derivatives, fragments, and agonists thereof are disclosed in PCT Published Application Nos. WO 97/46584, WO 01/04156, WO 00/42026, U.S. Pat. Nos. 6,956,026, 6,924,264, 6,902,744, 5,424,286, 6,528,486, 6,989,366, 6,956,026 and 6,506,724, US Published application Nos. 20060035836A1, and 20050267034A1, and publications and patents and patent applications referenced therein and including all references therein. WO 97/46584 describes truncated versions of exendin peptide(s). WO 01/04156 describes exendin-4 analogs and derivatives as well as the preparation of these molecules. Exendin-4 analogs stabilized by fusion to serum albumin or Fc portion of an Ig are disclosed in WO 02/46227. Particular examples of exendin analogs include $^{14}$Leu, $^{25}$Phe exendin-4 amide, $^{14}$Leu, $^{25}$Phe exendin-4 (1-28) amide and $^{14}$Leu, $^{22}$Ala, $^{25}$Phe exendin-4 (1-28) amide.

In aspects of the invention, the GLP-1 agonist is a stable exendin-4 analog/derivative. The term "stable exendin-4 analog/derivative", as used herein refers to an exendin-4(1-39) analog or a derivative of an exendin-4(1-39) analog which exhibits an in vivo plasma elimination half-life greater than 2 hrs in man, as determined by the method described above for a "stable GLP-1 analog/derivative".

GLP-1 receptor agonists which may be used according to the present invention include those referred to in WO 99/43705 (Novo Nordisk A/S), WO 99/43706 (Novo Nordisk A/S), WO 99/43707 (Novo Nordisk A/S), WO 98/08871 (Novo Nordisk A/S), WO 99/43708 (Novo Nordisk A/S), WO 99/43341 (Novo Nordisk A/S), WO 87/06941 (The General Hospital Corporation), WO 90/11296 (The General Hospital Corporation), WO 91/11457 (Buckley et al.), WO 98/43658 (Eli Lilly & Co.), EP 0708179-A2 (Eli Lilly & Co.), EP 0699686-A2 (Eli Lilly & Co.), WO 01/98331 (Eli Lilly & Co), WO91/11457, WO98/05351; WO98/30231; and in U.S. Pat. Nos. 6,593,295; 6,541,500; 6,329,336; 6,358,924; 6,344, 180; 6,284,725; 6,277,819; 6,271,241; 6,268,343; 6,191,102; 6,162,907; 6,133,235; 5,977,071, 5,981,488; 6,051,689; 6,006,753; 5,863,555; 5,846,937; 5,670,360; 5,614,492; 5,846,937; 5,545,618; 5,424,286; 6,410,508; 6,388,053; 6,384,016; 6,329,336; 6,110,703; 5,846,747; 5,670,360; 5,188,666; 5,120,721; and 5,631,224. GLP-1 receptor agonists are in each case generically and specifically disclosed in the referenced patent document. Any of the substances disclosed in the patent documents is considered potentially useful as an GLP-1 receptor agonist to be used in carrying out the present invention.

Exemplary GLP-1 agonist compositions include: BIM 51077 (GLP-1 analog resistant to DPP-IV digestion, available from Beaufour Ipsen); AC2592 (GLP-1, from Amylin, San Diego Calif.); Byetta® (Eli Lilly and Amylin); ThGLP-1 (GLP-1, modified amino acids and fatty acid attachment, from Theratechnologies, Saint-Laurent, Quebec, Canada);

DAC:GLP-1 (Conjuchem, Montreal, Quebec, Canada); CJC-1131 or DAC:GLP-1 (GLP-1 analog engineered for covalent coupling to albumin, Conjuchem), LY315902 and sustained release LY315902 (DDP-IV resistant GLP-1 analog from Eli Lilly, Indianapolis, Ind.); low molecular weight GLP-1 mimetic, Albugon or albiglutide (albumin:GLP-1 fusion peptide from Human Genome Sciences, Rockville, Md.); and Liraglutide (NN2211) or Victoza® (Novo Nordisk, Elbrond et al., Diabetes Care 2002 Aug. 25(8): 1398-404).

In aspects of the invention, the GLP-1 receptor agonist is an exendin-4, in particular exenatide, more particularly the Byetta product, or exenatide in a microsphere formulation administered once weekly (exenatide LAR).

In aspects of the invention, the GLP-1 receptor agonist is liraglutide, more particularly the Victoza® product.

An amino acid portion of a GLP-1 receptor agonist can be prepared by a variety of methods known in the art such as solid-phase synthesis, purification of GLP-1 agonists from natural sources, recombinant technology, or a combination of these methods. See for example, U.S. Pat. Nos. 5,188,666, 5,120,712, 5,523,549, 5,512,549, 5,977,071, 6,191,102, Dugas and Penney 1981, Merrifield, 1962, Stewart and Young 1969, and the references cited herein. GLP-1 receptor agonist derivatives can be produced by appropriate derivatization of an appropriate backbone produced, for example, by recombinant DNA technology or peptide synthesis (e.g., Merrifield-type solid phase synthesis) using methods known in the art of peptide synthesis and peptide chemistry. Commercially available chemical libraries may also be useful for screening for small molecule GLP-1 receptor agonists using high throughput or ultra high throughput screening technology. Methods for identifying GLP-1 receptor agonists are described in the art (see for example WO 93/19175 Novo Nordisk A/S).

Particular forms of GLP-1 receptor agonists selected for promoting the growth of small or large intestinal tissue can be prepared by a variety of techniques well known for generating peptide products. GLP-1 receptor agonists may be obtained by extraction from the natural source, using an appropriate combination of protein isolation techniques. Isolation and purification from vertebrate sources may be achieved from acid-ethanol extracts of ileal mucosa by a combination of size selection and HPLC-based fractionation, with the aid of antibody raised against synthetic proglucagon 78-107, to monitor work-up (Buhl et al, 1988, J. Biol Chem 263:8621). As an alternative to extraction, those forms that incorporate only L-amino acids, can be produced in commercial quantities by application of recombinant DNA technology. For this purpose, DNA coding for the desired agonist may be incorporated into an expression vector and transformed into a microbial, e.g., yeast, or other cellular host, which is then cultured under conditions appropriate for expression. A variety of gene expression systems have been adapted for this purpose, and typically drive expression of the desired gene from expression controls used naturally by the chosen host. Because the agonists do not require post translational glycosylation for activity, their production may be conveniently achieved in bacterial hosts such as $E.$ $coli$. For such production, DNA coding for the selected peptide agonist may usefully be placed under expression controls of the lac, trp or PL genes of $E.$ $coli$. As an alternative to expression of DNA coding for the peptide per se, the host can be adapted to express the peptide as a fusion protein in which the peptide is linked releasably to a carrier protein that facilitates isolation and stability of the expression product.

In an approach universally applicable to the production of a selected GLP-1 receptor agonist, in particular a GLP-1 or GLP-1 analog, and one used to produce GLP-1 receptor agonists that incorporate non-genetically encoded amino acids and N- and C-terminally derivatized forms the well established techniques of automated peptide synthesis are employed. General descriptions appear, for example, in J. M. Stewart and J. D. Young, Solid Phase Peptide Synthesis, 2nd Edition, 1984 Pierce Chemical Company, Rockford, Ill.; and in M. Bodanszky and A. Bodanszky, The Practice of Peptide Synthesis, 1984, Springer-Verlag, New York; Applied Biosystems 430A Users Manual, 1987, ABI Inc. Foster City, Calif. In these techniques, a peptide is grown from its C-terminal, resin-conjugated residue by the sequential addition of appropriately protected amino acids, using either the Fmoc or tBoc protocols, as described for instance by Orskov et al., Febs Letters, 1989, 247(2):193-196.

For the incorporation of N- and/or C-blocking groups, protocols conventional to solid phase peptide synthesis methods can also be applied. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB resin, which upon HF treatment releases peptide bearing an N-methylamidated C-terminus. Protection of the C-terminus by esterification can also be achieved using conventional procedures. This entails use of a resin/blocking group combination that permits release of side-chain protected peptide from the resin, to allow for subsequent reaction with the desired alcohol, to form the ester function. FMOC protecting groups, in combination with DVB resin derivatized with methoxyalkoxybenzyl alcohol or equivalent linker, can be used for this purpose, with cleavage from the support being effected by TFA in dichloromethane. Esterification of the suitably activated carboxyl function, e.g., with DCC, can then proceed by addition of the desired alcohol, followed by deprotection and isolation of the esterified GLP-1 peptide.

Incorporation of N-terminal blocking groups can be achieved while the synthesized peptide is still attached to the resin, for instance by treatment with suitable anhydride and nitrile. To incorporate an acetyl blocking group at the N-terminus, for instance, the resin-coupled peptide can be treated with 20% acetic anhydride in acetonitrile. The N-blocked peptide can then be cleaved from the resin, deprotected and subsequently isolated.

Once the desired GLP-1 receptor agonist peptide has been synthesized, cleaved from the resin and fully deprotected, the peptide is then purified to ensure the recovery of a single oligopeptide having the selected amino acid sequence. Purification can be achieved using any of the standard approaches, which include reversed-phase high-pressure liquid chromatography (RP-HPLC) on alkylated silica columns, e.g., $C_4$ $C_8$ or $C_{18}$-silica. Such column fractionation is generally accomplished by running linear gradients, e.g., 10-90%, of increasing % organic solvent, e.g., acetonitrile, in aqueous buffer, usually containing a small amount (e.g., 0.1%) of pairing agent such as TFA or TEA. Alternatively, ion-exchange HPLC can be employed to separate peptide species on the basis of their charge characteristics. Column fractions are collected, and those containing peptide of the desired/required purity are optionally pooled. In one embodiment of the invention, the GLP-1 receptor agonist peptide is then treated in the established manner to exchange the cleavage acid (e.g., TFA) with a pharmaceutically acceptable acid, such as acetic, hydrochloric, phosphoric, maleic, tartaric, succinic and the like, to generate a pharmaceutically acceptable acid addition salt of the peptide.

GLP-1 receptor agonists, in particular analogs of GLP-1 and exendin and small molecule agonists identified as GLP-1 receptor agonists, may be screened for therapeutic and related utility to treat conditions involving the large or small intestine using animal models. Animal models useful for studying inflammatory conditions involving the large or small intestine are described in the literature. (See Elson et al., 1995, Gastroenterology 109:1344-1367; Kim et al., 1992, Scand. J. Gastroenterol. 27:529-537; Dieleman et al., 1994, Gastroenterology 107:1643-1652; Domek et al., 1995, Scand. J. Gastroenterol. 30:1089-1094; Mashimo et al., 1996, Science 274: 262-265; Okayasu et al., 1990, Gastroenterology, 98:694-702; Takizawa et al., 1995, Adv. Exp. Med. Biol. 371:1383-1387; and Wells et al., 1990, J. Acquired 1 mm. Defic. Syndromes 3:361-365). For example, ulcerative colitis is inducible in test mice using dextran sulphate (Okayasu et al., 1990, supra.). Typically test mice ingesting 3-10% dextran sulphate in their drinking water show at least one of the following symptoms within 6-10 days: weight loss, rectal bleeding or diarrhea, lethargy, weakness, and decreased movement, eating and drinking. Thus, this animal model can be used to assess the ability of compounds identified as GLP-1 receptor agonists to ameliorate inflammatory conditions involving the small or small or large intestine.

The terms "subject" and "patient" are used interchangeably herein and refer to an animal including a warm-blooded animal such as a mammal, which is afflicted with or suspected of having or being pre-disposed to a condition involving the small or small or large intestine. Preferably, the terms refer to a human. The terms also include domestic animals bred for food, sport, or as pets, including horses, cows, sheep, poultry, fish, pigs, cats, dogs, and zoo animals. The methods herein for use on subjects and patients contemplate prophylactic as well as curative use. Typical subjects in need of treatment include persons susceptible to, suffering from or that have suffered a condition or disorder involving the small or large intestine.

The invention relates to therapeutic and related uses of GLP-1 receptor agonists, in particular for the amelioration of medical or veterinary conditions in which functioning of the small or small or large intestine is impaired by disease or injury. For example, the method is usefully applied to treat subjects suffering from an inflammatory condition of the small or large intestine, or subjects who have undergone resection of the small or large intestine. As used herein the term "large intestine" means the distal portion of the intestine, extending from its junction with the small intestine to the anus: it comprises the cecum, colon, rectum, and anal canal. As used herein, the term "small intestine" means the proximal portion of the intestine extending from the stomach to the small or large intestine, comprising the duodenum, jejunum and ileum.

Any subject requiring enhancement of the activity of the small or large intestine may potentially be a candidate for treatment with a GLP-1 receptor agonist according to the invention. In particular, a group of conditions that may be beneficially treated according to the invention are inflammatory conditions of the intestine involving the small or large intestine (inflammatory bowel diseases, or "IBD"). Human patients are typically diagnosed as having such a condition after manifesting one or more of the following symptoms: pain in the abdomen, pain with defecation, diarrhea or constipation (best described as a change in the normal bowel "habit"), rectal bleeding, fever, weight loss, anemia, and fluid loss leading to dehydration. Visualization using sigmoidoscopy or colonoscopy can be used to confirm the presence of an inflammatory condition of the small or large intestine. Alternatively, biopsies or a barium enema x-ray can be used to complete the diagnosis. Inflammatory bowel diseases include Crohn's disease and ulcerative colitis, infectious colitis, drug or chemical-induced colitis, diverticulitis, and ischemic colitis. Standards for assessing the severity of such diseases are well known in the art (see, for example, Hanuer, 1996, New Eng. J. Med. 334:841-848).

Subjects identified to be at risk of developing an IBD and subjects in remission from a condition involving inflammation of the small or large intestine may be beneficially treated prophylactically with a GLP-1 receptor agonist according to the invention to inhibit or delay onset of inflammation of the small or large intestine. For example, ulcerative colitis and Crohn's disease can be familial diseases, accordingly, linkage studies can identify susceptible individuals (see, for example, Hugot et al., 1996, Nature 379:821-823). Further, as it is known that the risk of colitis is increased in persons who have "quit" smoking, a GLP-1 receptor agonist may be advantageously administered to such subjects particularly susceptible to developing colitis.

Treatment with GLP-1 receptor agonists has been demonstrated to increase the length of the small or large intestine. Accordingly, subjects who would benefit from an increase in the length of the small or large intestine, for example patients who have undergone partial or non-total resection of the small or large intestine, may be beneficially treated with GLP-1 receptor agonists according to the invention.

Treatment with GLP-1 receptor agonists has been demonstrated to increase the length of the small intestine. Accordingly, subjects who would benefit from an increase in the length of the small intestine, for example patients who have undergone partial or non-total resection of the small intestine, may be beneficially treated with GLP-1 receptor agonists according to the invention.

For administration to patients, the GLP-1 receptor agonist or its salt is provided, in one aspect of the invention, in pharmaceutically acceptable form, e.g., as a preparation that is sterile-filtered, e.g., through a 0.22 μm filter, and substantially pyrogen-free. Desirably, the GLP-1 receptor agonist to be formulated migrates as a single or individualized peak on HPLC, exhibits uniform and authentic amino acid composition and sequence upon analysis thereof, and otherwise meets standards set by the various national bodies which regulate quality of pharmaceutical products.

For therapeutic use, the chosen GLP-1 receptor agonist is formulated with a carrier that is pharmaceutically acceptable and is appropriate for administering the agonist to the subject by the chosen route of administration so as to deliver the agonist to the small or large intestine. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion, e.g., when used as liquid nutritional supplements for patients on total parenteral nutrition therapy, or by injection, e.g., sub-cutaneously, intramuscularly or intravenously, and are accordingly utilized as aqueous solutions in sterile and pyrogen-free form and optionally buffered to physiologically tolerable pH, e.g., a slightly acidic or physiological pH. Thus, the compounds may be administered in a vehicle such as distilled water or, more desirably, in saline, phosphate buffered saline or 5% dextrose solution. Water solubility of the GLP-1 receptor agonist may be enhanced, if desired, by incorporating a solubility enhancer, such as acetic acid or sodium hydroxide.

The aqueous carrier or vehicle can be supplemented for use as injectables with an amount of gelatin effective to achieve the depot effect expected to lie in the range from 10-20%. Alternative gelling agents, such as hyaluronic acid, may also be useful as depoting agents (also veterinary applications).

As an alternative to injectable formulations, the GLP-1 receptor agonist may be formulated for administration to patients and delivery to the small or large intestine by other routes. Oral dosage forms, such as tablets, capsules and the like, can be formulated in accordance with standard pharmaceutical practice. The compounds may also be formulated in rectal compositions such as suppositories or retention enemas, e.g., containing conventional suppository bases such as cocoa butter or other glycerides.

GLP-1 receptor agonists may also be formulated as a slow release implantation device for extended and sustained administration of the agonist. Examples of such sustained release formulations include composites of bio-compatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., Polymers for Advanced Technologies 3:279-292 (1992). Additional guidance in selecting and using polymers in pharmaceutical formulations can be found in the text by M. Chasin and R. Langer (eds.), "Biodegradable Polymers as Drug Delivery Systems", Vol. 45 of "Drugs and the Pharmaceutical Sciences", M. Dekker, New York, 1990. Liposomes may also be used to provide for the sustained release of a GLP-1 receptor agonist. Details concerning how to use and make liposomal formulations of drugs of interest can be found in, among other places, U.S. Pat. Nos. 4,921,706; 5,008,050; 4,921,706; 4,927,637; 4,452, 747; 4,016,100; 4,311,712; 4,370,349; 4,372,949; 4,529,561; 5,009,956; 4,725,442; 4,737,323; 4,920,016. Sustained release formulations are of particular interest when it is desirable to provide a high local concentration of a GLP-1 receptor agonist, e.g., near or at the small or large intestine to promote small or large intestine growth in colitis etc.

For use in stimulating growth of the small or large intestine in a mammal including a human, the present invention provides in one of its aspects a package, in the form of a sterile-filled vial or ampoule, that contains a tissue growth promoting amount of the GLP-1 receptor agonist, in either single unit dose or multi-dose amounts, wherein the package incorporates a label instructing use of its contents for the promotion of such growth. In one embodiment of the invention, the package contains the GLP-1 receptor agonist and the desired carrier, as an administration-ready formulation. Alternatively, and according to another embodiment of the invention, the package provides the GLP-1 receptor agonist in a form, such as a lyophilized form, suitable for reconstitution in a suitable carrier, such as phosphate-buffered saline.

In one embodiment, the package is a sterile-filled vial or ampoule containing an injectable solution which comprises an effective, small or large intestine proliferating amount of GLP-1 receptor agonist dissolved in an aqueous vehicle.

According to the present invention, the GLP-1 receptor agonist is administered to treat patients that would benefit from growth and/or repair of the tissue of the small or large intestine. In general, patients who would benefit from either increased small or large intestinal mass and consequent increased small or large intestine mucosal function are candidates for treatment with GLP-1 receptor agonists. Particular conditions that may be treated with a GLP-1 receptor agonist include the various forms of inflammatory bowel disease including colitis and Crohn's disease, as well as patients who have undergone partial or sub-total resection of the small or large intestine. The therapeutic efficacy of the GLP-1 treatment may be monitored by: subjective improvement in abdominal pain, diarrhea or rectal bleeding; weight gain; normalization of hemoglobin or white blood cell count and sedimentation rate; improved appearance of the intestine on colonoscopy or sigmoidoscopy, improvement of intestine function as assessed radiologically by barium enema; histological improvement as assessed by specimen biopsy; and by amelioration (reduction or elimination) of the symptoms associated with these conditions. For example, a GLP-1 receptor agonist is administrated to a patient with an inflammatory condition involving the small or large intestine in an amount sufficient to ameliorate the intestinal discomfort, bleeding and diarrhea caused by the condition. Additionally, a GLP-1 receptor agonist may be administered to patients who are identified as being at risk of developing IBD.

The therapeutic dosing and regimen most appropriate for patient treatment will of course vary with the disease or condition to be treated, and according to the patient's weight and other parameters. In embodiments of the invention, a dose of GLP-1 receptor agonist equivalent to about 1 mg/kg or less, administered twice daily over 10 days can be administered to ameliorate inflammatory conditions of the small or large intestine. However, it is expected that much smaller doses, e.g., in the $\mu g/kg$ range or even lower, and shorter or longer duration or frequency of treatment, will also produce therapeutically useful results, i.e., a statistically significant increase particularly in small or large intestine mass and reduced large bowel inflammation. In embodiments, the invention employs much smaller doses of GLP-1 receptor agonists than those traditionally used and required to regulate blood glucose or body weight or less frequent administration of GLP-1 receptor agonists such as once daily dosing of GLP-1 receptor agonists in regimens that do not significantly lower blood glucose and/or body weight yet provide significant effects on the gastrointestinal tract. The dosage sizes and dosing regimen most appropriate for human use may be guided by and extrapolated from the preclinical results herein presented, and can be confirmed in properly designed clinical trials.

An effective dosage and treatment protocol may be determined by conventional means, starting with a low dose in laboratory animals and then increasing the dosage while monitoring the effects, and systematically varying the dosage regimen as well. The doses, in mg/kg that are used in animals, may in some instances be 1,000-10,000 times higher than those used in humans. Numerous factors may be taken into consideration by a clinician when determining an optimal dosage for a given subject. Primary among these is the amount of GLP-1 normally circulating in the plasma, which is on the order of 11±1 pmol/l in the basal state and 26+3 pmol/l following a mixed meal for a human adult (Vilsboll, T et al, Diabetes, 2001, 50:609-613, and see also Orskov, C. and Holst, J. J., 1987, Scand. J. Clin. Lab. Invest. 47:165). Additional factors include the size of the patient, the age of the patient, the general condition of the patient, the particular disease being treated, the severity of the disease, the presence of other drugs in the patient, the in vivo activity of the GLP-1 receptor agonist and the like. The trial dosages would be chosen after consideration of the results of animal studies and the clinical literature. It will be appreciated by the person of ordinary skill in the art that information such as binding constants and Ki derived from in vitro binding competition assays may also be used in calculating dosages.

In general, a human dose of a GLP-1 receptor agonist used to ameliorate inflammatory conditions of the small or large intestine may be from about 0.1 µg/kg body weight/day to 100 mg/kg/day.

In embodiments of the invention comprising exenatide, the dose may be from about 0.01 µg/kg body weight/day to 5 µg/kg/day, 0.1 µg/kg body weight/day to 5 µg/kg/day, or 0.1 µg/kg body weight/day to 1 µg/kg/day.

In embodiments of the invention comprising liraglutide, the dose is from about 1 µg/kg/day to about 100 µg/kg/day, about 5 µg/kg/day to about 50 µg/kg/day, 5 µg/kg/day to about 30 µg/kg/day or about 5 µg/kg/day to about 25 µg/kg/day, in particular 25 µg/kg/day or 30 µg/kg/day.

In embodiments of the invention comprising liraglutide, the dose is from about 1 µg/kg to about 100 µg/kg, about 5 µg/kg to about 50 µg/kg, 5 µg/kg to about 30 µg/kg or about 5 µg/kg to about 25 µg/kg twice daily, in particular 25 µg/kg or 30 µg/kg twice daily.

In aspects of the invention, the dose of a GLP-1 receptor agonist may be from about 1 to 2000 µg/day or about 10 to 2000 µg/day. In embodiments of the invention comprising liraglutide, the dose is from about 500 to 2000 µg/day, 600 to 2000 µg/day or 600 to 1800 µg/day In embodiments of the invention comprising exenatide, the dose is from about 5-25 µg/day or 10-20 µg/day.

A dose or dosage unit may comprise about 0.001 to 5 mg of a GLP-1 receptor agonist, in particular 0.001 to 3 mg, or 0.005 to 2 mg. In embodiments, a dose or dosage unit may comprise about 0.3 to 2 mg of liraglutide, in particular 0.3, 0.6, mg, 1.2 mg or 1.8 mg of liraglutide. In embodiments, a dose or dosage unit may comprise about 2.5 to 5 µg of exenatide, in particular 5 µg or 7.5 µg of exenatide per day.

In embodiments of the invention, the dose of a GLP-1 receptor agonist is selected that is lower than current dosing regimens employed for the treatment of diabetes or obesity, and does not significantly lower blood glucose and/or body weight. In embodiments, liraglutide is administered at a dose of less than 2 mg/day, 1.5 mg/day, 0.6 mg/day or 0.3 mg/day, or a dose less than 10 µg/kg/day, 9 µg/kg/day, 5 µg/kg/day or 3 µg/kg/day. In embodiments, exenatide is administered at a dose of less than 20 µg/day, 15 µg/day, 10 µg/day, 5 µg/day or 2.5 µg/day, or a dose less than 0.5 µg/kg/day, 0.3 µg/kg/day, 0.2 µg/kg/day 0.1 or 0.05 µg/kg/day. In embodiments, a dose or dosage unit is provided, preferably for subcutaneous administration that delivers less than 0.6 mg/day, in particular about 0.1 to about 0.5 mg/day, 0.2 to 0.5 mg/day or 0.3 to 0.5 mg/day or 0.4 to 0.5 mg/day of liraglutide. In embodiments, a dose or dosage unit is provided, preferably for subcutaneous administration, comprising less than 5 µg of exenatide, in particular, 1-4 µg of exenatide, 1-3 µg of exenatide, or 1-2 µg or exenatide in a single unit dose or multi-dose unit.

In embodiments of the invention, a GLP-1 receptor agonist is administered once, twice or three times daily, preferably once or twice daily, more preferably once daily, and potentially once every other day. In embodiments, a GLP-1 receptor agonist is administered once daily without significantly lowering blood glucose and/or body weight in a subject. In particular embodiments, a GLP-1 receptor agonist is administered every other day without significantly lowering blood glucose and/or body weight in a subject. In particular embodiments, an exenatide is administered once daily or every other day or once weekly without significantly lowering blood glucose and/or body weight in a subject.

A composition or method of the invention may comprise one or more additional component or treatment, in particular a component or procedure for treating or preventing a condition in which functioning of the small or large intestine is impaired or that enhances the function of the small or large intestine. The composition may comprise one or more single dosage units in combination. When administered in combination each component may be administered at the same time, or sequentially in any order at different points in time. Each component may be administered separately, but sufficiently close in time to provide the desired therapeutic effect. The first component may be administered in a regimen that additionally comprises treatment with the second component. In aspect, a GLP-1 receptor agonist and additional component can be administered as separate medicaments each containing one of the components as well as simultaneously administered whether or not the components are combined in one formulation or whether they are in separate formulations. Additional components which can be utilized in the present invention include without limitation peptide hormones, antibiotics, corticosteroids and immune modifying drugs. Examples of additional components are peptide hormone such as IGF-1, IGF-2 and GH, prednisone, budesonide, TNF inhibitors, azathioprine (Imuran), methotrexate, 6-mercaptopurine, mesalamine, and Infliximab. In an embodiment, GLP-1 receptor agonists are administered to a subject in admixture with at least one other peptide hormone selected from the group consisting of IGF-1, IGF-2 and GH.

In another of its aspects, the invention provides for the treatment of patient candidates as just identified using implanted cells that have either been conditioned in vitro or in vivo by prior incubation or treatment with a GLP-1 receptor agonist, or have been engineered genetically to produce it. Conditioning of the cells ex vivo can be achieved simply by growing the cells or tissue to be transplanted in a medium that has been supplemented with a growth-promoting amount of the GLP-1 receptor agonist and is otherwise appropriate for culturing of those cells. The cells can, after an appropriate conditioning period, then be implanted either directly into the patient or can be encapsulated using established cell encapsulation technology, and then implanted.

Yet another aspect of the invention encompasses treating animals in vivo with GLP-1 receptor agonist in order to promote the growth of small or large intestine tissue. After subsequent enlargement of the small or large intestine these tissues may then be used in a xenotransplantation procedure. Such GLP-1 receptor agonist treatment can be advantageous carried out prior to xenotransplantation of the tissue from a non-human animal to a human because the size of the transplanted organ or tissue often limits the success of this procedure. For example, a porcine donor animal may be treated with GLP-1 receptor agonist in order to increase small or large intestine size prior to xenotransplantation of the porcine small or large intestine tissue into a human in need of this organ.

Alternatively, the cells to be implanted can be raised in vitro from a cell that has been engineered genetically to express or to over-express either the glucagon gene or, more directly, DNA coding solely for a GLP-1 receptor agonist. The sequence of such DNA can readily be determined from the amino acid sequence of the selected GLP-1 receptor agonist, with the limitation that only GLP-1 receptor agonist forms containing genetically encoded amino acids can be produced in this manner. Various viral vectors, suitable for introduction of genetic information into human cells, can be employed and will incorporate the GLP-1 receptor agonist encoding DNA under expression controls functional in the host cells. Once altered genetically, the engineered cells can then be implanted using procedures established in the art. (See, for example, Drucker et al., 1996, PNAS:USA, 93:7911-7916.)

Another aspect of the invention includes a method of treating a mammalian subject having, or at risk of developing, a condition in which functioning of the small or large intestine is impaired, enhancing functioning or preventing damage to the small or large intestine in a subject, or ameliorating inflammation of the small or large intestine in a subject, comprising administering to the subject a GLP-1 receptor agonist. In an embodiment, the amount of GLP-1 receptor agonist administered is effective to proliferate the tissue of the small or large intestine. In another embodiment, the subject is suffering from an inflammatory condition involving the small or large intestine. In another embodiment, the subject is at risk of developing an inflammatory condition involving the small or large intestine, and the amount of GLP-1 receptor agonist is effective to delay or prevent onset of the condition. In yet another embodiment, the inflammatory condition is selected from the group comprising Crohn's disease, ulcerative colitis, infectious colitis, drug or chemical-induced colitis, diverticulitis, and ischemic colitis. In another embodiment, the inflammatory condition is colitis. In still another embodiment, the subject has undergone partial or subtotal resection of the small or large intestine. In another embodiment, the GLP-1 receptor agonist is an analog of GLP-1 having enhanced small or large intestine cell proliferating activity relative to native GLP-1. In another embodiment, the GLP-1 receptor agonist is administered by oral, subcutaneous, or rectal administration. In another embodiment, the amount of GLP-1 receptor agonist administered does not significantly lower blood glucose or body weight of the subject. In one embodiment, the GLP-1 receptor agonist is exenatide. In one embodiment, the total daily dose of exenatide in a human is less than 5 μg/day. In anther embodiment, the GLP-1 receptor agonist is liraglutide. In yet another embodiment, the equivalent human dose of liraglutide is less than 0.3 mg/day.

In another aspect, a method to identify peptides useful to treat inflammatory conditions involving the small or large intestine is provided, the method comprising the steps of:
  a) obtaining an analog of a vertebrate GLP-1 peptide, the analog having at least one amino acid substitution, deletion, addition, or an amino acid with a blocking group;
  b) inducing an inflammatory condition of the intestine involving the small or large intestine in a test animal;
  c) treating the test animal having an induced inflammatory condition of the small or large intestine, with the analog using a regimen capable of eliciting an amelioration of the inflammatory condition of the small or large intestine when utilized for native GLP-1; and
  d) determining the effect of the analog on the health status or mortality of the test animal compared with control animals not receiving the peptide or determining the effect of the analog on the weight of the small or large intestine of test animals compared to control animals not receiving peptide.

In another aspect of the invention, a pharmaceutical composition is provided for the treatment of inflammatory bowel disease comprising a GLP-1 receptor agonist having proliferative and/or anti-inflammatory effects in the small or large intestine, together with a pharmaceutically acceptable carrier, excipient or vehicle. In another aspect, a pharmaceutical composition is provided for the treatment of IBD comprising a GLP-1 receptor agonist having regenerative effects in the colonic tissue, together with a pharmaceutically acceptable carrier, excipient or vehicle. In one embodiment, the GLP-1 receptor agonist is in a dose which does not significantly lower blood glucose and/or body weight of the subject. In another embodiment, the GLP-1 receptor agonist is exenatide in a dose of less than 10 μg. In another embodiment, the composition comprises multiple dosage units, wherein the total daily dosage is less than 10 μg. In another embodiment, the GLP-1 receptor agonist is liraglutide in a dose of less than 0.6 mg. In another embodiment, the composition comprises multiple dosage units, wherein the total daily dosage is less than 0.6 mg. In another embodiment, the composition is administered once daily.

In another aspect, a method of treatment is provided comprising, delivering to the small intestine of a patient in need thereof, a pharmaceutically effective amount of a GLP-1 receptor agonist, wherein the length or weight of the small intestine is increased. In another aspect, a method of treatment is provided comprising, delivering to the small or large intestine of a patient in need thereof, a pharmaceutically effective amount of a GLP-1 receptor agonist, wherein the length or weight of the small or large intestine is increased. In one embodiment, the GLP-1 receptor agonist is liraglutide. In another embodiment, the liraglutide is administered in a dose of 50 μg/kg per day or less. In another embodiment, the delivering occurs without causing significant weight loss in the patient. In another embodiment, the delivering occurs without a significant reduction in glucose tolerance.

In another aspect, a pharmaceutical composition is provided for treating inflammatory bowel disease, comprising one or more dosing units of Liraglutide, wherein the total daily dosage is 50 μg/kg per day.

The invention having been described, the following examples are offered by way of illustration and not limitation. In accordance with the above described methods and compositions, the Examples described below support the claimed invention and show that treatment of a patient with a GLP-1 receptor agonist ameliorates gastrointestinal disease.

As illustrated by the animal model data in Examples 1-5 below, the inventors have shown that treatment with DSS, exacerbates colitis in GLP-1R−/− (GLP-1 receptor knockout) mice. These findings are evidenced by a decrease in colon weight, length and body weight. Treatment with Exendin-4 (5 nmol/kg for 7 days) attenuates this condition. These findings validate the inventors' conclusions that functional GLP-1 receptors are critical components in preventing or ameliorating gastrointestinal diseases.

Based upon the animal data, treatment with liraglutide and exendin-4 results in a proliferation of intestinal cells, even in wild type mice without induced colitis. This is evidenced by an increase in colon weight after treatment with liraglutide (75 ug/kg for 7 or 14 days) or Exendin-4 (10 nmol/kg for 14 days). In addition, 1 μg for 10 days of exendin-4 increased both colon length and weight.

Results of treatment with exendin-4 and liraglutide is even more pronounced in wild type animals with DSS induced colitis. Both exendin-4 and liraglutide showed a positive effect on small and large intestine growth even at lower doses than those previously found to have a beneficial effect on glucose levels or heart disease (for liraglutide). In addition, low dose liraglutide treatment was shown to have a positive effect on bowel size without affecting glucose levels and body weight.

EXAMPLE 1

Effect of GLP-1 Receptor Agonist in GLP-1 Receptor Knockout Animals

The following animals were used in the study: WT represents wild type C57BL/6 mice (or GLP-1R+/+); GLP-1R−/− represents C57BL/6 mice with genetic disruption (knockout) of the GLP-1 receptor as described in Scrocchi L A, et al (*Nature Med* 2:1254-1258, 1996).

All data are from male mice that ranged from approximately 4 to 6 months old at the time of the experiment. All mice were maintained on a diet of standard rodent chow throughout the study. Mice were given intraperitoneal (i.p.) injections of phosphate buffered saline (PBS) or 1 µg of Exendin-4 (Ex-4) (dissolved in PBS) for 10 days. All injections were administered into the lateral aspect of the lower right quadrant of the mouse's abdomen. All injections were administered in a volume of 100 µl using an insulin syringe with a 31 gauge, 8 mm long needle. All injections were administered twice a day with the first injection given between 9 am and 10 am and the second injection given between 6 pm and 7 pm. The final injection was administered either at 7 pm the evening before sacrifice (day 10), or 4 hours prior to sacrifice on day 11. Mice that were given a final injection 4 hours prior to sacrifice on day 11 were also given an i.p. injection of glucose (1.5 g of glucose dissolved in water per kg of body weight). For bowel dissections, mice were euthanized via $CO_2$ inhalation and their body weight was obtained. The GI tract from the stomach to the distal portion of the large bowel (including the pancreas) was removed from the animal. The length of the large bowel (from the caecum to the rectum) was measured using a ruler placed on a horizontal surface. Luminal contents were removed from the large bowel by flushing with PBS using a 60 cc syringe attached to a p200 pipette tip. Mesenteric fat and pancreatic tissue were dissected away from the large and small bowel. The bowel segments were blotted to remove excess PBS and then weighed. N=2-4 mice/group. The results are shown in FIGS. 1A and 1B. FIGS. 1A and B are graphs illustrating data from WT and GLP-1R knockout mice treated with the GLP-1 receptor agonist Exendin-4. Exendin-4 increased colon length and weight in WT but not in GLP-1R knockout mice.

EXAMPLE 2

Effect of GLP-1 Receptor Agonist in Animals

Figure 2:
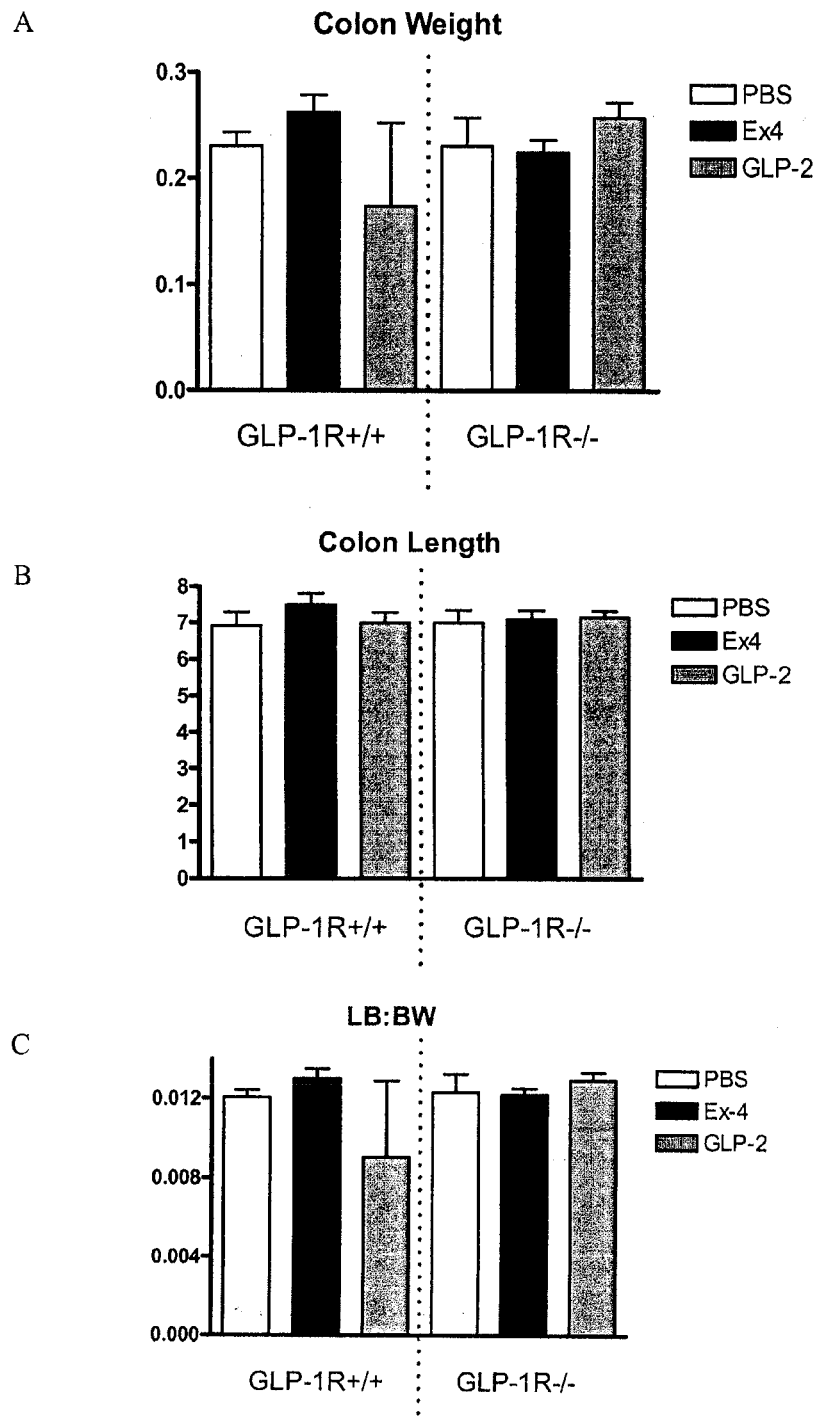
FIG. 2A-2C are graphs of colon weight, colon length, and ratio of bowel weight to body weight, respectively showing data from WT and GLP-1R−/− mice treated with Exendin-4 or GLP-2. Mice were given subcutaneous (s.c.) injections of PBS (white bars), 10 nmol/kg of exendin-4 (Ex-4) (dissolved in PBS) (black bars), or 5 μg of Gly-2-GLP-2 (dissolved in PBS) (grey bars) for 10 days. See protocol in Example 2.
Figure 3:
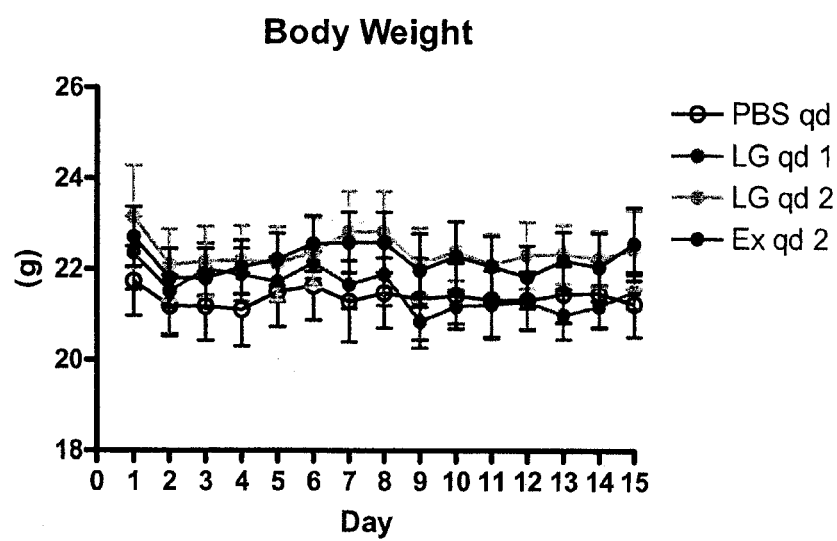
Figure 3:
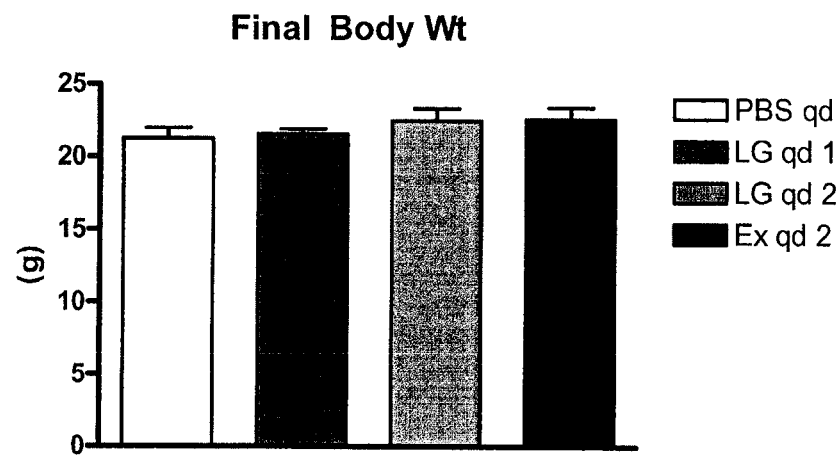
Figure 4:
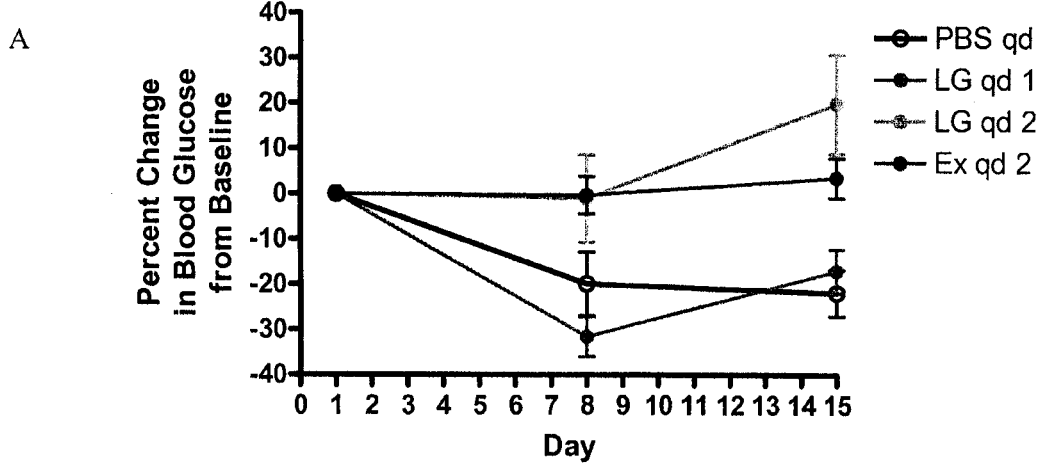
Figure 4:
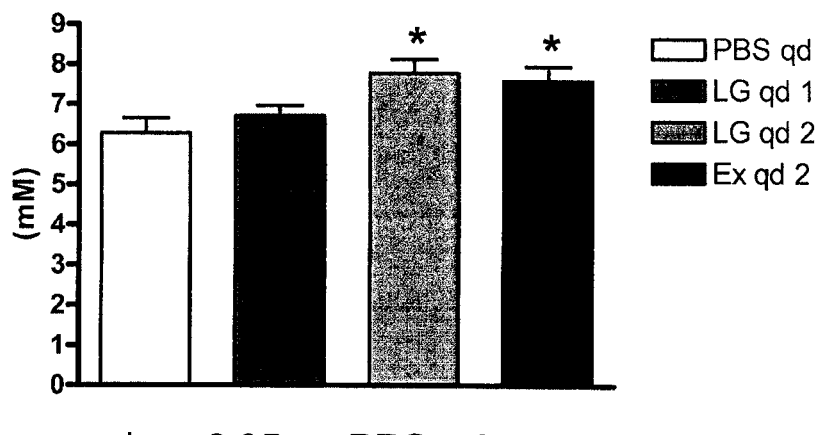
Figure 5:
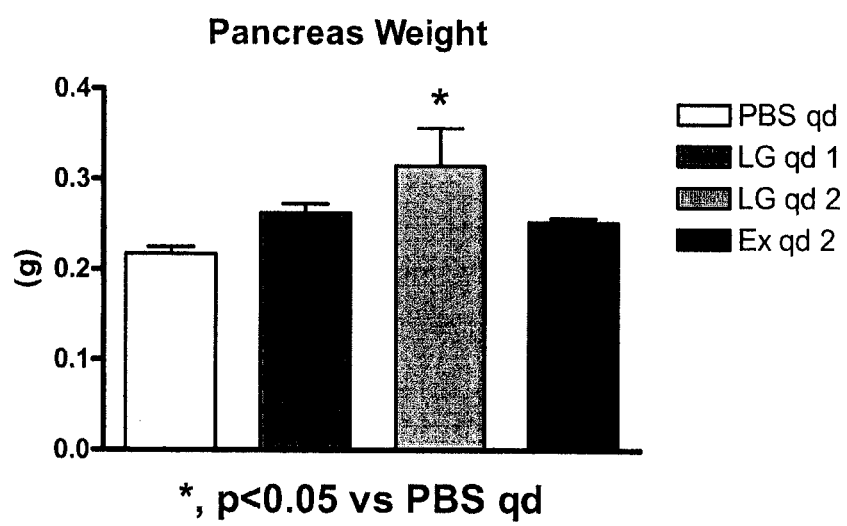
Figure 5:
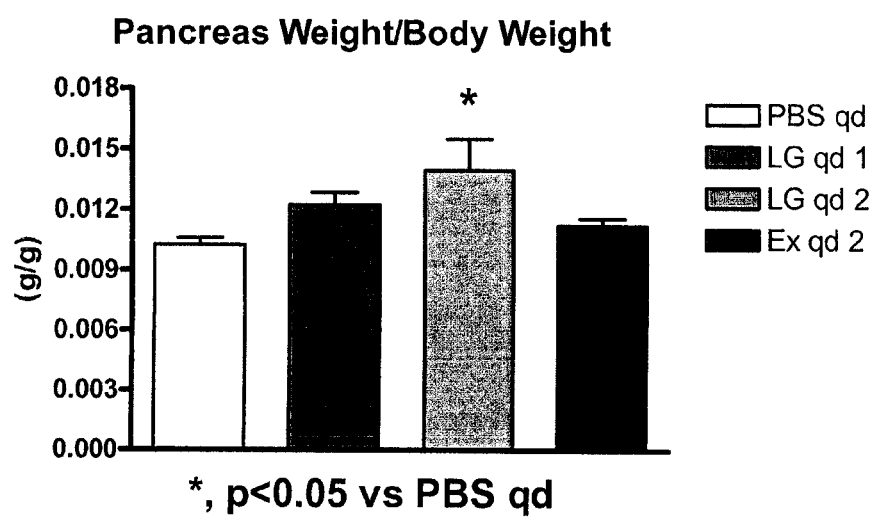
Figure 6:
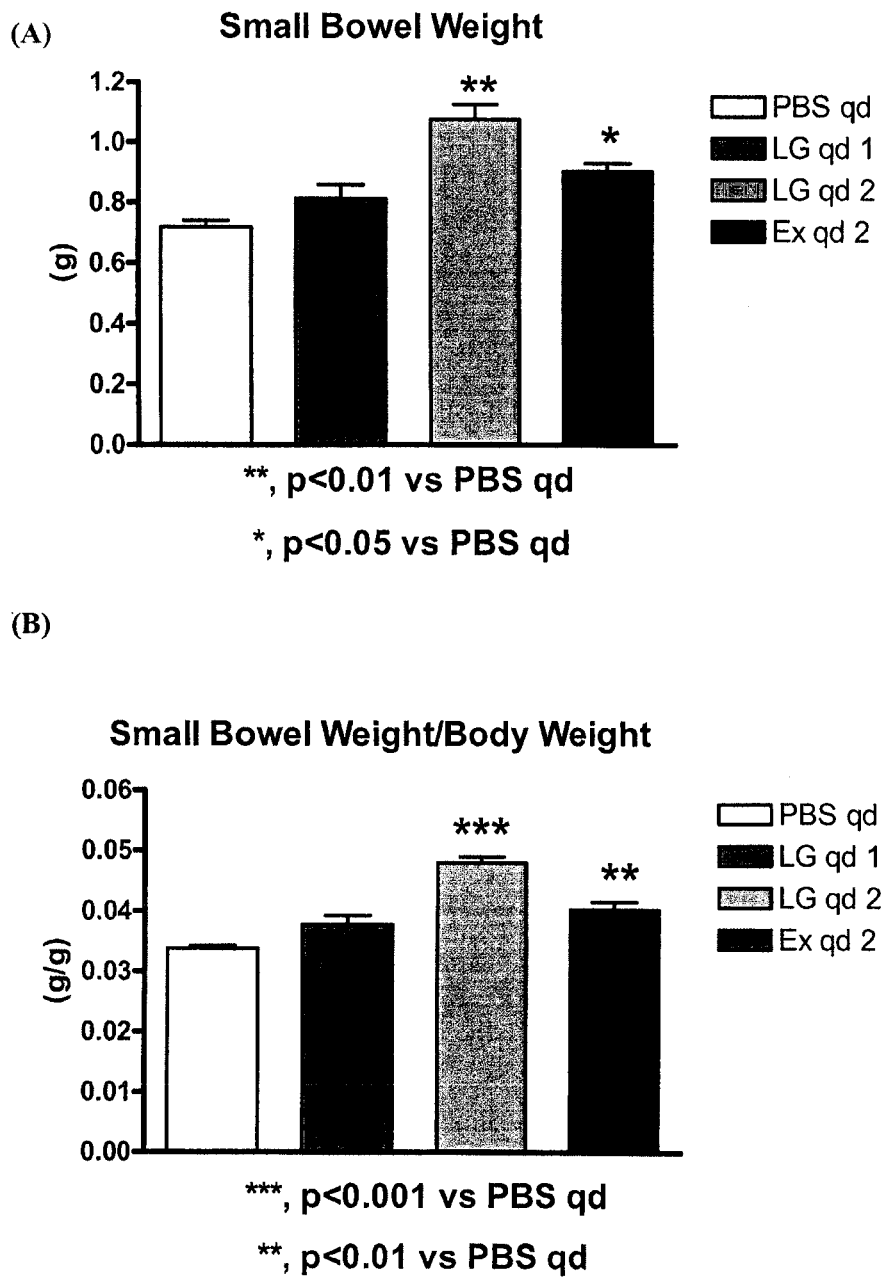
Figure 6:
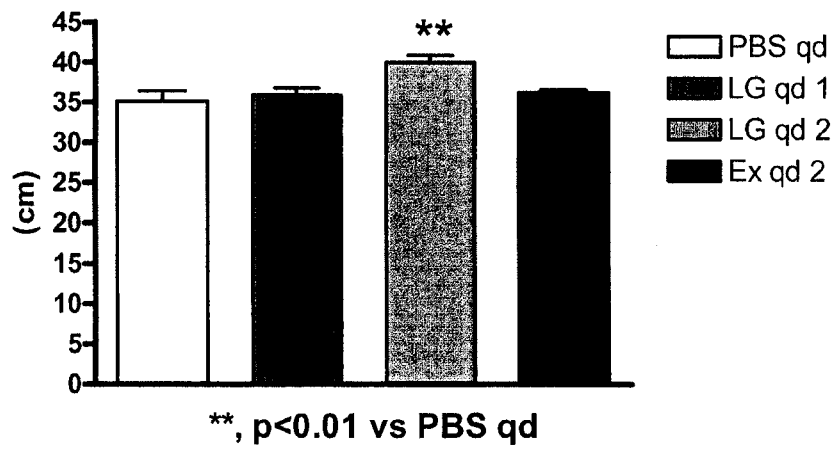
Figure 6:
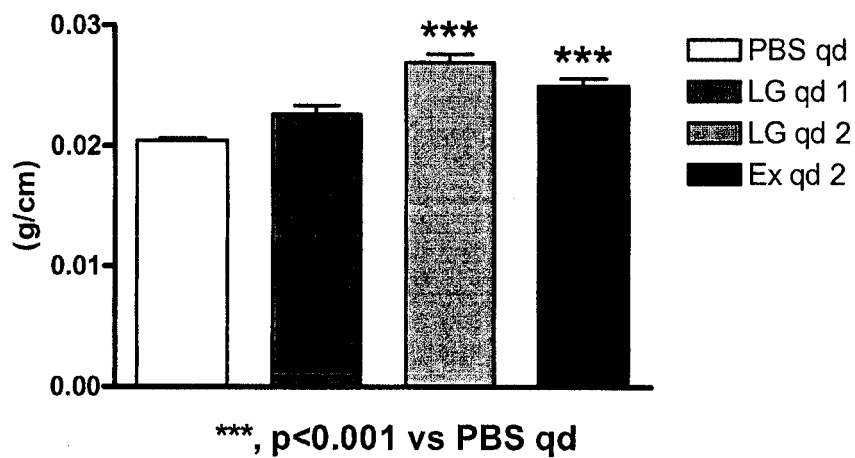
Figure 7:
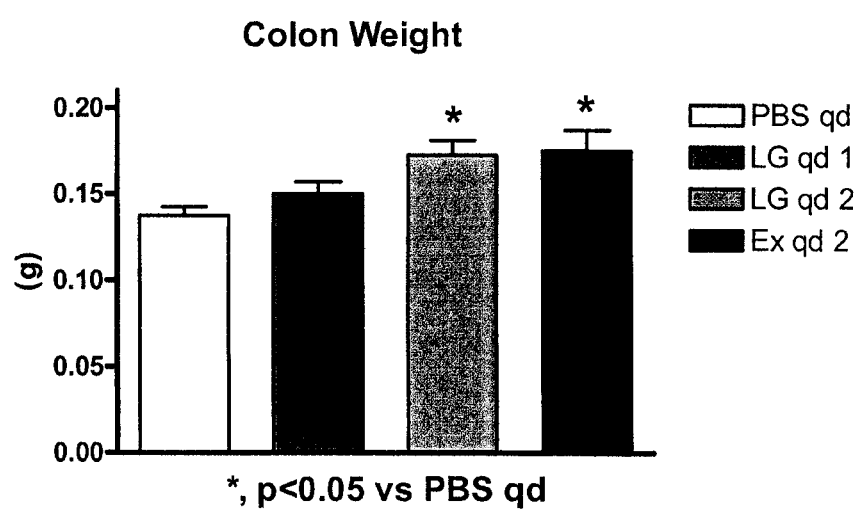
Figure 7:
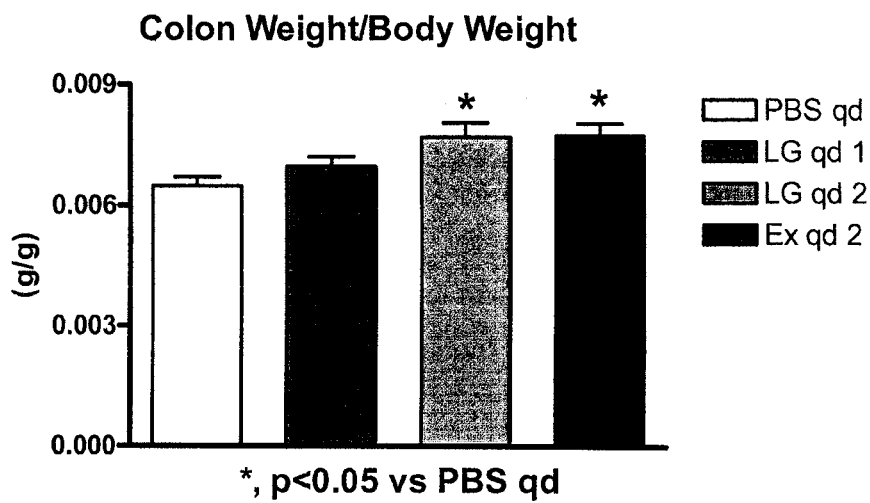
Figure 7:
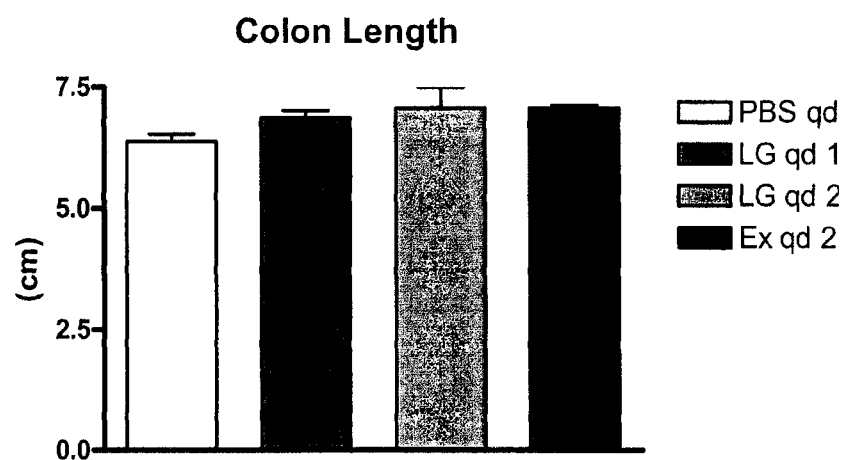
Figure 7:
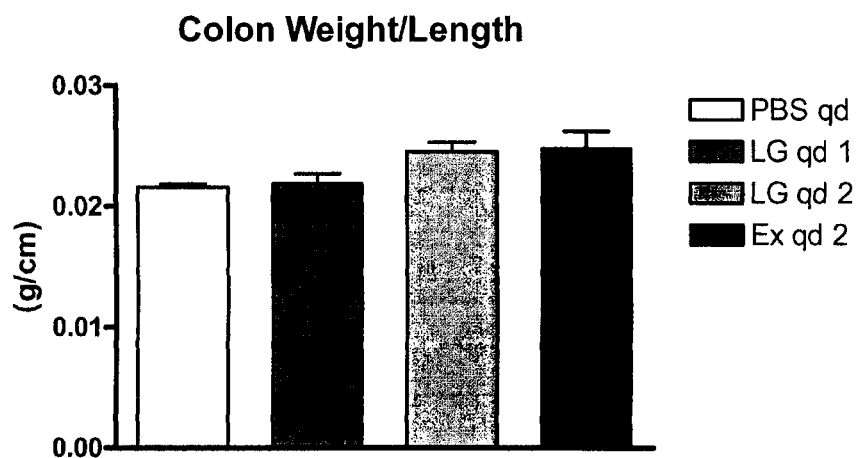

All mice were maintained on a standard rodent diet throughout the study. All data are from female C57BL/6 mice that were approximately 11 weeks old at the time of sacrifice. Mice were given subcutaneous (s.c.) injections of PBS, 10 nmol/kg of exendin-4 (Ex-4) (dissolved in PBS), or 5 µg of Gly-2-GLP-2 (dissolved in PBS) for 10 days, commencing when mice were either 10 weeks of age or had a body weight of 18-20 g. The dosing volume was 100 µl per mouse. All injections were administered subcutaneously at the back of the neck, between the animal's shoulders using an insulin syringe with a 31 gauge, 8 mm long needle. All injections were administered twice a day with the first injection given at 8 am and the second injection given between 5 pm and 6 pm. The dosing schedule commenced with the evening dose on day 1 and ended with the evening dose on day 10. All mice were euthanized on day 11. Brdu (100 mg/kg) was administered via i.p injection 2 hrs prior to sacrifice. For bowel dissections, mice were euthanized via $CO_2$ inhalation and their body weight was obtained. The GI tract from the stomach to the distal portion of the large bowel (including the pancreas) was removed from the animal. The length of the entire small intestine from the pylorus to the caecum was measured by suspending the section vertically and attaching a 1 g weight to the bottom end of the intestine to provide uniform tension. The length of the small intestine was measured on a vertical ruler. The length of the large bowel (from the caecum to the rectum) was measured using a ruler placed on a horizontal surface. Luminal contents were removed from both the large and small bowel by flushing with PBS using a 60 cc syringe attached to a p200 pipette tip. Mesenteric fat and pancreatic tissue were dissected away from the large and small bowel. The bowel segments were blotted to remove excess PBS and then weighed. N=3-6 mice/group. The results are shown in FIGS. 2A-2C. FIGS. 2A-2C are graphs illustrating data from WT and GLP-1R−/− mice treated with Exendin-4 or GLP-2. Exendin-4 increased colon weight and length in WT but not in GLP-1R−/− mice.

EXAMPLE 3

Study to Determine Efficacy of GLP-1 Receptor Agonists when Administered Once Per Day (qd)

The following materials and methods were used in the study described in this example.

All mice used in the study were 10-week old WT female mice on the C57B1/6 genetic background. The mice were maintained on regular drinking water and a standard rodent chow diet. The following four groups of mice were included in this study:

(i) PBS qd—this group was given ip injections of 100 µl of phosphate buffered saline (PBS) once per day for 14 days (ii) LG qd 1—this group was given ip injections of 100 µl of PBS once per day for 7 days and then 75 µg/kg of Liraglutide (LG) once per day for 7 days (iii) LG qd 2—this group was given ip injections of 75 µg/kg of Liraglutide (LG) once per day for 14 days (iv) Ex qd 2—this group was given ip injections of 10 nmol/kg of Exendin-4 (Ex) once per day for 14 days All injections were given once per day, and were administered ip using a 31 g insulin syringe with an 8 mm long needle in a final volume that ranged between 84-125 µl. The body weight and food intake were determined daily. Non-fasting blood glucose levels were measured using a hand-held glucometer on day 1 (prior to the first injection), day 8, and day 15 (day of sacrifice). After 14 days of treatment, all mice were sacrificed by $CO_2$ asphyxiation on day 15 (mice did not receive any injections on the day of sacrifice). The entire pancreas was removed and weighed. The entire small bowel was removed and then suspended vertically with a 1 g weight attached to the distal portion of the small bowel (to provide uniform tension). Small bowel length was determined using a vertical ruler and then flushed with ice-cold PBS, blotted dry and weighed. The entire colon was removed and colon length was determined by measuring with a ruler placed on a horizontal surface. The colon was then flushed with ice-cold PBS, blotted dry and weighed. All statistical analyses were done by one-way ANOVA with Bonferroni's Multiple Comparison Post-Test using GraphPad Prism software (version 4), n=4 mice/group.

The results are illustrated in FIGS. 3A through 7D which are described in detail below.

FIG. 3A depicts the average daily body weight per treatment group. (g=grams). PBS qd mice were given ip injections of 100 µl of phosphate buffered saline (PBS) once per day for 14 days. LG qd 1 mice were given ip injections of 100 µl of PBS once per day for 7 days and then 75 µg/kg of Liraglutide (LG) once per day for 7 days. LG qd 2mice were given ip injections of 75 µg/kg of Liraglutide (LG) once per day for 14 days. Ex qd 2 mice were given ip injections of 10 nmol/kg of Exendin-4 (Ex) once per day for 14 days.

FIG. 3B depicts the average body weight per treatment group on the day of sacrifice. (g=grams). PBS qd mice were given ip injections of 100 ul of phosphate buffered saline (PBS) once per day for 14 days; LG qd 1 mice were given ip injections of 100 μl of PBS once per day for 7 days and then 75 μg/kg of Liraglutide (LG) once per day for 7 days; LG qd 2 mice were given ip injections of 75 μg/kg of Liraglutide (LG) once per day for 14 days; Ex qd 2 mice were given ip injections of 10 nmol/kg of Exendin-4 (Ex) once per day for 14 days (n=4 mice/group).

FIGS. 3A-3B illustrate that, relative to control (PBS)-treated mice, these treatments do not have a significant effect on body weight. FIG. 4A depicts the average percent change in non-fasting blood glucose level from baseline level (day 1) per treatment group. FIG. 4B depicts the average non-fasting blood glucose level per treatment group on the day of sacrifice (mM=millimolar). Non-fasting blood glucose levels were measured using a hand-held glucometer on day 1 (prior to the first injection), day 8, and day 15 (day of sacrifice). PBS qd mice were given ip injections of 100 μl of phosphate buffered saline (PBS) once per day for 14 days; LG qd 1 mice were given ip injections of 100 μA of PBS once per day for 7 days and then 75 μg/kg of Liraglutide (LG) once per day for 7 days; LG qd 2 mice were given ip injections of 75 μg/kg of Liraglutide (LG) once per day for 14 days; and, Ex qd 2 mice were given ip injections of 10 nmol/kg of Exendin-4 (Ex) once per day for 14 days. (n=4 mice/group). All statistical analyses were done by one-way ANOVA with Bonferroni's Multiple Comparison Post-Test using GraphPad Prism software (version 4).

FIGS. 4A-4B illustrate that, relative to control (PBS)-treated mice, once a day Liraglutide treatment (75 μg/kg ip) for one week does not alter non-fasting blood glucose levels, whereas once a day Liraglutide treatment (75 μg/kg ip) for two weeks or once a day Exendin-4 treatment (10 nmol/kg ip) for two weeks significantly increased blood glucose levels.

FIG. 5A depicts the average weight of the total pancreas per treatment group. FIG. 5B depicts the average, per treatment group, of the weight of the total pancreas per gram of total body weight (g=grams). PBS qd mice were given ip injections of 100 μl of phosphate buffered saline (PBS) once per day for 14 days; LG qd 1 mice were given ip injections of 100 μl of PBS once per day for 7 days and then 75 μg/kg of Liraglutide (LG) once per day for 7 days; LG qd 2 mice were given ip injections of 75 μg/kg of Liraglutide (LG) once per day for 14 days; Ex qd 2 mice were given ip injections of 10 nmol/kg of Exendin-4 (Ex) once per day for 14 days (n=4 mice/group). All statistical analyses were done by one-way ANOVA with Bonferroni's Multiple Comparison Post-Test using GraphPad Prism software (version 4).

FIGS. 5A and B illustrate that, relative to control (PBS)-treated mice, only once a day Liraglutide treatment (75 ip) for two weeks significantly increases total pancreas weight as well as pancreas weight per gram of body weight.

FIG. 6A, depicts the average weight of the entire small bowel per treatment group; FIG. 6B depicts the average, per treatment group, of the weight of the entire small bowel per gram of total body weight; FIG. 6C depicts the average length of the entire small bowel per treatment group; and FIG. 6D depicts the average, per treatment group, of the weight of the small bowel per unit of small bowel length. (g=grams; cm=centimeters). For FIGS. 6A-6D: PBS qd mice were given ip injections of 100 μl of phosphate buffered saline (PBS) once per day for 14 days; LG qd 1 mice were given ip injections of 100 μl of PBS once per day for 7 days and then 75 μg/kg of Liraglutide (LG) once per day for 7 days; LG qd 2 mice were given ip injections of 75 μg/kg of Liraglutide (LG) once per day for 14 days; Ex qd 2 mice were given ip injections of 10 nmol/kg of Exendin-4 (Ex) once per day for 14 days (n=4 mice/group). All statistical analyses were done by one-way ANOVA with Bonferroni's Multiple Comparison Post-Test using GraphPad Prism software (version 4). FIGS. 6A-6D illustrate that, relative to control (PBS)-treated mice, only once a day Liraglutide treatment (75 ug/kg ip) for two weeks significantly increases small bowel length. However, both once a day Liraglutide treatment (75 ug/kg ip) for two weeks and once a day Exendin-4 treatment (10 nmol/kg ip) for two weeks increase total small bowel weight, total small bowel weight per gram of total body weight, and the weight of the small bowel per unit of small bowel length.

FIG. 7A depicts the average weight of the entire colon per treatment group; FIG. 7B depicts the average, per treatment group, of the weight of the entire colon per gram of total body weight; FIG. 7C depicts the average length of the entire colon per treatment group; and FIG. 7D depicts the average, per treatment group, of the weight of the colon per unit of colon length. (g=grams; cm=centimeters). For FIGS. 7A-7D: PBS qd mice were given ip injections of 100 μl of phosphate buffered saline (PBS) once per day for 14 days; LG qd 1 mice were given ip injections of 100 μl of PBS once per day for 7 days and then 75 ug/kg of Liraglutide (LG) once per day for 7 days; LG qd 2 mice were given ip injections of 75 ug/kg of Liraglutide (LG) once per day for 14 days; Ex qd 2 mice were given ip injections of 10 nmol/kg of Exendin-4 (Ex) once per day for 14 days (n=4 mice/group). All statistical analyses were done by one-way ANOVA with Bonferroni's Multiple Comparison Post-Test using GraphPad Prism software (version 4). FIGS. 7A-7D illustrate that, relative to control (PBS)-treated mice, these treatments do not have a significant effect on colon length or the weight of the colon per unit of colon length. However, both once a day Liraglutide treatment (75 μg/kg ip) for two weeks and once a day Exendin-4 treatment (10 nmol/kg ip) for two weeks increase total colon weight and total colon weight per gram of total body weight.

EXAMPLE 4

GLP-1 Receptor Signaling in an Experimental Model of Intestinal Injury: Dextran Sodium Sulfate(DSS)-Induced Colitis An animal model of intestinal inflammation induced by DSS was used in the study described in this example. DSS is directly toxic to gut epithelial cells; there is direct damage to the epithelial barrier which affects the integrity of the mucosal barrier. Exposure to luminal contents leads to activation of the innate immune system (macrophages/dendritic cells/neutrophils) and the release of pathogenic cytokines/chemokines. The acquired immune system (T cells and B cells) is also activated.

An inflammatory response that leads to injury of the epithelium provides clinical features such as weight loss, loose stools/diarrhea, and rectal bleeding and histological features such as colon shortening and thickening, tissue edema, reductions in colon crypt depth and area, reductions in epithelial cell proliferation, loss of goblet cells, focal crypt lesions, infiltration of inflammatory cells in lesion areas and often severe ulceration.

FIGS. 8A-8C illustrate that GLP-1R−/− mice lose more weight than wild-type mice during DSS-treatment. All mice were 10-week old female WT or GLP-1R−/− littermates on C57B1/6 background. Mice were maintained on either regular drinking water or water supplemented with 3% DSS for a total of one week. After one week of normal water or 3% DSS-supplemented drinking water, all mice were sacrificed by $CO_2$ asphyxiation. Colons were removed and their lengths were determined by measuring with a ruler placed on a horizontal surface. Colons were then flushed with ice-cold PBS, blotted dry and weighed. Statistical analyses were done by one-way ANOVA with Bonferroni's Multiple Comparison Post-Test or unpaired Student's t-test using GraphPad Prism software (version 4) (n=9-12 mice/group).

FIGS. 9A-9D illustrate that colon weight is reduced to a greater degree in GLP-1R−/− mice during DSS-treatment. All mice were 10-week old female WT or GLP-1R−/− littermates on C57B1/6 background. Mice were maintained on either regular drinking water or water supplemented with 3% DSS for a total of one week. After one week of normal water or 3% DSS-supplemented drinking water, all mice were sacrificed by $CO_2$ asphyxiation. Colons were removed and their lengths were determined by measuring with a ruler placed on a horizontal surface. Colons were then flushed with ice-cold PBS, blotted dry and weighed. Statistical analyses were done by one-way ANOVA with Bonferroni's Multiple Comparison Post-Test or unpaired Student's t-test using GraphPad Prism software (version 4) (n=9-12 mice/group).

Photomicrographs (not shown) show that DSS colitis is exacerbated in GLP-1R−/− vs. WT mice. All mice were 10-week old female WT or GLP-1R−/− littermates on C57B1/6 background. Mice were maintained on either regular drinking water or water supplemented with 3% DSS for a total of one week. After one week of normal water or 3% DSS-supplemented drinking water, all mice were sacrificed by $CO_2$ asphyxiation. Colons were removed and their lengths were determined by measuring with a ruler placed on a horizontal surface. Colons were then flushed with ice-cold PBS, blotted dry and weighed. Colons were divided into 3 equal sections representing proximal (closest to caecum), middle, and distal colon (closest to rectum). The proximal colon section was snap frozen in liquid nitrogen to be used for RNA isolation. The middle colon section was snap frozen in liquid nitrogen to be used for protein isolation and assay of myeloperoxidase (MPO) activity. The distal colon section was fixed in 10% neutral buffered formalin for 24 hrs, transferred to 70% ethanol and then processed, imbedded, sectioned and stained for hematoxylin and eosin using standard protocols. (n=9-12 mice/group).

FIGS. 10A-10C illustrate that exendin-4 increases small bowel size in mice maintained on water DSS. All mice were 10-week old WT female on the C57B1/6 genetic background. Mice were maintained on either regular drinking water or water supplemented with 3% DSS for a total of one week. Mice were given ip injections of either phosphate buffered saline (PBS) or 5 nmol/kg of Exendin-4 (Ex-4) BID. PBS or Ex-4 injections commenced at the same time that mice were started on normal drinking water or water supplemented with 3% DSS. Injections were administered using a 31 g insulin syringe with an 8 mm long needle and in a final volume that ranged between 75-100 μl. Body weights were determined daily. After one week of treatment, all mice were sacrificed by $CO_2$ asphyxiation (mice did not receive PBS or Ex-4 injections on the day of sacrifice). Small intestines were removed and then suspended vertically with a 1 g weight attached to the distal portion of the small bowel (to provide uniform tension). Small bowel length was determined using a vertical ruler. Small intestines were then flushed with ice-cold PBS, blotted dry and weighed. Statistical analyses were done by one-way ANOVA with Bonferroni's Multiple Comparison Post-Test or using GraphPad Prism software (version 4). (n=4 mice/group).

FIGS. 11A-11C illustrate that exendin-4 increases colon weight in DSS-treated mice. All mice were 10-week old WT female on the C57B1/6 genetic background. Mice were maintained on either regular drinking water or water supplemented with 3% DSS for a total of one week. Mice were given ip injections of either phosphate buffered saline (PBS) or 5 nmol/kg of Exendin-4 (Ex-4) BID. PBS or Ex-4 injections commenced at the same time that mice were started on normal drinking water or water supplemented with 3% DSS. Injections were administered using a 31 g insulin syringe with an 8 mm long needle and in a final volume that ranged between 75-100 μl. Body weights were determined daily. After one week of treatment, all mice were sacrificed by $CO_2$ asphyxiation (mice did not receive PBS or Ex-4 injections on the day of sacrifice). Colons were removed and their lengths were determined by measuring with a ruler placed on a horizontal surface. Colons were then flushed with ice-cold PBS, blotted dry and weighed. Statistical analyses were done by one-way ANOVA with Bonferroni's Multiple Comparison Post-Test using GraphPad Prism software (version 4) (n=4 mice/group).

Photomicrographs (not shown) illustrate that DSS colitis is attenuated in exendin-4 versus PBS treated WT mice. All mice were 10-week old WT female on the C57B1/6 genetic background. Mice were maintained on either regular drinking water or water supplemented with 3% DSS for a total of one week. Mice were given ip injections of either phosphate buffered saline (PBS) or 5 nmol/kg of Exendin-4 (Ex-4) BID. PBS or Ex-4 injections commenced at the same time that mice were started on normal drinking water or water supplemented with 3% DSS. Injections were administered using a 31 g insulin syringe with an 8 mm long needle and in a final volume that ranged between 75-100 μl. Body weights were determined daily. After one week of treatment, all mice were sacrificed by $CO_2$ asphyxiation (mice did not receive PBS or Ex-4 injections on the day of sacrifice). Colons were removed and their lengths were determined by measuring with a ruler placed on a horizontal surface. Colons were then flushed with ice-cold PBS, blotted dry and weighed. Colons were divided into 3 equal sections representing proximal (closest to caecum), middle, and distal colon (closest to rectum). The proximal colon section was snap frozen in liquid nitrogen to be used for RNA isolation. The middle colon section was snap frozen in liquid nitrogen to be used for protein isolation and assay of myeloperoxidase (MPO) activity. The distal colon section was fixed in 10% neutral buffered formalin for 24 hrs, transferred to 70% ethanol and then, processed, imbedded, sectioned and stained for hematoxylin and eosin using standard protocols. (n=4 mice/group).

Figure 13:
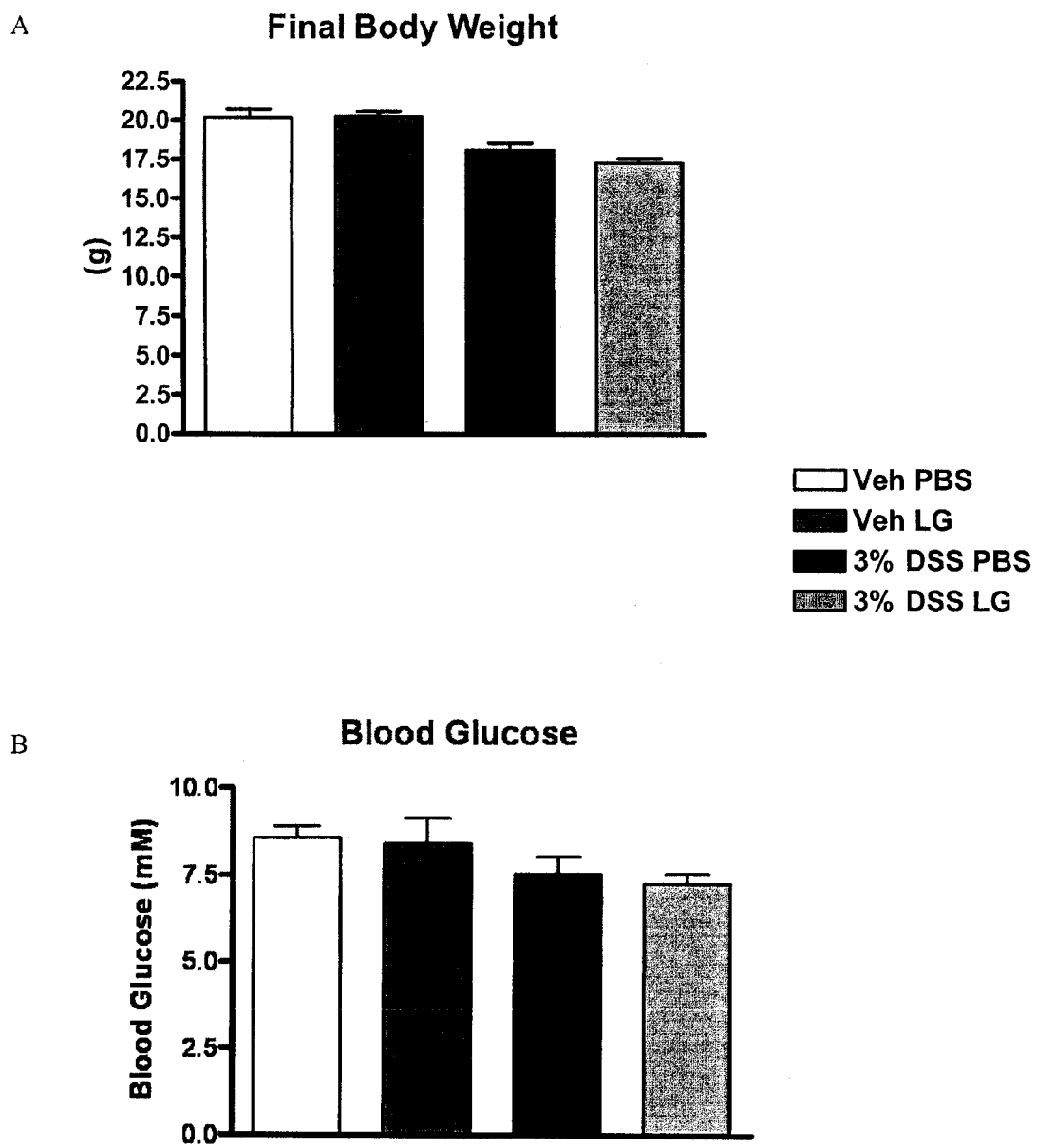
Figure 14:
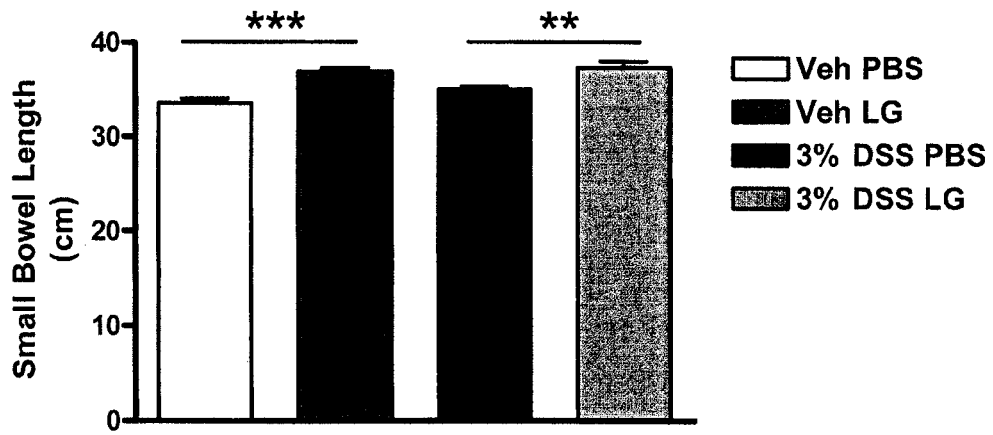
Figure 14:
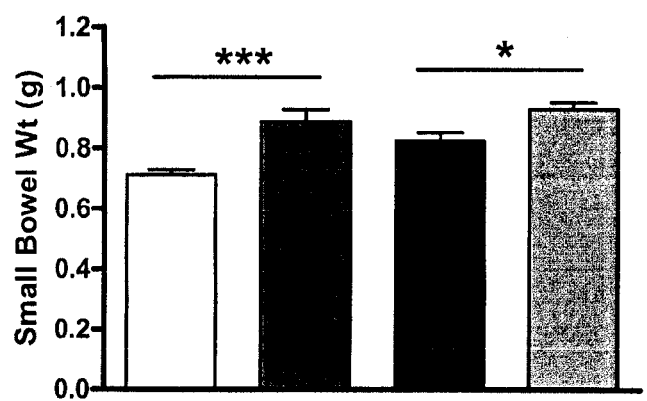
Figure 14:
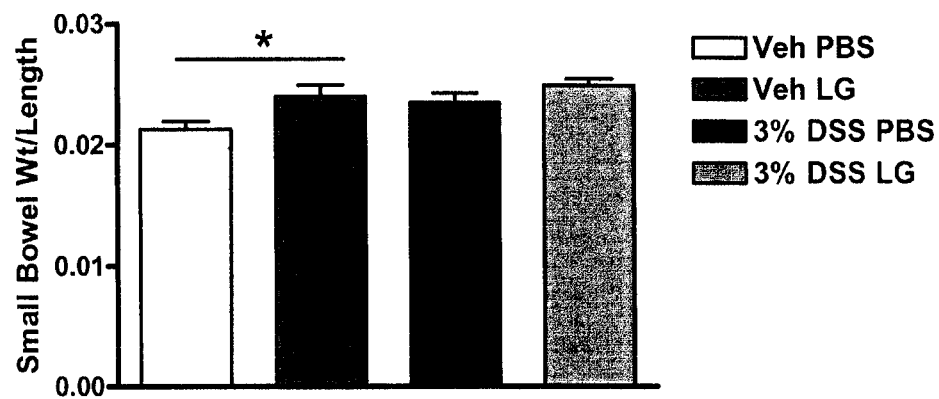
Figure 14:
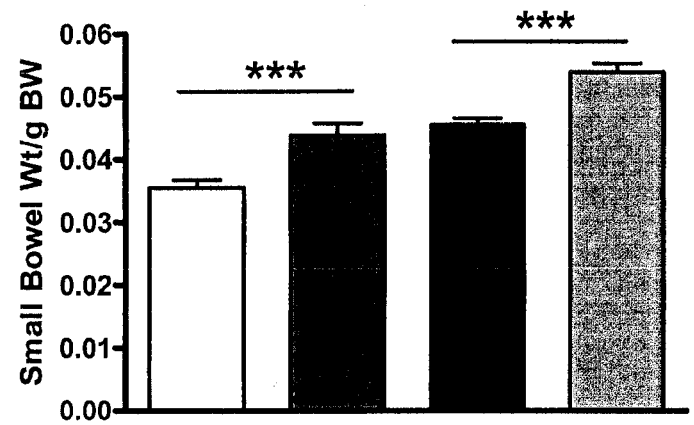
Figure 15:
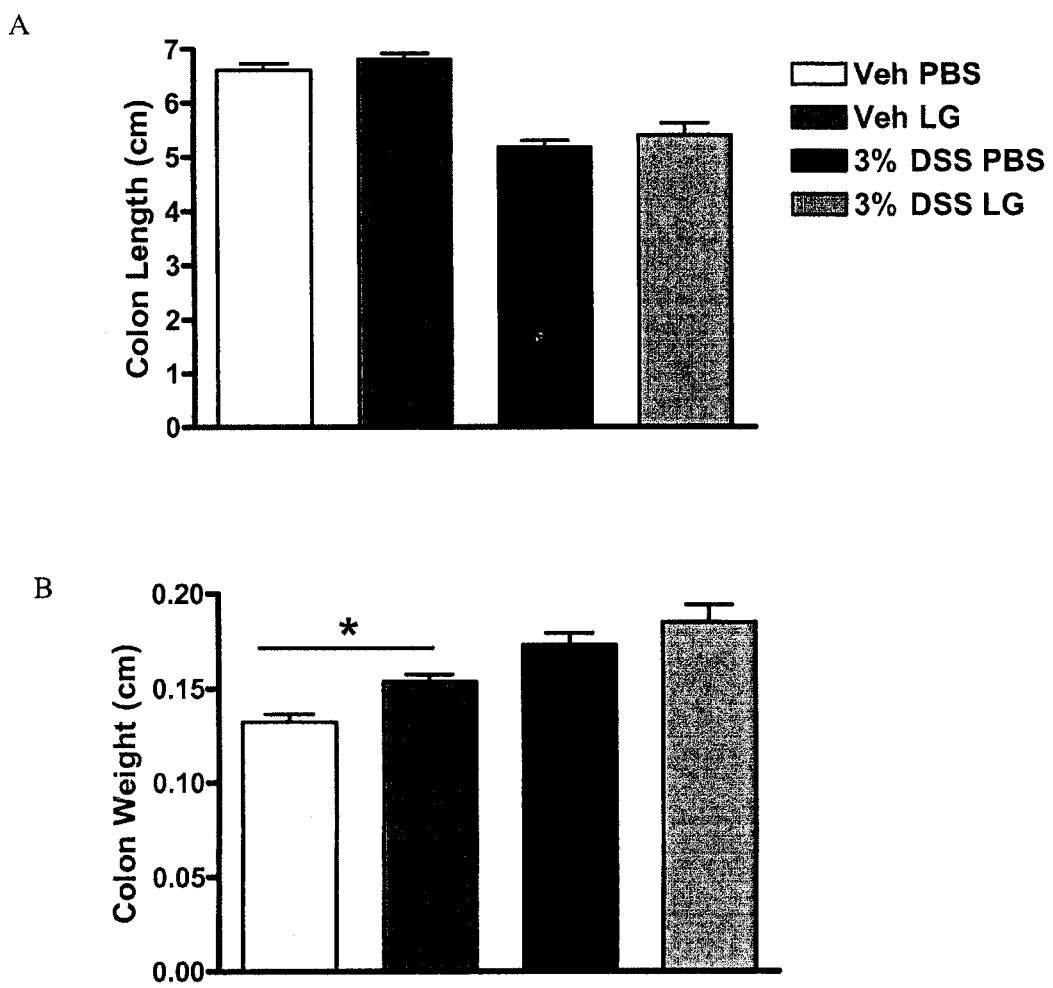
Figure 15:
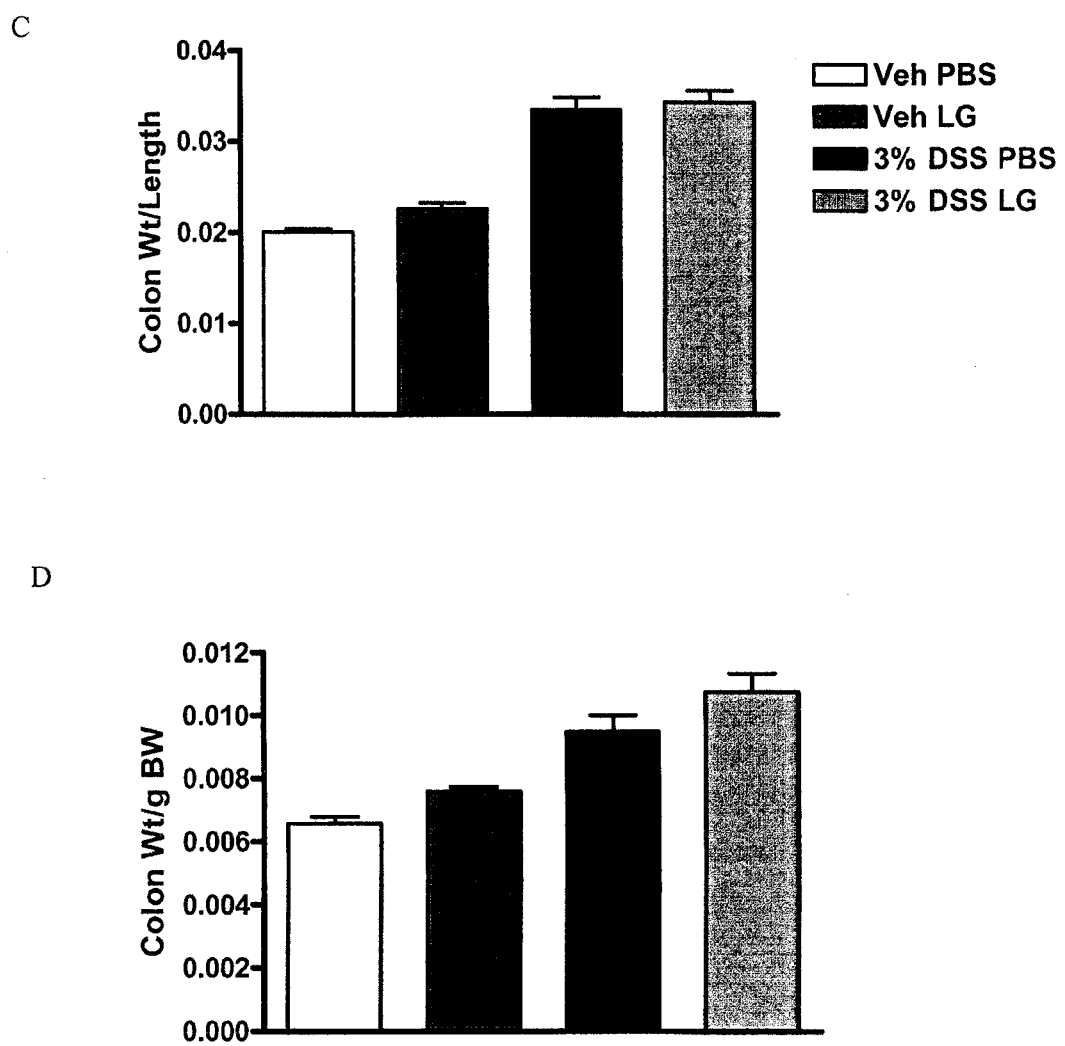
Figure 16:
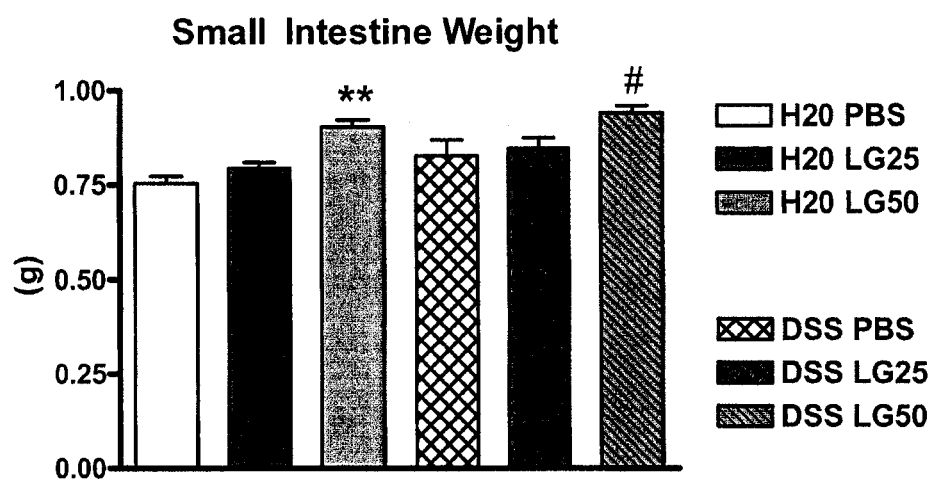
Figure 16:
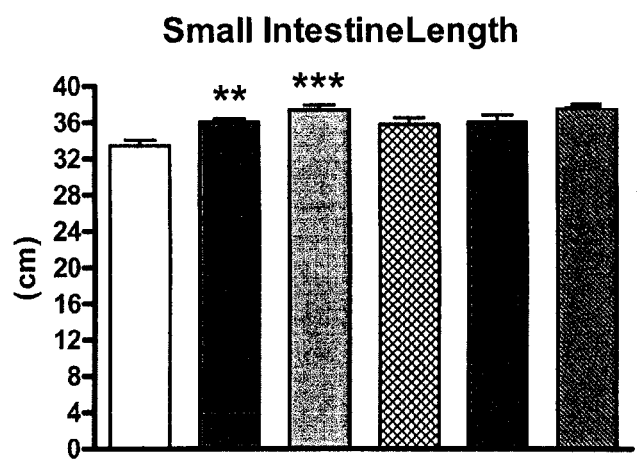
Figure 16:
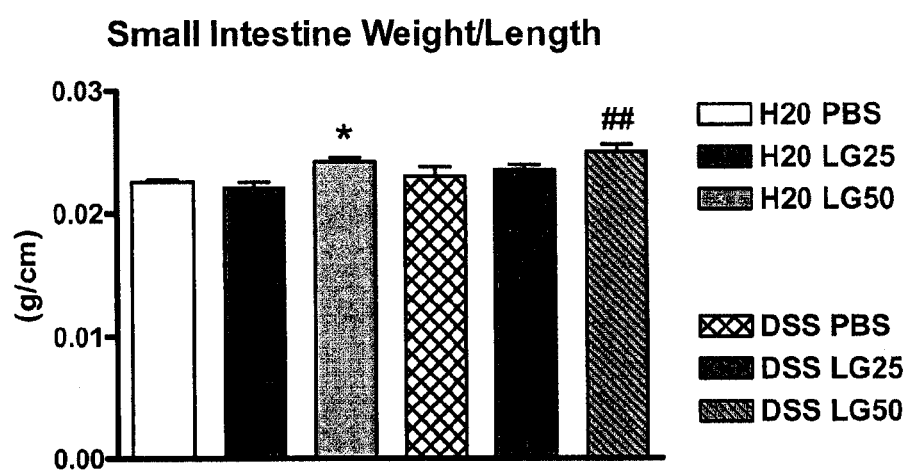
Figure 16:
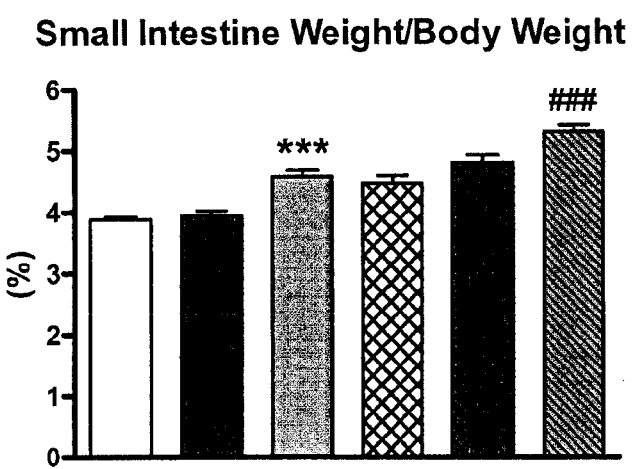

FIGS. 12A and 12B show that there is no difference in final body weight or blood glucose levels in exendin-4-treated versus PBS-treated mice. All mice were 10-week old WT female on the C57B1/6 genetic background. Mice were maintained on either regular drinking water or water supplemented with 3% DSS for a total of one week. Mice were given ip injections of either phosphate buffered saline (PBS) or 5 nmol/kg of Exendin-4 (Ex-4) BID. PBS or Ex-4 injections commenced at the same time that mice were started on normal drinking water or water supplemented with 3% DSS. Injections were administered using a 31 g insulin syringe with an 8 mm long needle and in a final volume that ranged between 75-100 μl. FIGS. 13A and 13B show that there is no difference in final body weight or blood glucose levels in liraglutide-treated versus PBS-treated mice. FIGS. 14A-14D illustrate that liraglutide increases small bowel size in mice maintained on water±DSS. FIGS. 15A-15D illustrate that liraglutide increases colon weight in mice maintained on water; colon weight also trended higher in liraglutide-treated mice exposed to 3% DSS. For FIGS. 13A-15D, all mice were 10-week old WT female on the C57B1/6 genetic background. Mice were maintained on either regular drinking water or water supplemented with 3% DSS for a total of one week. Mice were given s.c. injections of either phosphate buffered saline (PBS) or 75 ug/kg of Liraglutide (LG) BID. PBS or LG injections commenced at the same time that mice were started on normal drinking water or water supplemented with 3% DSS. Injections were administered using a 31 g insulin syringe with an 8 mm long needle and in a final volume that ranged between 75-100 µl. Body weights, food intake, and water intake were determined daily. After one week of treatment, all mice were sacrificed by $CO_2$ asphyxiation (mice did not receive PBS or LG injections on the day of sacrifice). Small intestines were removed and then suspended vertically with a 1 g weight attached to the distal portion of the small bowel (to provide uniform tension). Small bowel length was determined using a vertical ruler. Small intestines were then flushed with ice-cold PBS, blotted dry and weighed. Colons were removed and their lengths were determined by measuring with a ruler placed on a horizontal surface. Colons were then flushed with ice-cold PBS, blotted dry and weighed. Statistical analyses were done by one-way ANOVA with Bonferroni's Multiple Comparison Post-Test using GraphPad Prism software (version 4). (n=4 mice/group).

EXAMPLE 5

The data illustrated in FIGS. 16A-23B show that (a) low dose liraglutide (GLP-1 receptor agonist) has beneficial effects on the gut at doses that do not affect glucose and body weight (the more traditional metabolic endpoints associated with GLP-1 therapy); (b) the GLP-1R agonist exendin-4, increases the expression of IGF-1, a protein with known therapeutic benefit, in the colon; and (c) GLP-1R−/− mice exhibit multiple defects in inflammation and growth-factor-related gene expression consistent with the loss of anti-inflammatory and trophic GLP-1R-dependent pathway.

FIGS. 16A-16D illustrate that doses of Liraglutide lower than those that have shown glucose lowering or cardioprotective effects in rodents [Rolin B, et al, 2002; Noyan-Ashraf M H, et al, 2009; Porter D W et al, 2010; Irwin N et al, 2010; and Gault V A et al, 2011] are able to increase small intestine size (small intestine weight and length) in wild-type mice compared to PBS-treated mice.

All mice were 10-week old wild-type female mice on the C57Bl/6 genetic background. Mice were maintained on a standard rodent chow diet and either regular drinking water or water supplemented with 3% DSS for a total of one week. Mice were given subcutaneous injections of either phosphate buffered saline (PBS), 25 µg/kg of Liraglutide (LG) BID, or 50 µg/kg of LG BID for one week. PBS or LG injections commenced at the same time that mice were started on normal drinking water or water supplemented with 3% DSS. Injections were administered using a 31 g insulin syringe with an 8 mm long needle and in a final volume that ranged between 85-110 µl. Body weights, food intake, and water intake were determined daily. After one week of treatment, all mice were sacrificed by $CO_2$ asphyxiation (mice did not receive PBS or LG injections on the day of sacrifice). Small intestines were removed and then suspended vertically with a 1 g weight attached to the distal portion of the small intestine (to provide uniform tension). Small intestine length was determined using a vertical ruler. Luminal contents were removed from the small bowel by flushing with ice-cold PBS using a 60 cc syringe attached to a p200 pipette tip. Mesenteric fat and pancreatic tissue were dissected away from the small intestine. The small intestine was blotted to remove excess PBS and then weighed. Statistical analyses were done by one-way ANOVA with Bonferroni's Multiple Comparison Post-Test using GraphPad Prism software (version 4).

FIGS. 17A and 17B illustrate that there is no difference in final body weight or blood glucose level in wild-type mice treated with two different doses of Liraglutide compared to PBS-treated mice. All mice were 10-week old female wild-type mice on the C57Bl/6 genetic background. Mice were maintained on a standard rodent chow diet and either regular drinking water or water supplemented with 3% DSS for a total of one week. Mice were given s.c. injections of either phosphate buffered saline (PBS), 25 µg/kg of Liraglutide (LG) BID, or 50 µg/kg of LG BID for one week. PBS or LG injections commenced at the same time that mice were started on normal drinking water or water supplemented with 3% DSS. Injections were administered using a 31 g insulin syringe with an 8 mm long needle and in a final volume that ranged between 85-110 µl. Body weights, food intake, and water intake were determined daily. Blood glucose levels were measured on the first day of the study and just prior to sacrifice. Statistical analyses were done by one-way ANOVA with Bonferroni's Multiple Comparison Post-Test using GraphPad Prism software (version 4). n=5 mice/group.

FIGS. 18A-18D illustrate that doses of Liraglutide lower than those that have shown glucose lowering or cardioprotective effects in rodents [Rolin B, et al, 2002; Noyan-Ashraf M H, et al, 2009; Porter D W et al, 2010; Irwin N et al, 2010; and Gault V A et al, 2011] are still able to increase large intestine size (large intestine weight and length) in wild-type mice compared to PBS-treated mice. FIGS. 18A-18D also illustrate that Liraglutide treatment can increase large intestine size (large intestine length and weight) in wild-type mice on the Balb/c genetic background compared to control-treated mice. All mice were 9-week old female wild-type mice on the Balb/c genetic background. All mice were maintained on a standard rodent chow diet and normal drinking water. Mice were given s.c. injections of either phosphate buffered saline (PBS), 30 µg/kg of Liraglutide (LG) BID, or 50 µg/kg of LG BID for one week. Injections were administered using a 31 g insulin syringe with an 8 mm long needle and in a final volume that ranged between 60-120 µl. Body weights and food intake were determined daily. After one week of treatment, all mice were sacrificed by $CO_2$ asphyxiation (mice did not receive PBS or LG injections on the day of sacrifice). The large intestine was removed and its length was determined by measuring with a ruler placed on a horizontal surface. Luminal contents were removed from the large intestine by flushing with ice-cold PBS using a 60 cc syringe attached to a p200 pipette tip. Mesenteric fat was dissected away from the large intestine. The large intestine was blotted to remove excess PBS and then weighed. Statistical analyses were done by one-way ANOVA with Bonferroni's Multiple Comparison Post-Test using GraphPad Prism software (version 4).

FIG. 19 illustrates that there is no difference in final body weight in wild-type mice on the Balb/c genetic background treated with two different doses of Liraglutide compared to PBS-treated mice. All mice were 9-week old female wild-type mice on the Balb/c genetic background. All mice were maintained on a standard rodent chow diet and normal drinking water. Mice were given s.c. injections of either phosphate buffered saline (PBS), 30 µg/kg of Liraglutide (LG) BID, or 50 µg/kg of LG BID for one week. Injections were administered using a 31 g insulin syringe with an 8 mm long needle and in a final volume that ranged between 60-120 µl. Body weights and food intake were determined daily. Statistical analyses were done by one-way ANOVA with Bonferroni's Multiple Comparison Post-Test using GraphPad Prism software (version 4). n=5 mice/group.

FIG. 20A-20C demonstrate that 11 week-old GLP-1R−/− mice have reduced large intestine size (colon weight and colon length) compared to age- and sex-matched wild-type (WT) control mice. All data are from 11 week-old female mice that were maintained on a standard rodent chow diet and normal drinking water. For bowel dissections, mice were euthanized via $CO_2$ inhalation and their body weight was obtained. The GI tract from the stomach to the distal portion of the large intestine (including the pancreas) was removed from the animal. The length of the large intestine (from the caecum to the rectum) was measured using a ruler placed on a horizontal surface. Luminal contents were removed from the large intestine by flushing with PBS using a 60 cc syringe attached to a p200 pipette tip. Mesenteric fat was dissected away from the large intestine. The large intestine was blotted to remove excess PBS and then weighed. Statistical analyses were done by one-way ANOVA with Bonferroni's Multiple Comparison Post-Test using GraphPad Prism software (version 4).

FIGS. 21A-21H demonstrate that, relative to WT littermate control mice, GLP-1 R−/− mice have inherently reduced levels of mRNA transcripts that encode proteins that are important for:
  (i) preservation of intestinal barrier function, protection of mucosal integrity, and gut repair and wound healing (Tff1, Tff2, Tff3, VIP, and IL-6);
  (ii) increasing vascular permeability and mediating tissue repair (IL-1b);
  (iii) mediating long-term protection against intracellular pathogens (IL-12b); and
  (iv) pathogen recognition and activation of the innate immune system (TLR4).

All mice were 10-week old female wild-type (WT) WT or GLP-1R−/− (KO) littermates on C57Bl/6 genetic background. Mice were maintained on a standard rodent chow diet and either regular drinking water or water supplemented with 3% DSS for a total of one week. Body weights and water intake were determined daily. After one week of normal water or 3% DSS-supplemented drinking water, all mice were sacrificed by CO2 asphyxiation. The GI tract from the stomach to the distal portion of the large intestine (including the pancreas) was removed from the animal. The length of the large intestine (from the caecum to the rectum) was measured using a ruler placed on a horizontal surface. Luminal contents were removed from the large intestine by flushing with ice-cold PBS using a 60 cc syringe attached to a p200 pipette tip. Mesenteric fat was dissected away from the large intestine. The large intestine was blotted to remove excess PBS and then weighed. The large intestine was divided into 3 equal sections representing proximal (closest to caecum), middle, and distal large intestine (closest to rectum). The proximal large intestine section was snap frozen in liquid nitrogen to be used for RNA isolation. The middle large intestine section was snap frozen in liquid nitrogen to be used for protein isolation and assay of myeloperoxidase (MPO) activity. The distal large intestine section was fixed in 10% neutral buffered formalin for 24 hrs, transferred to 70% ethanol and then processed, imbedded, sectioned and stained for hematoxylin and eosin using standard protocols. Total RNA was isolated from large intestine using TRI reagent. First strand cDNA was sythesized from 0.5 µg of total RNA. Real-Time PCR with TaqMan Gene Expression Assays (Applied Biosystems) was carried out using 0.5 µl of cDNA per 10 µl reaction. Levels of mRNA transcripts were normalized to peptidyl-propyl isomerase A (cyclophilin). Statistical analyses were done by one-way ANOVA with Bonferroni's Multiple Comparison Post-Test using GraphPad Prism software (version 4).

FIGS. 22A-22E demonstrate that, relative to WT littermate control mice, GLP-1 R−/− mice have inherently reduced levels of mRNA transcripts that encode proteins that are important for:
  (i) immune system regulation, preservation of intestinal barrier function, protection of mucosal integrity, and regulation of repair (TGFb1, TGFb3, EGFR)
  (ii) intestinal epithelial repair and restitution (HGF, KGF).

All mice were 10-week old female wild-type (WT) WT or GLP-1R−/− (KO) littermates on C57Bl/6 genetic background. Mice were maintained on a standard rodent chow diet and either regular drinking water or water supplemented with 3% DSS for a total of one week. Body weights and water intake were determined daily. After one week of normal water or 3% DSS-supplemented drinking water, all mice were sacrificed by CO2 asphyxiation. The GI tract from the stomach to the distal portion of the large intestine (including the pancreas) was removed from the animal. The length of the large intestine (from the caecum to the rectum) was measured using a ruler placed on a horizontal surface. Luminal contents were removed from the large intestine by flushing with ice-cold PBS using a 60 cc syringe attached to a p200 pipette tip. Mesenteric fat was dissected away from the large intestine. The large intestine was blotted to remove excess PBS and then weighed. The large intestine was divided into 3 equal sections representing proximal (closest to caecum), middle, and distal large intestine (closest to rectum). The proximal large intestine section was snap frozen in liquid nitrogen to be used for RNA isolation. The middle large intestine section was snap frozen in liquid nitrogen to be used for protein isolation and assay of myeloperoxidase (MPO) activity. The distal large intestine section was fixed in 10% neutral buffered formalin for 24 hrs, transferred to 70% ethanol and then processed, imbedded, sectioned and stained for hematoxylin and eosin using standard protocols. Total RNA was isolated from large intestine using TRI reagent. First strand cDNA was sythesized from 0.5 µg of total RNA. Real-Time PCR with TaqMan Gene Expression Assays (Applied Biosystems) was carried out using 0.5 µl of cDNA per 10 µl reaction. Levels of mRNA transcripts were normalized to peptidyl-propyl isomerase A (cyclophilin). Statistical analyses were done by one-way ANOVA with Bonferroni's Multiple Comparison Post-Test using GraphPad Prism software (version 4).

FIGS. 23A and 23B illustrate that acute administration of a GLP-1 receptor agonist increases mRNA levels of insulin-like growth factor 1 (IGF-1) in the murine large bowel. All mice were 8 week-old, random-fed C576B1/6 males that were maintained on a standard rodent chow diet and normal drinking water. Mice were given a single subcutaneous injection of either phosphate buffered saline (PBS), epidermal growth factor (EGF, 0.5 µg/g body weight) or the GLP-1 receptor agonist exendin-4 (Exendin, 1 µg/22 g mouse, ~10 nmol/kg). All injections were administered using a 31 g insulin syringe with an 8 mm long needle and in a final volume of 250 µl. At 15, 30, 45, 60, or 90 min post injection, mice were euthanized via $CO_2$ inhalation and the GI tract from the stomach to the distal portion of the large bowel (including the pancreas) was removed from the animal. The length of the large bowel (from the caecum to the rectum) was measured using a ruler placed on a horizontal surface. Luminal contents were removed from the large bowel by flushing with ice-cold PBS using a 60 cc syringe attached to a p200 pipette tip. Mesenteric fat was dissected away from the large bowel. The large bowel was blotted to remove excess PBS and then weighed. The large bowel was divided into 3 equal sections representing proximal (closest to caecum), middle, and distal colon (closest to rectum). The proximal colon section was snap frozen in liquid nitrogen to be used for RNA isolation. The middle colon section was fixed in 10% neutral buffered formalin for 24 hrs, transferred to 70% ethanol and then processed, imbedded, sectioned and stained for hematoxylin and eosin using standard protocols. The distal colon section was snap frozen in liquid nitrogen to be used for protein isolation and assay of myeloperoxidase (MPO) activity. Total RNA was isolated from large intestine using guanidine isothiocyanate and standard protocols. First strand cDNA was sythesized from 5 μg of total RNA. Real-Time PCR with TaqMan Gene Expression Assays (Applied Biosystems) was carried out using 1 μl of cDNA per 20 μl reaction. Levels of mRNA transcripts were normalized to 18S. Statistical analyses were done by one-way ANOVA with Bonferroni's Multiple Comparison Post-Test using GraphPad Prism software (version 4).

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the domains, cell lines, vectors, methodologies etc. which are reported therein which might be used in connection with the invention. Nothing herein is to be construed as an admission that the invention is not entitled to antedate such disclosure by virtue of prior invention.

Full Citations For Publications (i) The long-acting GLP-1 derivative NN2211 ameliorates glycemia and increases beta-cell mass in diabetic mice. Rolin B, Larsen M O, Gotfredsen C F, Deacon C F, Carr R D, Wilken M, and Knudsen L B. Am J Physiol Endocrinol Metabl. 2002 October; 283(4):E745-52.

(ii) GLP-1R agonist liraglutide activates cytoprotective pathways and improves outcomes after experimental myocardial infarction in mice. Noyan-Ashraf M H, Momen M A, Ban K, Sadi A M, Zhou Y Q, Riazi A M, Baggio L L, Henkelman R M, Husain M, and Drucker D J. Diabetes. 2009 April; 58(4):975-83.

(iii) Four weeks administration of Liraglutide improves memory and learning as well as glycaemic control in mice with high fat dietary-induced obesity and insulin resistance. Porter D W, Kerr B D, Flatt P R, Holscher C, and Gault V A. Diabetes Obes Metab. 2010 October; 12(10): 891-9.

(iv) Insulin-releasing and metabolic effects of small molecule GLP-1 receptor agonist 6,7-dichloro-2-methylsulfonyl-3-N-tert-butylaminoquinoxaline. Irwin N, Flatt P R, Patterson A, and Green B D. Eur J Pharmacol. 2010 Feb. 25; 628(1-3):268-73.

(v) Administration of an acylated GLP-1 and GIP preparation provides added beneficial glucose-lowering and insulinotropic actions over single incretins in mice with type 2 diabetes and obesity. Gault V A, Kerr B D, Harriott P, and Flatt P. Clin Sci (Lond). 2011 Feb. 18. [Epub ahead of print])]

TABLE 1

| Agent | Treatment | Increase colon weight | Increase colon length | Weight of colon per unit length | Weight of colon per gram body weight | decrease body weight | increase blood glucose | increase small bowel weight | increase small bowel length | increase large intestine length | increase large intestine weight |
|---|---|---|---|---|---|---|---|---|---|---|---|
| Liraglutide | 75 μg/kg for 7 days | | No | No | | | | | | | |
| Liraglutide | 75 μg/kg for 14 days | Yes | No | No | Yes | | | | | | |
| Extendin 4 | 10 nmol/kg for 14 days | Yes | No | No | Yes | | | | | | |
| Extendin 4 | 1 μg for 10 days | Yes | Yes | | | | | | | | |
| 3% DSS/Extendin | 5 nmol/kg 7 days | Yes | Yes | | | No | No | Yes | Yes | | |
| 3% DSS/Liguratide | 75 μg/kg for 1 week | | | | | No | No | Yes | Yes | | |
| 3% DSS/Liguratide | 25 μg/kg for 7 days | | | | | No | No | | | | |
| 3% DSS/Liguratide | 50 μg/kg for 7 days | | | | | No | No | Yes | Yes | Yes | Yes |
| 3% DSS/Liguratide | 30 μg/kg for 7 days | | | | | No | Yes | Yes | Yes | Yes | Yes |

What is claimed is:

1. A method of treating a mammalian subject comprising administering to a subject having a condition in which functioning of the small or large intestine is impaired, a GLP-1 receptor agonist, liraglutide, in an amount that does not significantly lower blood glucose, reduce glucose tolerance, or cause significant body weight loss of the subject, to result in the proliferation of the tissue of the small intestine, large intestine, or both.

2. A method according to claim 1, wherein said agonist is administered in a dose of 5 µg/kg per day or less.

3. A method according to claim 1, wherein said agonist is administered in a dose of 0.3 mg per day or less.

4. A method according to claim 1, wherein said agonist is administered in a dose of less than 0.6 mg per day.

5. The method according to claim 1, wherein the amount of GLP-1 receptor agonist administered is effective to increase the size of the intestine in length.

6. The method according to claim 1, wherein the amount of GLP-1 receptor agonist administered is effective to increase the size of the intestine in weight.

* * * * *